US009791459B2

(12) United States Patent
Keller et al.

(10) Patent No.: US 9,791,459 B2
(45) Date of Patent: Oct. 17, 2017

(54) METHOD OF DIAGNOSING AND TREATING ASPHYXIA

(75) Inventors: Matthias Keller, Essen (DE); Hans-Peter Deigner, Lampertheim (DE); David Enot, Creully (FR); Matthias Kohl, Rottweil (DE); Ronnaug Solberg, Oslo (NO); Ola Didrik Saugstad, Oslo (NO); Therese Koal, Innsbruck (AT)

(73) Assignee: InfanDx AG, Cologne (DE)

( * ) Notice: Subject to any disclaimer, the term of this patent is extended or adjusted under 35 U.S.C. 154(b) by 0 days.

(21) Appl. No.: 13/318,797

(22) PCT Filed: May 4, 2010

(86) PCT No.: PCT/EP2010/056048
§ 371 (c)(1),
(2), (4) Date: Feb. 10, 2012

(87) PCT Pub. No.: WO2010/128054
PCT Pub. Date: Nov. 11, 2010

(65) Prior Publication Data
US 2012/0136581 A1 May 31, 2012

(30) Foreign Application Priority Data
May 5, 2009 (EP) ..................... 09159425

(51) Int. Cl.
G01N 33/48 (2006.01)
G01N 33/68 (2006.01)
G06F 19/24 (2011.01)

(52) U.S. Cl.
CPC ..... *G01N 33/6893* (2013.01); *G01N 2800/12* (2013.01); *G06F 19/24* (2013.01)

(58) Field of Classification Search
None
See application file for complete search history.

(56) References Cited

U.S. PATENT DOCUMENTS

| 8,095,389 B2 * | 1/2012 | Dalton et al. ............. 705/3 |
| 2007/0003965 A1 | 1/2007 | Ramsay et al. |
| 2007/0004044 A1 | 1/2007 | Ramsay et al. |

FOREIGN PATENT DOCUMENTS

WO 2007/003343 A 1/2007

OTHER PUBLICATIONS

Khashaba et al. "Excitatory amino acids and magnesium sulfate in neonatal asphyxia," (Brain and Development, vol. 28 (2006) pp. 375-379).*
Taguchi et al. "Identification of Hypoxia-Inducible Factor-1A as a Novel Target for miR-17-92 MicroRNA Cluster" (Cancer Res, vol. 14 (2008) pp. 5540-5545).*
Chu, C. Y. et al, "Metabolomic and Bioinformatic Analyses in Asphyxiated Neonates," Clinical Biochemistry, Mar. 1, 2006, vol. 39, No. 3, p. 203-209.
Mueller P., et al., "Mass Spectrometric Quantifications of Organic Acids and Acylcarnitines in Early Random Urine Specimens of Newborns with Perinatal Complications: Feasibility Study for the Prediction of the Neuro developmental Outcome," The Internet Journal of Pediatrics and Neonatology, 2007, vol. 7, No. 2.
International Search Report and Written Opinion for PCT/EP2010/056048 dated Oct. 14, 2010.
Van Bel, et al., "Drugs for neuroprotection after birth asphyxia: Pharmacologic adjuncts to hypothermia", Seminars in Perinatology, 40 (2016), 152-159.
Hagberg et al., "Perinatal brain damage: The term infant", Neurobiology of Disease 92 (2016), 102-112.
Lawn et al., "Setting Research Priorities to Reduce Almost One Million Deaths from Birth Asphyxia by 2015", PLoS Medicine | www.plosmedicine.org, Jan. 2011, vol. 8, Issue 1, 1-11.
Walsh et al., "The Metabolomic Profile of Umbilical Cord Blood in Neonatal Hypoxic Ischaemic Encephalopathy", PLoS One | www.plosone.org, Dec. 2012, vol. 7, Issue 12, 1-12.
Martinello et al., "Management and investigation of nenatal encephalopathy : 2017 update", Arch Dis Child Fetal Neonatal Ed, F1-F13 (2017).
Diller et al., "Hypothermia Treatment for Brain Injury", Annu. Rev. Biomed. Eng. 2009, 11:135-62.
Eicher et al., "Moderate Hypothermia in Neonatal Encephalopathy: Efficiency Outcomes", Pediatr. Neural 2005; 32: 11-17.
Kurinczuk et al., "Epidemiology of neonatal encepalapathy and hypoxic-ischaemic encephalopathy", Early Human Development 86 (2010) 329-338.
Guillet et al., "Seven- to eight-year follow-up of the CoolCap trial of head cooling for nenonatal encephalopathy", Pediatric Research. vol. 71, No. 2, (2012), 205-209.
Solberg, R., et al., "Metabolomic Analyses of Plasma Reveals New Insights into Asphyxia and Resuscitation in Pigs", PLoS One, Mar. 9, 2010, pp. 1-12, vol. 5.
Liu, Jia, et al., "Outcome-Related Metabolomic Patterns from 1H/31P NMR After Mild Hypothermia Treatments of Oxygen-Glucose Deprivation in a Neonatal Brain Slice Model of Asphyxia", Journal of Cerebral Blood Flow & Metabolism, 2011, pp. 547-559, vol. 31.
Luetjohann, D., et al., "Cholesterol Dynamics in the Foetal and Neonatal Brain as Reflected by Circulatory Levels of 24S-Hydroxycholesterol", Acta Paediatr, 2001, pp. 652-657, vol. 90.

(Continued)

*Primary Examiner* — Anna Skibinsky
(74) *Attorney, Agent, or Firm* — Cahn & Samuels, LLP

(57) ABSTRACT

A method for in vitro diagnosing asphyxia and disorders related thereto, a method of in vitro estimating duration of hypoxia in a patient subjected to asphyxia, and a method for in vitro monitoring of normoxic, hypoxic and hyperoxic conditions and/or normobaric and hyperbaric oxygen therapy, includes quantitatively detecting in a biological sample of a patient a plurality of asphyxia specific endogenous compounds which are selected from the group consisting of biogenic amines; carnitine-derived compounds; amino acids; bile acids; carboxylic acids; eicosanoids; lipids; precursors of cholesterol, cholesterol metabolites; prostanoids; and sugars.

15 Claims, 10 Drawing Sheets

(56) References Cited

OTHER PUBLICATIONS

Spitzer, A.R., et al., "Proteomics-and Metabolomics-Based Neonatal Diagnostics in Assessing and Managing the Critically Ill Neonate", Clin. Perinatal, 2008, pp. 695-716, vol. 35, No. 4.

Lingwood, B.E., et al., "MAP2 Provides Reliable Early Assessment of Neural Injury in the Newborn Piglet Model of Birth Asphyxia", J. Neurosc. Meth., Jun. 2008, pp. 140-146, vol. 171, No. 1.

Vasquez-Vivar J., et al., "Tetrahydrobiopterin in the Prevention of Hypertonia in Hypoxic Fetal Brain", Ann. Neurol., Sep. 2009, pp. 323-331, vol. 66, No. 3.

Shankaran, Seetha, et al., "Whole-Body Hypothermia for Neonates with Hypoxic-Ischemic Encephalopathy", The New England Journal of Medicine, Oct. 13, 2005.

* cited by examiner

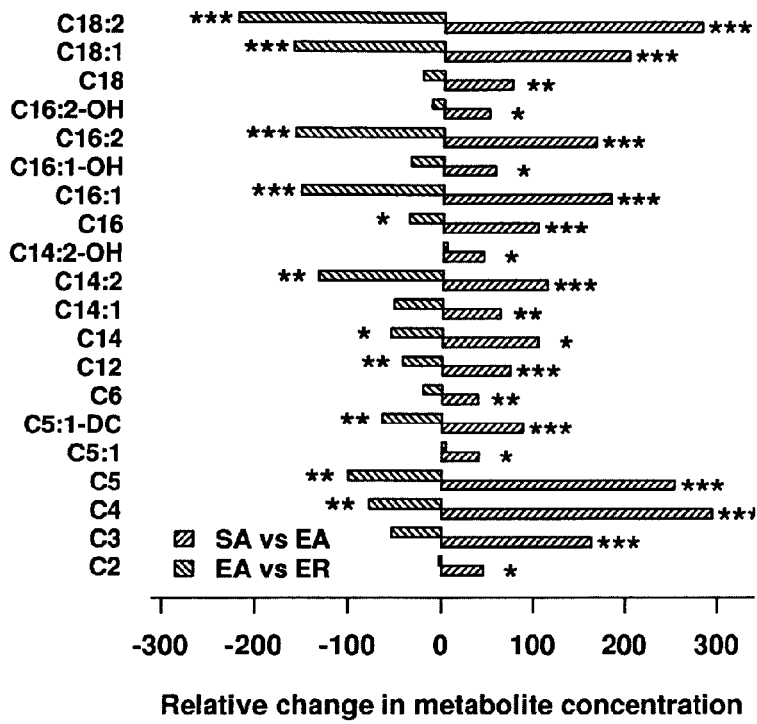

Fig. 1

Relative metabolite concentration changes compared to the control (positive value) or to the treated animals (negative values) after asphyxia (black, Start of Asphyxia (SA) vs End of Asphyxia (EA) and following the resuscitation (end of rescuscitation ER) procedure ( grey, EA vs ER) for the selected set of acyl carnitine derivatives. * denotes significance levels after correction for test multiplicity: q value lower than $10^{-3}$,  $10^{-5}$ and * $10^{-7}$

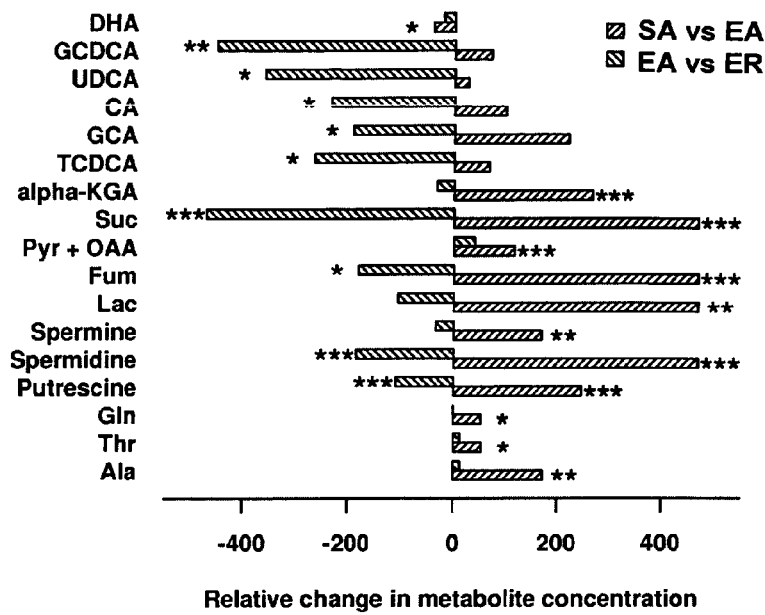

Fig. 2

Relative metabolite concentration changes compared to the control (positive value) or to the treated animals (negative values) after asphyxia (grey, SA vs EA) and following the resuscitation procedure ( black, EA vs ER) for the selected set of metabolites other than acyl carnitine derivatives. * denotes significance levels after correction for test multiplicity: q value lower than $10^{-3}$,  $10^{-5}$ and * $10^{-7}$

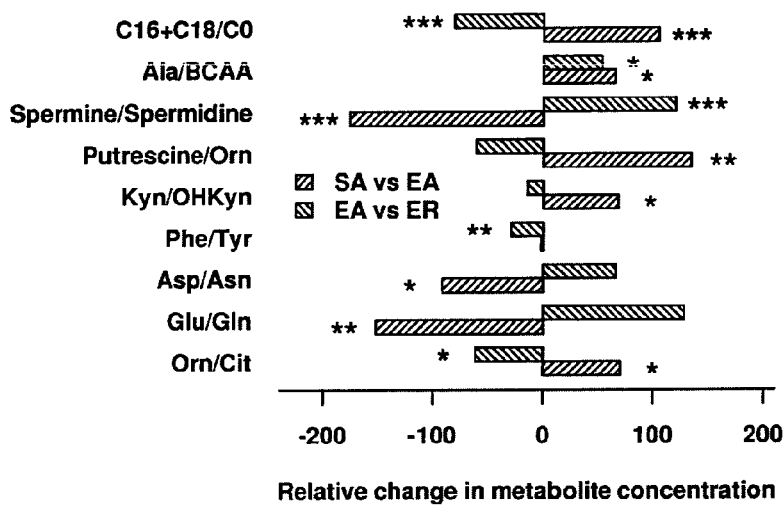

Fig. 3

Relative metabolite concentration changes compared to the control (positive value) or to the treated animals (negative values) after asphyxia (black, SA vs EA) and following the resuscitation procedure (grey, EA vs ER) for a selection of concentration ratios between biologically connected metabolite. * denotes significance levels after correction for test multiplicity: q value lower than $10^{-3}$,  $10^{-5}$ and * $10^{-7}$ Mapping of the samples (scores) on the first two dimensions from a principal component analysis using the full list of analytes given in table 1. This illustrates that the main source of variability in the metabolomics data is clearly related to the asphyxia effect.

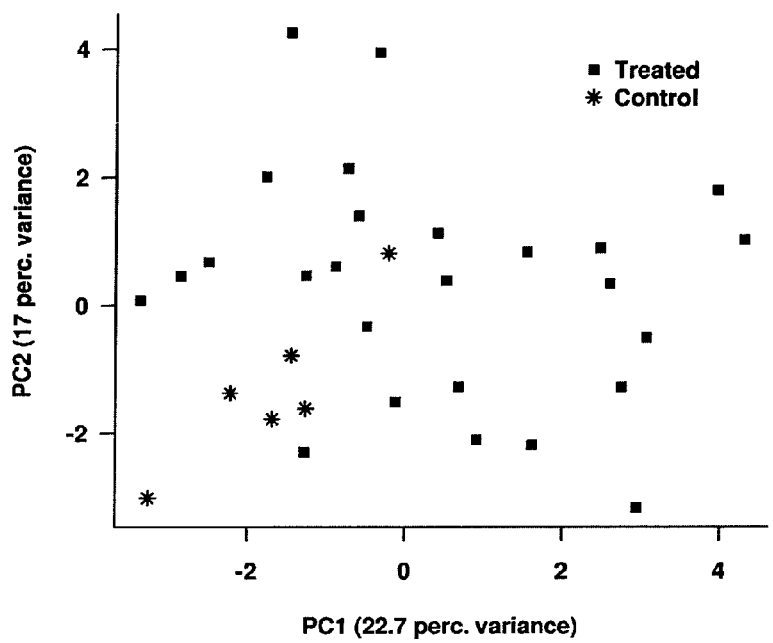

Fig. 4b

Mapping of the samples (scores) on the first two dimensions from a principal component analysis after removing the 30 top ranked metabolites from the list given in table 2. This illustrates that variance associated to the linear combination of the most prominent metabolites is necessary to early detection of asphyxia in the subject. This remarks is confirmed by means of multivariate classification (Fig 4c)

Evaluation of classification performance by mean of repeated bootstrapping using Random Forest with different number of top ranked analytes excluded from the model. Exclusion of the top ranked metabolites is translated by a dramatic loss of classification efficiency and an increased variance of its error estimates.

Receiver operator characteristics curves: an individual clinical parameter (heart rate, HR), a predictive metabolite from table 1 and the combination of these two to discriminate healthy and asphyxiated subjects.

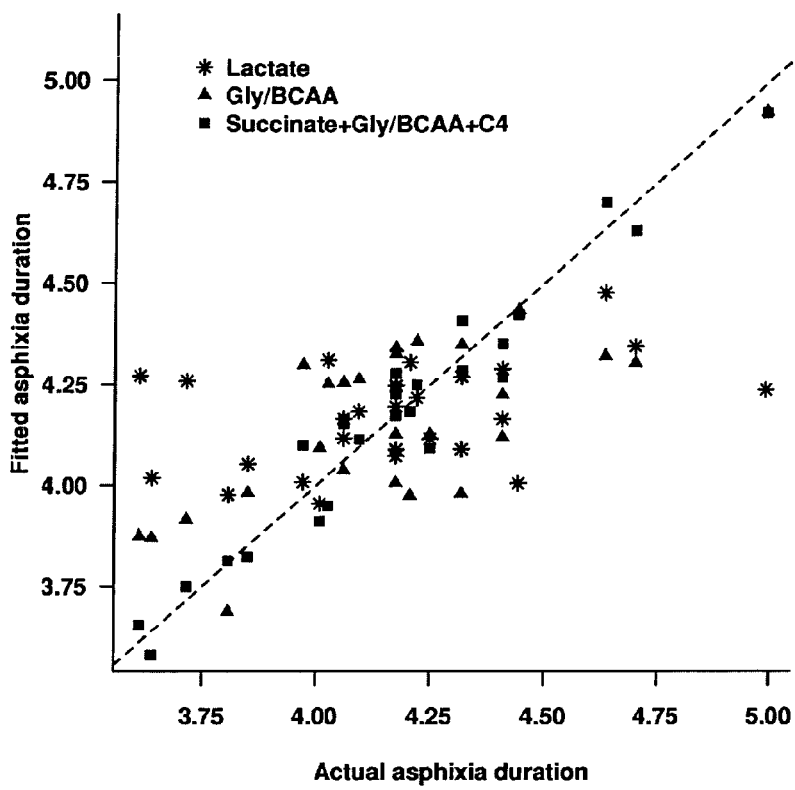

Fig. 6

Metabolites can be used to determine the time of hypoxia and therefore reoxygenation: actual versus fitted hypoxia length (in minutes, log scale) for 26 animals from regression models involving commonly used marker lactate (grey asterisks), Gly/BCAA ratio (black triangles) and a combination of three metabolomics parameters (black squares). Abbreviations: C4 = Butyrylcarnitine / Isobutyrylcarnitine; BCAA=branched chain amino acids; Gly=Glycine

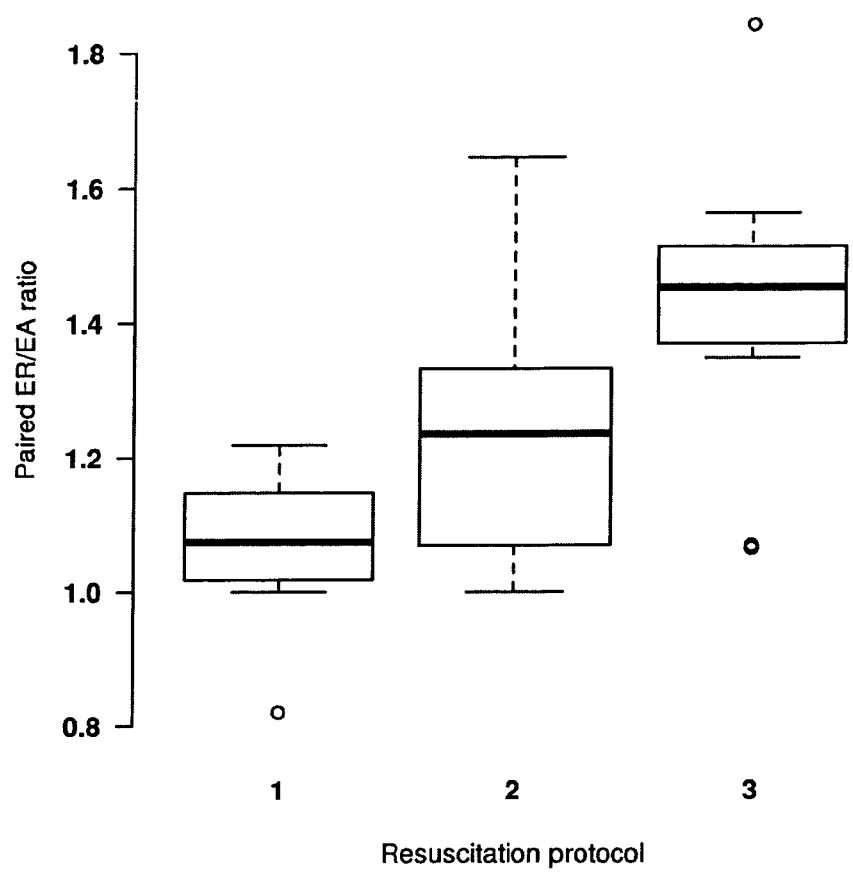
Fig. 7a: Decadienyl-L-carnitine

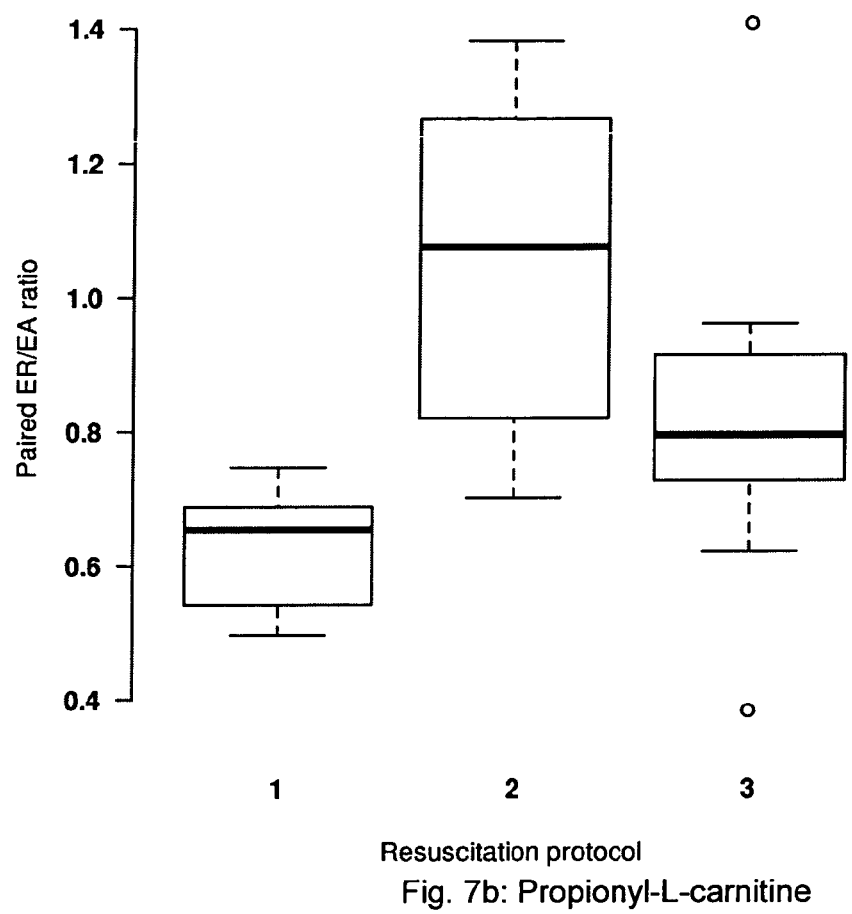
Fig. 7b: Propionyl-L-carnitine

METHOD OF DIAGNOSING AND TREATING ASPHYXIA

This U.S. patent application is a national stage application of PCT/EP2010/056048 filed on 4 May 2010 and claims priority of European patent document 09159425.9 filed on 5 May 2009, the entirety of which is incorporated herein by reference The present invention relates to a method for in vitro diagnosing asphyxia and disorders related to hypoxia, a method of in vitro estimating duration of hypoxia in a patient, a method for in vitro monitoring of normoxic, hypoxic and hyperoxic conditions and/or normobaric and hyperbaric oxygen therapy, and to a Kit.

The invention generally relates to biomarkers for asphyxia as tools in clinical diagnosis for early detection of asphyxia, therapy monitoring and methods based on the same biomarkers.

BACKGROUND

In technically developed countries, perinatal asphyxia affects 3-5 per 1000 live births with subsequent moderate or severe hypoxic ischaemic encephalopathy (HIE) in 0.5-1 per 1000 live births (Levene 1986). HIE is a major problem worldwide as 10-60% of affected infants die, and at least 25% of survivors have long term neurodevelopmental sequelae (Vannucci 1990). In addition 5-10% of newborns require some kind of assistance to start breathing after birth. The aim of resuscitation and resuscitation monitoring by appropriate diagnostic marker is to prevent death and adverse long term neurodevelopmental impairment.

Until recently the therapy was limited to preventive measures and symptomatic supportive strategies after asphyxia. However, asphyxia, hypoxia and related disorders are potentially treatable disorders which potentially impair memory or other mental functions or physical functions. Recent experimental and clinical study clearly show a benefit of hypothermia as a clinically feasible manoeuvre that improve the outcome of neonates with HIE. It has been shown that a delay of hypothermia reduces the neuroprotective potential or the earlier the therapy is initiated the higher the protective effect. Recent research has shown that using extra oxygen for newborn resuscitation will negatively influence both morbidity and mortality. Oxygen inhibits protein synthesis and/or increases their degradation and also is a potent activator and/or suppressor of a number of genes. Furthermore, it contributes to the regulation of membrane transport, intracellular signalling and the initiation of apoptosis.

In addition, in particular in treatment of decompression sickness occurring after recreational or professional scuba diving, it is common to treat patients with 100% oxygen under hyperbaric conditions in a pressure chamber, in order to get rid of nitrogen excess bubbling out after a decompression accident causing symptoms from skin itching to complete paralysis. A hyperbaric oxygen treatment [HBO] protocol is published in the US Navy Treatment Table 6, which is also used with slight modifications in German (GTÜM) and Austrian (ÖGTH) diving and hyberbaric medical associations. itypical treatment. In this treatment protocols a patient suffering from decompression sickness is intermittently exposed to a maximum pressure of 2.8 bar/2.4 bar (corresponding to a water depth of 18 m/14 m) for up to several hours and repeated treatments over several weeks, if necessary.

Currently, no reliable monitoring of oxygen induced damages, in particular brain damages, during HBO therapy is existing, only the clinical signs of a CNS oxygen toxicity, such as neuromuscular spasms are available.

Accordingly, there is an urgent need for timely treatment and early diagnosis of asphyxia, in particular in newborns, and, as pointed out above, an urgent need for therapy monitoring given e.g. detrimental effects due to excess oxygen administration upon treatment.

SUMMARY OF INVENTION

These needs are met by a method for in vitro diagnosing asphyxia and disorders related thereto, a method of in vitro estimating duration of hypoxia in a patient subjected to asphyxia, Method for in vitro monitoring of normoxic, hypoxic and hyperoxic conditions and/or normobaric and hyperbaric oxygen therapy, and a kit.

In particular, the present invention relates to a method for in vitro diagnosing asphyxia and disorders related thereto, comprising quantitatively detecting in at least one biological sample of at least one tissue of a mammalian subject a plurality of asphyxia specific compounds having a molecular weight of less than 1500 Dalton, except lactate, comprising the steps of:
a) selecting said compounds;
b) measuring at least one of the parameters selected from the group consisting of: concentration, level or amount of each individual metabolite of said plurality of metabolites in said sample, qualitative and/or quantitative molecular pattern and/or molecular signature; and using and storing the obtained set of values in a database;
c) calibrating said values by comparing asphyxia-positive and/or asphyxia-negative reference parameters;
d) comparing said measured values in the sample with the calibrated values, in order to assess whether the patient is asphyxia-positive or asphyxia-negative.

In a preferred method according to the invention, said asphyxia specific compounds are endogenous compounds being selected from the group consisting of biogenic amines; carnitine-derived compounds; amino acids; bile acids; carboxylic acids; eicosanoids; lipids; precursors of cholesterol, cholesterol metabolites, prostanoids; and sugars.

Preferred asphyxia specific endogenous compounds are selected from the group consisting of: carnitine; acyl carnitines, in particular, Decanoylcarnitine, Fumarylcarnitine, Decenoylcarnitine, Decadienoylcarnitine, Dodecanoylcarnitine, Dodecanedioylcarnitine, Dodecenoylcarnitine, Tetradecanoylcarnitine, Tetradecenoylcarnitine, 3-Hydroxytetradecenoylcarnitine, Tetradecadienoylcarnitine, 3-Hydroxytetradecadienoylcarnitine, Hexa-decanoylcarnitine, 3-Hydroxyhexadecanolycarnitine, Hexadecenoylcarnitine, 3-Hydroxyhexa-decenoylcarnitine, Hexadecadienoylcarnitine, 3-Hydroxyhexadecadienoylcarnitine, Octadecanoylcarnitine, Octadecenoylcarnitine, 3-Hydroxyoctadecenoylcarnitine, Octadecadienoylcarnitine, Acetylcarnitine, Propionylcarnitine, Hydroxypropionylcarnitine, Propenoylcarnitine, Butyrylcarnitine, Isobutyrylcarnitine, 3-Hydroxybutyrylcarnitine, Butenoylcarnitine, Isovalerylcarnitine, 2-Methylbutyrylcarnitine, Valerylcarnitine, Glutarylcarnitine, 3-Hydroxyisovalerylcarnitine, 3-Hydroxy-2-methylbutyrylcarnitine, Tiglylcarnitine, 3-Methylcrotonylcarnitine, Glutaconylcarnitine, Mesaconylcarnitine (Undecanoylcarnitine), Hexanoylcarnitine, Hexenoylcarnitine, Pimelylcarnitine, Octanoylcarnitine, Octenoylcarnitine, and Nonanoylcarnitine;

bile acids, in particular Taurochenodeoxycholic Acid, Glycocholic Acid, Cholic Acid, Ursodeoxycholic Acid, Chenodeoxycholic Acid, Glycochenodeoxycholic Acid, Lithocholic Acid, biogenic amines, in particular, asymmetric dimethylarginine, symmetric dimethylarginine, total dimethylarginine, histamine, kynurenine, hydroxykynurenine, putrescine, spermidine, spermine, serotonin, creatinine;

amino acids, in particular; Glycine, Alanine, Serine, Proline, Valine, Threonine, isoleucine, Leucine, Isoleucine, Asparagine, Aspartic acid, Glutamine, Glutamate, Methionine, Histidine, Phenylalanine, Arginine, Citrulline, Tyrosine, Tryptophane, Ornithine, Lysine; Methionine-Sulfoxide, Aspartic acid, Arginine;

carboxylic acids, in particular fumaric acid, pyruvate, oxaloacetate, succinic acid, alpha-Ketoglutaric acid;

phospholipids, in particular glycerophospholipids, such as:
Phosphatidylcholine with diacyl residue sum C24:0*

[*wherein the number following "C" represents the number of carbon atoms in the residue, and the number after the colon represents the number of double bonds in the residue]

Phosphatidylcholine with diacyl residue sum C26:0
Phosphatidylcholine with diacyl residue sum C28:1
Phosphatidylcholine with diacyl residue sum C30:0
Phosphatidylcholine with diacyl residue sum C30:2
Phosphatidylcholine with diacyl residue sum C32:0
Phosphatidylcholine with diacyl residue sum C32:1
Phosphatidylcholine with diacyl residue sum C32:2
Phosphatidylcholine with diacyl residue sum C32:3
Phosphatidylcholine with diacyl residue sum C34:1
Phosphatidylcholine with diacyl residue sum C34:2
Phosphatidylcholine with diacyl residue sum C34:3
Phosphatidylcholine with diacyl residue sum C34:4
Phosphatidylcholine with diacyl residue sum C36:0
Phosphatidylcholine with diacyl residue sum C36:1
Phosphatidylcholine with diacyl residue sum C36:2
Phosphatidylcholine with diacyl residue sum C36:3
Phosphatidylcholine with diacyl residue sum C36:4
Phosphatidylcholine with diacyl residue sum C36:5
Phosphatidylcholine with diacyl residue sum C36:6
Phosphatidylcholine with diacyl residue sum C38:0
Phosphatidylcholine with diacyl residue sum C38:1
Phosphatidylcholine with diacyl residue sum C38:3
Phosphatidylcholine with diacyl residue sum C38:4
Phosphatidylcholine with diacyl residue sum C38:5
Phosphatidylcholine with diacyl residue sum C38:6
Phosphatidylcholine with diacyl residue sum C40:1
Phosphatidylcholine with diacyl residue sum C40:2
Phosphatidylcholine with diacyl residue sum C40:3
Phosphatidylcholine with diacyl residue sum C40:4
Phosphatidylcholine with diacyl residue sum C40:5
Phosphatidylcholine with diacyl residue sum C40:6
Phosphatidylcholine with diacyl residue sum C42:0
Phosphatidylcholine with diacyl residue sum C42:1
Phosphatidylcholine with diacyl residue sum C42:2
Phosphatidylcholine with diacyl residue sum C42:4
Phosphatidylcholine with diacyl residue sum C42:5
Phosphatidylcholine with diacyl residue sum C42:6
Phosphatidylcholine with acyl-alkyl residue sum C30:0
Phosphatidylcholine with acyl-alkyl residue sum C30:1
Phosphatidylcholine with acyl-alkyl residue sum C30:2
Phosphatidylcholine with acyl-alkyl residue sum C32:1
Phosphatidylcholine with acyl-alkyl residue sum C32:2
Phosphatidylcholine with acyl-alkyl residue sum C34:0
Phosphatidylcholine with acyl-alkyl residue sum C34:1
Phosphatidylcholine with acyl-alkyl residue sum C34:2
Phosphatidylcholine with acyl-alkyl residue sum C34:3
Phosphatidylcholine with acyl-alkyl residue sum C36:0
Phosphatidylcholine with acyl-alkyl residue sum C36:1
Phosphatidylcholine with acyl-alkyl residue sum C36:2
Phosphatidylcholine with acyl-alkyl residue sum C36:3
Phosphatidylcholine with acyl-alkyl residue sum C36:4
Phosphatidylcholine with acyl-alkyl residue sum C36:5
Phosphatidylcholine with acyl-alkyl residue sum C38:0
Phosphatidylcholine with acyl-alkyl residue sum C38:1
Phosphatidylcholine with acyl-alkyl residue sum C38:2
Phosphatidylcholine with acyl-alkyl residue sum C38:3
Phosphatidylcholine with acyl-alkyl residue sum C38:4
Phosphatidylcholine with acyl-alkyl residue sum C38:5
Phosphatidylcholine with acyl-alkyl residue sum C38:6
Phosphatidylcholine with acyl-alkyl residue sum C40:0
Phosphatidylcholine with acyl-alkyl residue sum C40:1
Phosphatidylcholine with acyl-alkyl residue sum C40:2
Phosphatidylcholine with acyl-alkyl residue sum C40:3
Phosphatidylcholine with acyl-alkyl residue sum C40:4
Phosphatidylcholine with acyl-alkyl residue sum C40:5
Phosphatidylcholine with acyl-alkyl residue sum C40:6
Phosphatidylcholine with acyl-alkyl residue sum C42:0
Phosphatidylcholine with acyl-alkyl residue sum C42:1
Phosphatidylcholine with acyl-alkyl residue sum C42:2
Phosphatidylcholine with acyl-alkyl residue sum C42:3
Phosphatidylcholine with acyl-alkyl residue sum C42:4
Phosphatidylcholine with acyl-alkyl residue sum C42:5
Phosphatidylcholine with acyl-alkyl residue sum C44:3
Phosphatidylcholine with acyl-alkyl residue sum C44:4
Phosphatidylcholine with acyl-alkyl residue sum C44:5
Phosphatidylcholine with acyl-alkyl residue sum C44:6
Lysophosphatidylcholine with acyl residue C14:0
Lysophosphatidylcholine with acyl residue C16:0
Lysophosphatidylcholine with acyl residue C16:1
Lysophosphatidylcholine with acyl residue C17:0
Lysophosphatidylcholine with acyl residue C18:0
Lysophosphatidylcholine with acyl residue C18:1
Lysophosphatidylcholine with acyl residue C18:2
Lysophosphatidylcholine with acyl residue C20:3
Lysophosphatidylcholine with acyl residue C20:4
Lysophosphatidylcholine with acyl residue C24:0
Lysophosphatidylcholine with acyl residue C26:0
Lysophosphatidylcholine with acyl residue C26:1
Lysophosphatidylcholine with acyl residue C28:0
Lysophosphatidylcholine with acyl residue C28:1
Lysophosphatidylcholine with acyl residue C6:0;

sphingolipids, in particular
Hydroxysphingomyelin with acyl residue sum C14:1
Hydroxysphingomyelin with acyl residue sum C16:1
Hydroxysphingomyelin with acyl residue sum C22:1
Hydroxysphingomyelin with acyl residue sum C22:2
Hydroxysphingomyelin with acyl residue sum C24:1
sphingomyelin with acyl residue sum C16:0
sphingomyelin with acyl residue sum C16:1
sphingomyelin with acyl residue sum C18:0
sphingomyelin with acyl residue sum C18:1
sphingomyelin with acyl residue sum C20:2
sphingomyelin with acyl residue sum C22:3
sphingomyelin with acyl residue sum C24:0
sphingomyelin with acyl residue sum C24:1
sphingomyelin with acyl residue sum C26:0
sphingomyelin with acyl residue sum C26:1;

precursors of cholesterol, cholesterol metabolites, including stereoisomers, in particular (3beta,22R)-cholest-5-ene-3,22-diol, (3beta,24S)-cholest-5-ene-3,24-diol, cholest-5-ene-3beta,25-diol, (3beta,25R)-cholest-5-ene-3,26,diol, (20S)-cholest-5-ene-3beta,20-diol, (3beta,22S)-cholest-5-ene-3,22-diol, (3alpha,5beta)-24,25-epoxy-cholestan-3-ol, cholestane-3beta,5alpha, 6beta-triol, (3beta,7alpha)-cholest-5-ene-3,7-diol, 3-hydroxy-(3-beta)-cholest-5-en-7-one, 5,6-epoxy-(3beta,5beta,6beta)-cholestan-3-ol, 5,6-epoxy-(3beta,5alpha,6alpha)-cholestan-3-ol, (3beta,4beta)-cholest-5-ene-3,4-diol, (3beta)-cholesta-5,24-dien-3-ol, (3beta)-cholesta-5,7-dien-3-ol, cholest-5-en-3-one, (3beta)-lanosta-8,24-dien-3-ol, (3beta)-Lanost-8-en-3-ol;

prostanoids, in particular thromboxanes; prostacyclines; prostaglandines, in particular 13(S)-hydroxy-9Z,11E-octadecadienoic acid, docosahexaenoic acid, arachidonic acid; and sugars, in particular, hexoses such as glucose.

A preferred embodiment of the present invention comprises a method wherein said compound is selected from the group consisting of: Succinate, butyrylcarnitine/isobutyrylcarnitine, fumarate, glycocholic acid, hexadecadienoylcarnitine, putrescine, Glu/Gln, hexadecanoylcarnitine, decdienoylcarnitine, taurochenoxycholic acid, glycochenodeoxycholic acid, spermidine, lysophosphatidylcholine with acyl residue C18:2, cholic acid, valerylcarnitine, spermine, pyruvate, oxaloacetate, glutarylcarnitine, propionylcarnitine, Lys, alpha-ketoglutaric acid, octadecenoylcarnitine, tetradecadienoylcarnitine, Asp/Asn, ursodeoxycholic acid, PC ae C40:4, Serotonin, ornithine, citrate.

In a further preferred embodiment of the present invention, the method is characterized in that said calibration step is carried out by
  a) mathematically preprocessing said values in order to reduce technical errors being inherent to the measuring procedures used in claim 1;
  b) selecting at least one suitable classifying algorithm from the group consisting of logistic regression, (diagonal) linear or quadratic discriminant analysis (LDA, QDA, DLDA, DQDA), perceptron, shrunken centroids regularized discriminant analysis (RDA), random forests (RF), neural networks (NN), Bayesian networks, hidden Markov models, support vector machines (SVM), generalized partial least squares (GPLS), partitioning around medoids (PAM), inductive logic programming (ILP), generalized additive models, gaussian processes, regularized least square regression, self organizing maps (SOM), recursive partitioning and regression trees, K-nearest neighbor classifiers (K-NN), fuzzy classifiers, bagging, boosting, and naïve Bayes; and applying said selected classifier algorithm to said preprocessed data of step a);
  c) said classifier algorithms of step b) being trained on at least one training data set containing preprocessed data from subjects being divided into classes according to their asphyxia-related pathophysiological, physiological, prognostic, or responder conditions, in order to select a classifier function to map said preprocessed data to said conditions;
  d) applying said trained classifier algorithms of step c) to a preprocessed data set of a subject with unknown asphyxia-related pathophysiological, physiological, prognostic, or responder condition, and using the trained classifier algorithms to predict the class label of said data set in order to diagnose the asphyxia status of the subject In accordance with the present invention, the includes that the asphyxia is perinatal asphyxia, choking, drowning, electric shock, injury, or the inhalation of toxic gases, and said disorders being related to hypoxia includes hypoxic ischemic encephalopathy.

An advantageous method is characterized in that said step of mathematically preprocessing in step 2 a) of said raw data obtained in step 1 b) is carried out by a statistical method selected from the group consisting of:
in case of raw data obtained by optical spectroscopy (UV, visible, IR, Fluorescence): background correction and/or normalization;
in case of raw data obtained by mass spectroscopy or mass spectroscopy coupled to liquid or gas chromatography or capillary electrophoresis or by 2D gel electrophoresis, quantitative determination with ELISA or RIA or determination of concentrations/amounts by quantitation of immunoblots or quantitation of amounts of biomolecules bound to aptamers: smoothing, baseline correction, peak picking, optionally, additional further data transformation such as taking the logarithm in order to carry out a stabilization of the variances.

Furthermore, it is preferred that after preprocessing step 2 a) a further step of feature selection is inserted, in order to find a lower dimensional subset of features with the highest discriminatory power between classes;
and/or said feature selection is carried out by a filter and/or a wrapper approach;
and/or wherein said filter approach includes rankers and/or feature subset evaluation methods; and/or wherein said wrapper approach is applied, where a classifier is used to evaluate attribute subsets.

In a preferred embodiment of the present invention, said pathophysiological condition corresponds to the label "diseased" and said physiological condition corresponds to the label "healthy" or said pathophysiological condition corresponds to different labels of "grades of a disease", "subtypes of a disease", different values of a "score for a defined disease"; said prognostic condition corresponds to a label "good", "medium", "poor", or "therapeutically responding" or "therapeutically non-responding" or "therapeutically poor responding."

The metabolic data of the present invention are preferably obtained by high-throughput mass spectrometry data It is further preferred that said asphyxia specific endogenous compounds are asphyxia specific endogenous metabolites.

However, it is also possible to measure antisense nucleic acids, siRNAs and/or miRNAs that inhibit the expression of one or more enzymes being involved in the synthesis or breakdown of asphyxia specific endogenous metabolites, instead or in addition of measurement of asphyxia specific endogenous metabolites.

A particular useful application of the method in accordance with the present invention is that said disorder is hypoxic ischemic encephalopathy, said mammalian subject is a human being, said biological sample is blood, wherein missing data is imputed;
wherein raw data of metabolite concentrations are preprocessed using the log transformation;
wherein linear mixed effect models are used to identify metabolites which are differentially present;
wherein random forest is selected as suitable classifying algorithm, the training of the classifying algorithm including preprocessed metabolite concentrations, is carried out with stratified bootstrap replications
applying said trained random forests classifier to said preprocessed metabolite concentration data set to a subject under suspicion of having hypoxic ischemic encephalopathy, and using the trained classifier to diagnose hypoxic ischemic encephalopathy.

Preferably, the tissue from which the biological samples can be obtained is selected from the group consisting of blood and other body fluids, cerebrospinal fluids, urine; brain tissue, nerve tissue, and/or said sample is a biopsy sample and/or said mammalian subject includes humans; and/or
the method further comprises inclusion of standard lab parameters commonly used in clinical chemistry and critical care units, in particular, blood gases, preferably arterial blood oxygen, blood pH, base status, and lactate, serum and/or plasma levels of routinely used low molecular weight biochemical compounds, enzymes, enzymatic activities, cell surface receptors and/or cell counts, in particular red and/or white cell counts, platelet counts.

The present invention furthermore, is directed to a method of in vitro estimating duration of hypoxia in a patient subjected to asphyxia, comprising quantitatively detecting in at least one biological sample of at least one tissue of the patient a plurality of asphyxia specific endogenous compounds having a molecular weight of less than 1500 Dalton, which are selected from the group consisting of biogenic amines; carnitine-derived compounds; amino acids; bile acids; carboxylic acids; eicosanoids; lipids; precursors of cholesterol, cholesterol metabolites; prostanoids; and sugars;
and calibrating preprocessed detected values by means of regression analysis with known duration of hypoxia and applying the obtained regression function to the preprocessed detected value data set of a patient under hypoxia, and using the regression function to calculate the duration of hypoxia.

One preferred method of in vitro estimating duration of hypoxia is characterized in that lactate, glycine, valine, leucine, isoleucine, butyrylcarnitine, and/or isobutyrylcarnitine, and/or precursors of cholesterol, cholesterol metabolites, in particular oxysterols, are used as said asphyxia specific endogenous compounds.

Furthermore, it was found that blood concentrations of lactate; glycine, in particular as ratio of glycine concentration and the total of branched chain amino acid concentrations of valine, leucine, isoleucine [BCAA]; butyrylcarnitine; and/or isobutyrylcarnitine, oxysterols, in particular precursors of cholesterol, cholesterol metabolites, preferably (3beta,22R)-cholest-5-ene-3,22-diol, (3beta,24S)-cholest-5-ene-3,24-diol, cholest-5-ene-3beta,25-diol, (3beta,25R)-cholest-5-ene-3,26,diol, (20S)-cholest-5-ene-3beta,20-diol, (3beta,22S)-cholest-5-ene-3,22-diol, (3alpha,5beta)-24,25-epoxy-cholestan-3-ol, cholestane-3beta,5alpha, 6beta-triol, (3beta,7alpha)-cholest-5-ene-3,7-diol, 3-hydroxy-(3-beta)-cholest-5-en-7-one, 5,6-epoxy-(3beta,5beta,6beta)-cholestan-3-ol, 5,6-epoxy-(3beta,5alpha,6alpha)-cholestan-3-ol, (3beta,4beta)-cholest-5-ene-3,4-diol, (3beta)-cholesta-5,24-dien-3-ol, (3beta)-cholesta-5,7-dien-3-ol, cholest-5-en-3-one, (3beta)-lanosta-8,24-dien-3-ol, (3beta)-Lanost-8-en-3-ol, are used to estimate duration of hypoxia are particularly effective for assessing duration of hypoxia.

Furthermore, with the methods of the present invention, for the first time, a method for in vitro monitoring of normoxic, hypoxic and hyperoxic conditions and/or normobaric and hyperbaric oxygen therapy is provided. Such method is characterized by quantitatively detecting in at least one biological sample of at least one tissue of a mammalian subject a plurality of asphyxia specific compounds being selected from the group consisting of biogenic amines; carnitine-derived compounds; amino acids; bile acids; carboxylic acids; eicosanoids; lipids; precursors of cholesterol, cholesterol metabolites, prostanoids; and sugars; and
calibrating preprocessed detected values by means of training a linear discriminant analysis classifier with known stages of oxygenation and/or oxygen induced injuries of a mammalian subject and applying the trained classifier to said preprocessed value data set of a subject under oxygen therapy and using the trained classifier to determine the stage of oxygenation and/or oxygen induced injury.

Such monitoring method is further characterized in that said hypoxic conditions include asphyxia, in particular, perinatal asphyxia, choking, drowning, electric shock, injury, or the inhalation of toxic gases, and sleep apnea syndrome, and said disorders being related to hypoxia includes hypoxic ischemic encephalopathy, Finally, the present invention discloses a kit for carrying out the methods of the present invention, comprising:
a) detection agents for the detection of asphyxia specific endogenous metabolites, wherein said metabolites are selected from the group consisting of biogenic amines; carnitine-derived compounds; amino acids; bile acids; carboxylic acids; eicosanoids; lipids; precursors of cholesterol, cholesterol metabolites; prostanoids; and sugars;
b) positive and/or negative controls; and
c) classification software for classification of the results achieved with said detection agents.

Currently used diagnostic methods require time and appropriate equipment (MRI; aEEG), with high costs and frequently unsatisfying sensitivities. Current diagnostics in clinical routine is limited to a) clinical information (APGAR) b) use of basic biochemical information of pH, lactate and base deficit c) use of cerebral function monitoring (aEEG) or EEG. However this used diagnostic means have major limitations either to reduced area under the curve (AUC) and/or delay of diagnosis or increased costs due to equipment required.

Therefore, there is an urgent need for early (immediately after asphyxia) biomarkers enabling early and reliable diagnosis, risk stratification of asphyxia per se, asphyxia duration and severity and asphyxia-induced hypoxic-ischemic encephalopathy. Since metabolite concentration differences in biological fluids and tissues provide links to the various phenotypical responses, metabolites are suitable biomarker candidates.

A major goal of the diagnostic workup is to discriminate mild transient asphyxia and perinatal stress from long-lasting moderate and/or severe asphyxia with the risk of hypoxia-induced disorders.

In classical patient screening and diagnosis, the medical practitioner uses a number of diagnostic tools for diagnosing a patient suffering from a certain disease. Among these tools, measurement of a series of single routine parameters, e.g. in a blood sample, is a common diagnostic laboratory approach. These single parameters comprise for example enzyme activities and enzyme concentration and/or detection of metabolic indicators such as glucose and the like. As far as such diseases are concerned which easily and unambiguously can be correlated with one single parameter or a few number of parameters achieved by clinical chemistry, these parameters have proved to be indispensable tools in modern laboratory medicine and diagnosis. Under the provision that excellently validated cut-off values can be provided, such as in the case of diabetes, clinical chemical parameters such as blood glucose can be reliably used in diagnosis.

In particular, when investigating pathophysiological states underlying essentially a well known pathophysiological mechanism, from which the guiding parameter is resulting, such as a high glucose concentration in blood typically reflects an inherited defect of an insulin gene, such single parameters have proved to be reliable biomarkers for "its" diseases.

However, in pathophysiological conditions, such as cancer or demyelinating diseases such as multiple sclerosis which share a lack of an unambiguously assignable single parameter or marker, differential diagnosis from blood or tissue samples is currently difficult to impossible.

The present invention provides methods for diagnosing whether a subject suffered from asphyxia as well as the duration/severity immediately after the event. Such methods comprise the steps of: analyzing a biological sample from a subject to determine the level(s) of one or more biomarkers for asphyxia in the sample, where the one or more biomarkers are selected from Table 2; and comparing the level(s) of the one or more biomarkers—respectively a composed value/score generated by subjecting the concentrations of individual biomarkers in the sample to a classification method such as affording an equation processing single concentration values—to obtain a separation between both (diseased and healthy) groups.

Such methods comprise the steps of: analyzing a biological sample from a subject to determine the level(s) of one or more biomarkers for asphyxia in the sample, where the one or more biomarkers are selected from Table 2; and comparing the level(s) of the one or more biomarkers in the sample to asphyxia positive or asphyxia negative reference levels of the one or more biomarkers in order to determine whether the subject is developing asphyxia.

The present invention provides a solution to the problem described above, and generally relates to the use of metabolomics data, generated by quantitation of endogenous metabolites by but not limited to mass spectrometry (MS), in particular MS-technologies such as MALDI, ESI, atmospheric pressure pressure chemical ionization (APCI), and other methods, determination of metabolite concentrations by use of MS-technologies or alternative methods coupled to separatrion (LC-MS, GC-MS, CE-MS), subsequent feature selection and/or the combination of features to classifiers including molecular data of at least two molecules.

The concentrations of the individual markers, analytes, metabolites thus are measured and compared to reference values or data combined and processed to scores, classifiers and compared to reference values thus indicating diseased states etc. with superior sensitivities and specificities compared to known procedures, clinical parameters and biomarkers.

For example, in some embodiments, the present invention provides a method of diagnosing Asphyxia and/or duration/severity comprising: detecting the presence or absence of one or more (e.g., 2 or more, 3 or more, 5 or more, 10 or more, etc. measured together in a multiplex or panel format) asphyxia specific metabolites according to table 2 in a sample (e.g., a tissue (e.g., biopsy) sample, a blood sample, a serum sample, or a urine sample) from a subject; and diagnosing asphyxia based on the presence of the asphyxia specific metabolite.

In some embodiments, the specific metabolite is present in asphyctic samples but not non-asphyctic samples. In some embodiments, one or more additional asphyxia markers are detected (e.g., in a panel or multiplex format) along with the asphyxia specific metabolites.

The present invention further provides a method of screening compounds, comprising: contacting an animal, a tissue, a cell containing an asphyxia-specific metabolite with a test compound; and detecting the level of the asphyxia specific metabolite. In some embodiments, the method further comprises the step of comparing the level of the asphyxia specific metabolite in the presence of the test compound or therapeutic intervention to the level of the asphyxia specific metabolite in the absence of the asphyxia specific metabolite. In some embodiments, the cell is in vitro, in a non-human mammal, or ex vivo. In some embodiments, the test compound is a small molecule or a nucleic acid (e.g., antisense nucleic acid, a siRNA, or a miRNA) or oxygen/xenon or any neuroprotective drug that inhibits the expression of an enzyme involved in the synthesis or breakdown of an asphyxia specific metabolite. In some embodiments, the method is a high throughput method.

In one embodiment, the biomarker is a classifier generated from metabolite and analyte concentrations listed in tables 1 to 3.

BRIEF DESCRIPTION OF THE DRAWINGS

Further aspects, advantages and embodiments of the present invention will become evident by the description of examples, from the experimental sections below and by means of the drawings.

FIG. 1 is a graph showing relative metabolite concentration changes compared to the control (positive value) or to the treated animals (negative values) after asphyxia (orange, Start of Asphyxia (SA) vs End of Asphyxia (EA) and following the resuscitation (end of rescuscitation ER) procedure (green, EA vs ER) for the selected set of acyl carnitine derivatives. * denotes significance levels after correction for test multiplicity: q value lower than $10^{-3}$,  $10^{-5}$ and * $10^{-7}$;

FIG. 2 is a graph showing relative metabolite concentration changes compared to the control (positive value) or to the treated animals (negative values) after asphyxia (orange, SA vs EA) and following the resuscitation procedure (green, EA vs ER) for the selected set of metabolites other than acyl carnitine derivatives. * denotes significance levels after correction for test multiplicity: q value lower than $10^{-3}$,  $10^{-5}$ and * $10^{-7}$;

FIG. 3 is a graph showing relative metabolite concentration changes compared to the control (positive value) or to the treated animals (negative values) after asphyxia (orange, SA vs EA) and following the resuscitation procedure (green, EA vs ER) for a selection of concentration ratios between biologically connected metabolite. * denotes significance levels after correction for test multiplicity: q value lower than $10^{-3}$,  $10^{-5}$ and * $10^{-7}$;

FIG. 6 shows a graph demonstrating that metabolites can be used to determine the time of hypoxia and therefore reoxygenation: actual versus fitted hypoxia length (in minutes, log scale) for 26 animals from regression models involving commonly used marker lactate (black circles), Gly/BCAA ratio (red triangles) and a combination of three metabolomics parameters (green squares).

FIG. 7a shows the effect of a resuscitation protocol with the metabolite decadienyi-L-carnitine; and FIG. 7b shows the effect of a resuscitation protocol with the metabolite propionyl-L-carnitine.

DETAILED DESCRIPTION OF INVENTION

Figure 4:
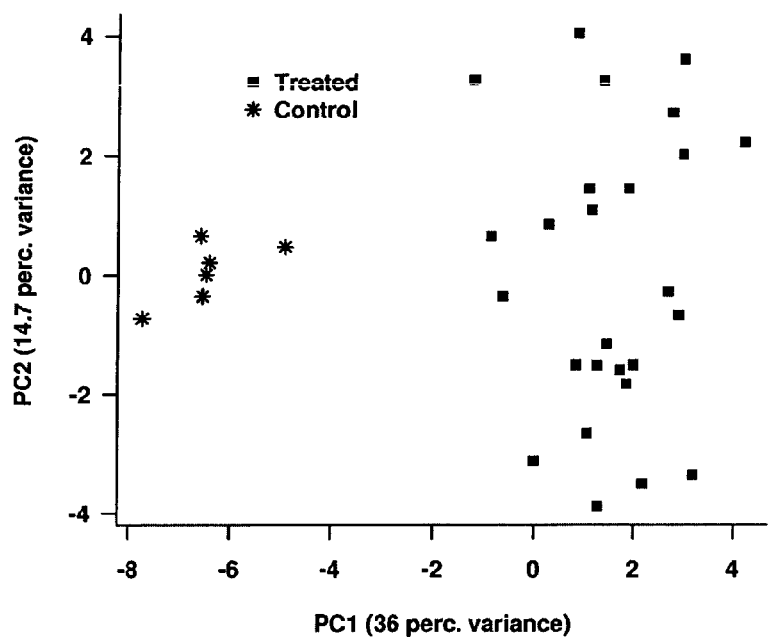
FIG. 4a shows a mapping of the samples (scores) on the first two dimensions from a principal component analysis using the full list of compounds given in table 1. This illustrates that the main source of variability in the metabolomics data is clearly related to the asphyxia effect.
FIG. 4b shows a mapping of the samples (scores) on the first two dimensions from a principal component analysis after removing the 30 top ranked metabolites from the list given in table 2. This illustrates that variance associated to the linear combination of the most prominent metabolites is necessary to early detection of asphyxia in the subject. This statement is confirmed by means of multivariate classification (see also FIG. 4c)
FIG. 4c shows an evaluation of classification performance by mean of repeated bootstrapping using Random Forest with different number of top ranked compounds/metabolites (analytes) excluded from the model. Exclusion of the top ranked metabolites is translated by a dramatic loss of classification efficiency and an increased variance of its error estimates.

Abbreviations: C4=Butyrylcarnitine/Isobutyrylcarnitine; BCAA=branched chain amino acids; Gly=Glycine "Asphyxia" in this context relates to any diseased state linked to lack of oxygen, oxygen saturation, hypoxia. Asphyxia can be induced either pre-/perinatally due to a lack of oxygen supply by the umbilical cord or can be caused by any condition associated with an inability to breathe and/or inadequate lung ventilation like choking, drowning, electric shock, injury, or the inhalation of toxic gases.

As used herein, the term "asphyxia specific metabolite" refers to a metabolite that is differentially present or differentially concentrated in asphyctic organisms compared to non-asphyctic organisms. For example, in some embodiments, asphyxia specific metabolites are present in asphyctic tissues but not in non-in asphyctic tissues.

In other embodiments, asphyxia-specific metabolites are absent in asphyctic tissues but present in non-asphyctic cells, tissues, body liquids. In still further embodiments, asphyxia specific metabolites are present at different levels (e.g., higher or lower) in asphyctic tissue/cells as compared to non-asphyctic cells. For example, an asphyxia specific metabolite may be differentially present at any level, but is generally present at a level that is increased by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more; or is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent).

An asphyxia-specific metabolite is preferably differentially present at a level that is statistically significant (e.g., a p-value less than 0.001 and/or a q-value of less than 0.01 as determined using either Analysis of Variance, Welch's t-test or its non parametric equivalent versions). Exemplary asphyxia-specific metabolites are described in the detailed description and experimental sections below.

The term "sample" in the present specification and claims is used in its broadest sense. On the one hand it is meant to include a specimen or culture. On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, rodents, etc. A biological sample may contain any biological material suitable for detecting the desired biomarkers, and may comprise cellular and/or non-cellular material from a subject. The sample can be isolated from any suitable biological tissue or fluid such as, for example, tissue, blood, blood plasma, urine, or cerebral spinal fluid (CSF).

A "reference level" of a metabolite means a level of the metabolite that is indicative of a particular disease state, phenotype, or lack thereof, as well as combinations of disease states, phenotypes, or lack thereof. A "positive" reference level of a metabolite means a level that is indicative of a particular disease state or phenotype. A "negative" reference level of a metabolite means a level that is indicative of a lack of a particular disease state or phenotype. For example, an "asphyxia-positive reference level" of a metabolite means a level of a metabolite that is indicative of a positive diagnosis of asphyxia in a subject, and an "asphyxia-negative reference level" of a metabolite means a level of a metabolite that is indicative of a negative diagnosis of asphyxia in a subject. A "reference level" of a metabolite may be an absolute or relative amount or concentration of the metabolite, a presence or absence of the metabolite, a range of amount or concentration of the metabolite, a minimum and/or maximum amount or concentration of the metabolite, a mean amount or concentration of the metabolite, and/or a median amount or concentration of the metabolite; and, in addition, "reference levels" of combinations of metabolites may also be ratios of absolute or relative amounts or concentrations of two or more metabolites with respect to each other or a composed value/score obtained by classification.

Appropriate positive and negative reference levels of metabolites for a particular disease state, phenotype, or lack thereof may be determined by measuring levels of desired metabolites in one or more appropriate subjects, and such reference levels may be tailored to specific populations of subjects (e.g., a reference level may be age-matched so that comparisons may be made between metabolite levels in samples from subjects of a certain age and reference levels for a particular disease state, phenotype, or lack thereof in a certain age group). Such reference levels may also be tailored to specific techniques that are used to measure levels of metabolites in biological samples (e.g., LC-MS, GC-MS, etc.), where the levels of metabolites may differ based on the specific technique that is used As used herein, the term "cell" refers to any eukaryotic or prokaryotic cell (e.g., bacterial cells such as $E.\ coli$, yeast cells, mammalian cells, avian cells, amphibian cells, plant cells, fish cells, and insect cells), whether located in vitro or in vivo.

As used herein, the term "processor" refers to a device that performs a set of steps according to a program (e.g., a digital computer). Processors, for example, include Central Processing Units ("CPUs"), electronic devices, or systems for receiving, transmitting, storing and/or manipulating data under programmed control.

As used herein, the term "memory device," or "computer memory" refers to any data storage device that is readable by a computer, including, but not limited to, random access memory, hard disks, magnetic (floppy) disks, compact discs, DVDs, magnetic tape, flash memory, and the like.

"Mass Spectrometry" (MS) is a technique for measuring and analyzing molecules that involves fragmenting a target molecule, then analyzing the fragments, based on their mass/charge ratios, to produce a mass spectrum that serves as a "molecular fingerprint". Determining the mass/charge ratio of an object is done through means of determining the wavelengths at which electromagnetic energy is absorbed by that object. There are several commonly used methods to determine the mass to charge ration of an ion, some measuring the interaction of the ion trajectory with electromagnetic waves, others measuring the time an ion takes to travel a given distance, or a combination of both. The data from these fragment mass measurements can be searched against databases to obtain definitive identifications of target molecules. Mass spectrometry is also widely used in other areas of chemistry, like petrochemistry or pharmaceutical quality control, among many others.

As used here, the term "metabolite" denotes endogenous organic compounds of a cell, an organism, a tissue or being present in body liquids and in extracts obtained from the aforementioned sources with a molecular weight typically below 1500 Dalton. Typical examples of metabolites are carbohydrates, lipids, phospholipids, sphingolipids and sphingophospholipids, amino acids, cholesterol, steroid hormones and oxidized sterols and other compounds such as collected in the Human Metabolite database [Wishart D S et al., *HMDB: the Human Metabolome Database. Nucleic Acids Res.* 2007 January; 35(Database issue):D521-6(see http://www.hmdb.ca/)] and other databases and literature. This includes any substance produced by metabolism or by a metabolic process and any substance involved in metabolism.

"Metabolomics" as understood within the scope of the present invention designates the comprehensive quantitative measurement of several (2-thousands) metabolites by, but not limited to, methods such as mass spectroscopy, coupling of liquid chromatography, gas chromatography and other separation methods chromatography with mass spectroscopy.

The term "separation" refers to separating a complex mixture into its component proteins or metabolites. Common laboratory separation techniques include gel electrophoresis and chromatography.

The term "capillary electrophoresis" refers to an automated analytical technique that separates molecules in a solution by applying voltage across buffer-filled capillaries. Capillary electrophoresis is generally used for separating ions, which move at different speeds when the voltage is applied, depending upon the size and charge of the ions. The solutes (ions) are seen as peaks as they pass through a detector and the area of each peak is proportional to the concentration of ions in the solute, which allows quantitative determinations of the ions.

The term "chromatography" refers to a physical method of separation in which the components to be separated are distributed between two phases, one of which is stationary (stationary phase) while the other (the mobile phase) moves in a definite direction. Chromatographic output data may be used for manipulation by the present invention.

An "ion" is a charged object formed by adding electrons to or removing electrons from an atom.

A "mass spectrum" is a plot of data produced by a mass spectrometer, typically containing m/z values on x-axis and intensity values on y-axis.

A "peak" is a point on a mass spectrum with a relatively high y-value.

The term "m/z" refers to the dimensionless quantity formed by dividing the mass number of an ion by its charge number. It has long been called the "mass-to-charge" ratio.

The term "metabolism" refers to the chemical changes that occur within the tissues of an organism, including "anabolism" and "catabolism". Anabolism refers to biosynthesis or the buildup of molecules and catabolism refers to the breakdown of molecules.

As used herein, the term "post-surgical tissue" refers to tissue that has been removed from a subject during a surgical procedure. Examples include, but are not limited to, biopsy samples, excised organs, and excised portions of organs.

As used herein, the terms "detect", "detecting", or "detection" may describe either the general act of discovering or discerning or the specific observation of a detectably labeled composition.

As used herein, the term "clinical failure" refers to a negative outcome following asphyxia treatment.

A biomarker in this context is a characteristic, comprising data of at least one metabolite that is measured and evaluated as an indicator of biologic processes, pathogenic processes, or responses to a therapeutic intervention associated with asphyxia or related to asphyxia treatment. A combined biomarker as used here may be selected from at least two small endogenous molecules and metabolites.

DETAILED DESCRIPTION OF THE INVENTION

The present invention relates to markers of Asphyxia and its duration/severity as well of the effect of therapeutic interventions. In particular embodiments, the present invention provides metabolites that are differentially present in Asphyxia. Experiments conducted during the course of development of embodiments of the present invention identified a series of metabolites as being differentially present in asphyxia versus normal.

Table 2 provides additional metabolites present in plasma serum or other body liquids. The disclosed markers find use as diagnostic and therapeutic targets.

Diagnostic Applications

In some embodiments, the present invention provides methods and compositions for diagnosing asphyxiac, including but not limited to, characterizing risk of asphyxia, stage of asphyxia, duration and severity etc. based on the presence of asphyxia specific metabolites or their derivates, precursors, metabolites, etc. Exemplary diagnostic methods are described below.

Thus, for example, a method of diagnosing (or aiding in diagnosing) whether a subject has asphyxia comprises (1) detecting the presence or absence or a differential level of one or more asphyxia specific metabolites selected from table 2 and b) diagnosing asphyxia based on the presence, absence or differential level of the asphyxia specific metabolite. When such a method is used to aid in the diagnosis of asphyxia, the results of the method may be used along with other methods (or the results thereof) useful in the clinical determination of whether a subject has asphyxia.

Any mammalian sample suspected of containing asphyxia specific metabolites is tested according to the methods described herein. By way of non-limiting examples, the sample may be tissue (e.g., a biopsy sample or post-surgical tissue), blood, urine, or a fraction thereof (e.g., plasma, serum, urine supernatant, urine cell pellet).

In some embodiments, the patient sample undergoes preliminary processing designed to isolate or enrich the sample for asphyxia specific metabolites or cells that contain asphyxia specific metabolites. A variety of techniques known to those of ordinary skill in the art may be used for this purpose, including but not limited: centrifugation; immunocapture; and cell lysis.

Metabolites may be detected using any suitable method including, but not limited to, liquid and gas phase chromatography, alone or coupled to mass spectrometry (See e.g., experimental section below), NMR, immunoassays, chemical assays, spectroscopy and the like. In some embodiments, commercial systems for chromatography and NMR analysis are utilized.

In other embodiments, metabolites (i.e. biomarkers and derivatives thereof) are detected using optical imaging techniques such as magnetic resonance spectroscopy (MRS), magnetic resonance imaging (MRI), CAT scans, ultra sound, MS-based tissue imaging or X-ray detection methods (e.g., energy dispersive x-ray fluorescence detection).

Any suitable method may be used to analyze the biological sample in order to determine the presence, absence or level(s) of the one or more metabolites in the sample. Suitable methods include chromatography (e.g., HPLC, gas chromatography, liquid chromatography), mass spectrometry (e.g., MS, MS-MS), enzyme-linked immunosorbent assay (ELISA), antibody linkage, other immunochemical techniques, biochemical or enzymatic reactions or assays, and combinations thereof. Further, the level(s) of the one or more metabolites may be measured indirectly, for example, by using an assay that measures the level of a compound (or compounds) that correlates with the level the biomarker(s) that are desired to be measured.

The levels of one or more of the recited metabolites may be determined in the methods of the present invention. For example, the level(s) of one metabolites, two or more metabolites, three or more metabolites, four or more metabolites, five or more metabolites, six or more metabolites, seven or more metabolites, eight or more metabolites, nine or more metabolites, ten or more metabolites, etc., including a combination of some or all of the metabolites including, but not limited to those listed in table 2, may be determined and used in such methods.

Determining levels of combinations of the metabolites may allow greater sensitivity and specificity in the methods, such as diagnosing asphyxia and aiding in the diagnosis of asphyxia, and may allow better differentiation or characterization of asphyxia from other courses of brain injuries or other asphyxias that may have similar or overlapping metabolites to asphyxia (as compared to a subject not having asphyxia). For example, ratios of the levels of certain metabolites in biological samples may allow greater sensitivity and specificity in diagnosing asphyxia and aiding in the diagnosis of asphyxia and allow better differentiation or characterization of asphyxia from other asphyxias or other disorders of the that may have similar or overlapping metabolites to asphyxia (as compared to a subject not having asphyxia).

Data Analysis

In some embodiments, a computer-based analysis program is used to translate the raw data generated by the detection assay (e.g., the presence, absence, or amount of an asphyxia specific metabolite) into data of predictive value for a clinician. The clinician can access the predictive data using any suitable means. Thus, in some embodiments, the present invention provides the further benefit that the clinician, who is not likely to be trained in metabolite analysis, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a blood, urine or serum sample) is obtained from a subject and submitted to a profiling service (e.g., clinical lab at a medical facility, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a plasma sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., metabolic profile), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of asphyxia being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis.

The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

When the amount(s) or level(s) of the one or more metabolites in the sample are determined, the amount(s) or level(s) may be compared to asphyxia metabolite-reference levels, such as -asphyxia-positive and/or asphyxia-negative reference levels to aid in diagnosing or to diagnose whether the subject has asphyxia. Levels of the one or more metabolites in a sample corresponding to the asphyxia-positive reference levels (e.g., levels that are the same as the reference levels, substantially the same as the reference levels, above and/or below the minimum and/or maximum of the reference levels, and/or within the range of the reference levels) are indicative of a diagnosis of asphyxia in the subject. Levels of the one or more metabolites in a sample corresponding to the asphyxia-negative reference levels (e.g., levels that are the same as the reference levels, substantially the same as the reference levels, above and/or below the minimum and/or maximum of the reference levels, and/or within the range of the reference levels) are indicative of a diagnosis of no asphyxia in the subject. In addition, levels of the one or more metabolites that are differentially present (especially at a level that is statistically significant) in the sample as compared to asphyxia-negative reference levels are indicative of a diagnosis of asphyxia in the subject. Levels of the one or more metabolites that are differentially present (especially at a level that is statistically significant) in the sample as compared to asphyxia-positive reference levels are indicative of a diagnosis of no asphyxia in the subject.

The level(s) of the one or more metabolites may be compared to asphyxia-positive and/or asphyxia-negative reference levels using various techniques, including a simple comparison (e.g., a manual comparison) of the level(s) of the one or more metabolites in the biological sample to asphyxia-positive and/or asphyxia-negative reference levels. The level(s) of the one or more metabolites in the biological sample may also be compared to asphyxia-positive and/or asphyxia-negative reference levels using one or more statistical analyses (e.g., t-test, Welch's t-test, Wilcoxon's rank sum test, random forests).

Compositions for use (e.g., sufficient for, necessary for, or useful for) in the diagnostic methods of some embodiments of the present invention include reagents for detecting the presence or absence of asphyxia specific metabolites. Any of these compositions, alone or in combination with other compositions of the present invention, may be provided in the form of a kit. Kits may further comprise appropriate controls and/or detection reagents.

Embodiments of the present invention provide for multiplex or panel assays that simultaneously detect one or more of the markers of the present invention depicted in table 2, alone or in combination with additional asphyxia markers known in the art. For example, in some embodiments, panel or combination assays are provided that detected 2 or more, 3 or more, 4 or more, 5 or more, 6 or more, 7 or more, 8 or more, 9 or more, 10 or more, 15 or more, or 20 or more, 30 or more, 40 or more markers in a single assay. In some embodiments, assays are automated or high throughput.

A preferred embodiment of the present invention is the use of markers listed in table 2 for diagnosis of asphyxia and its duration/severity where said mammalian subject is a human being, said biological sample blood and/or blood cells.

In some embodiments, additional asphyxia markers are included in multiplex or panel assays. Markers are selected for their predictive value alone or in combination with the metabolic markers described herein.

II. Therapeutic Methods

In some embodiments, the present invention provides therapeutic methods (e.g., that target the asphyxia specific metabolites described herein). In some embodiments, the therapeutic methods target enzymes or pathway components of the asphyxia specific metabolites described herein.

For example, in some embodiments, the present invention provides compounds that target the asphyxia specific metabolites of the present invention. The compounds may decrease the level of asphyxia specific metabolite by, for example, interfering with synthesis of the asphyxia specific metabolite (e.g., by blocking transcription or translation of an enzyme involved in the synthesis of a metabolite, by inactivating an enzyme involved in the synthesis of a metabolite (e.g., by post translational modification or binding to an irreversible inhibitor), or by otherwise inhibiting the activity of an enzyme involved in the synthesis of a metabolite) or a precursor or metabolite thereof, by binding to and inhibiting the function of the asphyxia specific metabolite, by binding to the target of the asphyxia specific metabolite (e.g., competitive or non competitive inhibitor), or by increasing the rate of break down or clearance of the metabolite.

The compounds may increase the level of asphyxia specific metabolite by, for example, inhibiting the break down or clearance of the asphyxia specific metabolite (e.g., by inhibiting an enzyme involved in the breakdown of the metabolite), by increasing the level of a precursor of the asphyxia specific metabolite, or by increasing the affinity of the metabolite for its target.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates.

In some embodiments, the present invention provides drug screening assays (e.g., to screen for anti-asphyxia drugs). The screening methods of the present invention utilize asphyxia specific metabolites described herein. As described above, in some embodiments, test compounds are small molecules, nucleic acids, or antibodies. In some embodiments, test compounds target asphyxia specific metabolites directly. In other embodiments, they target enzymes involved in metabolic pathways of asphyxia specific metabolites.

EXPERIMENTAL

The following examples are provided in order to demonstrate and further illustrate certain preferred embodiments and aspects of the present invention and are not to be construed as limiting the scope thereof.

General Analytics:

Sample preparation and metabolomic analyses were performed at BIOCRATES life sciences AG, Innsbruck, Austria. We used a multi-parametric, highly robust, sensitive and high-throughput targeted metabolomic platform consisting of flow injection analysis (FIA)-MS/MS and LC-MS/MS methods for the simultaneous quantification of a broad range of endogenous intermediates namely acylcarnitines, sphingomyelins, hexoses, glycerophospholipids, amino acids, biogenic amines, bile acids, eicosanoids, and small organic acids (energy metabolism), in plasma and brain samples. All procedures (sample handling, analytics) were performed by co-workers blinded to the groups.

Brain Homogenization

Brain samples were thawed on ice for 1 hour and homogenates were prepared by adding phosphate-buffer (phosphate buffered saline, 0.1 µmol/L; Sigma Aldrich, Vienna, Austria) to tissue sample, ratio 3:1 (w/v), followed by homogenization with a Potter S homogeniser (Sartorius, Goettingen, Germany) at 9 g on ice for 1 minute. To enable analysis of all samples simultaneously within one batch, samples were frozen again (−70° C.), thawed on ice (1 h) on the day of analysis and centrifuged at 18000 g at 2° C. for 5 min. All tubes were prepared with 0.001% BHT (butylated hydroxytoluene; Sigma-Aldrich, Vienna, Austria) to prevent artificial formation of prostaglandins caused by autooxidation Acylcarnitines, Sphingomyelins, Hexoses, Glycerophospholipids (FIA-MS/MS)

To determine the concentration of acylcarnitines, sphingomyelins and glycerophospholipids in brain homogenates and in plasma the Absolute/DQ kit p150 (Biocrates Life Sciences AG) was prepared as described in the manufacturer's protocol. In brief, 10 μL of brain homogenate was added to the center of the filter on the upper 96-well kit plate, and the samples were dried using a nitrogen evaporator (VLM Laboratories). Subsequently, 20 μL of a 5% solution of phenyl-isothiocyanate was added for derivatization. After incubation, the filter spots were dried again using an evaporator. The metabolites were extracted using 300 μL of a 5 mM ammonium acetate solution in methanol. The extracts were obtained by centrifugation into the lower 96-deep well plate followed by a dilution step with 600 μL of kit MS running solvent. Mass spectrometric analysis was performed on an API4000 QTrap® tandem mass spectrometry instrument (Applied Biosystems/MDS Analytical Technologies) equipped with an electro-spray ionization (ESI)-source using the analysis acquisition method as provided in the Absolute/DQ kit. The standard FIA-MS/MS method was applied for all measurements with two subsequent 20 μL injections (one for positive and one for negative mode analysis). Multiple reaction monitoring (MRM) detection was used for quantification applying the spectra parsing algorithm integrated into the MetIQ software (Biocrates Life Sciences AG). Concentration values for 148 metabolites (all analytes determined with the metabolomics kit besides of the amino acids, which were determined by a different method) obtained by internal calibration were exported for comprehensive statistical analysis.

Amino Acids, Biogenic Amines (LC-MS/MS)

Amino acids and biogenic amines were quantitatively analyzed by reversed phase LC-MS/MS to obtain chromatographic separation of isobaric (same MRM ion pairs) metabolites for individual quantitation performed by external calibration and by use of internal standards. 10 μL sample volume (plasma, brain homogenate) is required for the analysis using the following sample preparation procedure. Samples were added on filter spots placed in a 96-solvinert well plate (internal standards were placed and dried down under nitrogen before), fixed above a 96 deep well plate (capture plate). 20 μL of 5% phenyl-isothiocyanate derivatization reagent was added. The derivatized samples were extracted after incubation by aqueous methanol into the capture plate. Sample extracts were analyzed by LC-ESI-MS/MS in positive MRM detection mode with an API4000 QTrap® tandem mass spectrometry instrument (Applied Biosystems/MDS Analytical Technologies). The analyzed individual metabolite concentrations (Analyst 1.4.2 software, Applied Biosystems) were exported for comprehensive statistical analysis.

Bile Acids (LC-MS/MS)

A highly selective reversed phase LC-MS/MS analysis method in negative MRM detection mode was applied to determine the concentration of bile acids in plasma samples. Samples were extracted via dried filter spot technique in 96 well plate format, which is well suitable for high throughput analysis. For highly accurate quantitation internal standards and external calibration were applied. In brief, internal standards and 20 μL sample volume placed onto filter spots were extracted and simultaneously protein precipitated with aqueous methanol. These sample extracts were measured by LC-ESI-MS/MS with an API4000 QTrap® tandem mass spectrometry instrument (Applied Biosystems/MDS Analytical Technologies). Data of bile acids were quantified with Analyst 1.4.2 software (Applied Biosystems) and finally exported for comprehensive statistical analysis.

Prostanoids, Oxidized Fatty Acids (LC-MS/MS)

Prostanoids—a term summarizing prostaglandins (PG), thromboxanes (TX) and prostacylines—and oxidised fatty acid metabolites were analyzed in plasma extracts by LC-ESI-MS/MS [*Unterwurzacher at al. Clin Chem Lab Med* 2008; 46 (11):1589-1597] and in brain homogenate extracts by online solid phase extraction (SPE)-LC-MS/MS [Unterwurzacher et al. *Rapid Commun Mass Spec submitted*] with an API4000 QTrap®tandem mass spectrometry instrument (Applied Biosystems/MDS Analytical Technologies) in negative MRM detection mode. The sample preparation was the same for both, plasma and brain homogenates. In brief, filter spots in a 96 well plate were spiked with internal standard; 20 μL of plasma or tissue homogenates were added and extracted with aqueous methanol, the individual extracts then were analysed. Data of prostanoids and oxidized fatty acids were quantified with Analyst 1.4.2 software (Applied Biosystems) and finally exported for statistical analysis.

Energy Metabolism (Organic Acids) (LC-MS/MS)

For the quantitative analysis of energy metabolism intermediates (glycolysis, citrate cycle, pentose phosphate pathway, urea cycle) hdyrophilic interaction liquid chromatography (HILIC)-ESI-MS/MS method in highly selective negative MRM detection mode was used. The MRM detection was performed using an API4000 QTrap® tandem mass spectrometry instrument (Applied Biosystems/MDS Analytical Technologies). 20 μL sample volume (plasma, brain homogenate) was protein precipitated and extracted simultaneously with aqueous methanol in a 96 well plate format. Internal standards (ratio external to internal standard) and external calibration were used for highly accurate quantitation. Data were quantified with Analyst 1.4.2 software (Applied Biosystems) and finally exported for statistical analysis.

TABLE 1a

Common and Systematic Name of Compounds

| BC Code | Common Name | Systematic Name |
| --- | --- | --- |
| Suc.EM | Succinic acid (succinate) | Butanedioic acid |
| Lac.EM | Lactate | Propanoic acid, 2-hydroxy- |
| C4.K1 | Butyrylcarnitine/Isobutyrylcarnitine | 3-butanoyloxy-4-trimethylammonio-butanoate (L) |
| Fum.EM | Fumaric acid | 2-Butenedioic acid (E)-N- |

TABLE 1a-continued

Common and Systematic Name of Compounds

| BC Code | Common Name | Systematic Name |
|---|---|---|
| GCA.BA | Glycocholic Acid | (3-alpha,7-alpha,12-alpha-Trihydroxycholan-24-oyl)glycine |
| C16:2.K1 | Hexadecadienoylcarnitine | chain length and number of double bonds is determined by the measured mass, but position and cis-trans-isomerie of double bonds is not specified (generally double bonds are cis) |
| Putrescine.K2 | Putrescine | Putrescine (1,4-Butanediamine) |

Glu/Gln

| BC Code | Common Name | Systematic Name |
|---|---|---|
| C16:1.K1 | Hexadecenoylcarnitine [Palmitoleylcarnitine] | chain length and number of double bonds is determined by the measured mass, but position and cis-trans-isomerie of double bonds is not specified (generally double bonds are cis) |
| C10:2.K1 | Decadienoylcarnitine | chain length and number of double bonds is determined by the measured mass, but position and cis-trans-isomerie of double bonds is not specified (generally double bonds are cis) |
| TCDCA.BA | Taurochenodeoxycholic Acid | Ethanesulfonic acid, 2-(((3alpha,5beta,7alpha)-3,7-dihydroxy-24-oxocholan-24-yl)amino)- |
| GCDCA.BA | Glycochenodeoxycholic Acid | Glycine, N-((3alpha,5beta,7alpha)-3,7-dihydroxy-24-oxocholan-24-yl)- |
| Spermidine.K2 | Spermidine | 1,4-Butanediamine, N-(3-aminopropyl)- |
| C18:2.K1 | Octadecadienoylcarnitine [Linoleylcarnitine] | chain length and number of double bonds is determined by the measured mass, but position and (Z)-(E)-isomerie of double bonds is not specified |
| CA.BA | Cholic Acid | Cholan-24-oic acid, 3,7,12-trihydroxy-, (3alpha,5beta,7alpha,12alpha)- |
| C5.K1 | Isovalerylcarnitine/2-Methylbutyrylcarnitine/Valerylcarnitine | 3 C5-fatty acids with the same mass as residues (branched/unbranched) |
| Spermine.K2 | Spermine | 1,4-Butanediamine, N,N'-bis(3-aminopropy1)- |
| Pyr + OAA.EM | Pyruvate + Oxaloacetate | |
| C5:1-DC.K1 | Tiglylcarnitine/3-Methyl-crotonylcarnitine | 2 C5 fatty acids with one double bond as residues |
| C3.K1 | Propionylcarnitine | Propionylcarnitine |
| Lys.K2 | Lysine | L-Lysine |
| alpha-KGA.EM | alpha-Ketoglutaric acid | Pentanedioic acid, 2-oxo- |
| C18:1.K1 | Octadecenoylcarnitine [Oleylcarnitine] | chain length and number of double bonds is determined by the measured mass, but position and cis-trans-isomerie of double bonds is not specified (generally double bonds are cis) |
| C14:2.K1 | Tetradecadienoylcarnitine | chain length and number of double bonds is determined by the measured mass, but position and cis-trans-isomerie of double bonds is not specified (generally double bonds are cis) |

Asp/Asn
Putrescine/Orn

| BC Code | Common Name | Systematic Name |
|---|---|---|
| Gln.K2 | Glutamine | L-Glutamine |
| UDCA.BA | Ursodeoxycholic Acid | Cholan-24-oic acid, 3,7-dihydroxy-, (3alpha,5beta,7beta)- |
| PC ae C40:3.K1 | | Glycerophosphocholine with estimated chemical composition (2 residues) |
| Serotonin.K2 | Serotonin | Indol-5-ol, 3-(2-aminoethyl)- |

Orn/Cit

| BC Code | Common Name | Systematic Name |
|---|---|---|
| Ala.K2 | Alanine | L-Alanine |
| C14.K1 | Tetradecanoylcarnitine | requirement: unbranched fatty acid: only Myristic acid (CAS-Nr: 544-63-8) is possible |

Ala/BCAA

| BC Code | Common Name | Systematic Name |
|---|---|---|
| His.K2 | Histidine | L-Histidine |
| lysoPC a C16:0.K1 | | Glycerophosphocholine with estimated chemical composition (1 acyl residue) |
| lysoPC a C17:0.K1 | | Glycerophosphocholine with estimated chemical composition (1 acyl residue) |

TABLE 1a-continued

Common and Systematic Name of Compounds

| BC Code | Common Name | Systematic Name |
|---|---|---|
| C12.K1 | Dodecanoylcarnitine [Laurylcarnitine] | requirement: unbranched fatty acid: only Lauric acid (CAS-Nr: 143-07-7) is possible |
| Pro.K2 | Proline | L-Proline |
| Serotonin/Trp | Serotonin/Trytophan | |
| C14:2-OH.K1 | 3-Hydroxytetradecadienoylcarnitine | chain length and number of double bonds is determined by the measured mass, but positionof the OH-group and position and cis-trans-isomerie of double bonds is not specified |
| Glu.K2 | Glutamate | L-Glutamic acid |
| C16:2-OH.K1 | 3-Hydroxyhexadecadienoylcarnitine | chain length and number of double bonds is determined by the measured mass, but positionof the OH-group and position and cis-trans-isomerie of double bonds is not specified |
| Histamine.K2 | Histamine | 2-Imidazol-4-ethylamine |
| PC ae C30:0.K1 | | Glycerophosphocholine with estimated chemical composition (2 residues) |
| C14:1.K1 | Tetradecenoylcarnitine [Myristoleylcarnitine] | chain length and number of double bonds is determined by the measured mass, but position and cis-trans-isomerie of double bonds is not specified (generally double bonds are cis) |
| SumLyso | | |
| Phe.K2 | Phenylalanine | L-Phenylalanine |
| lysoPC a C18:0.K1 | | Glycerophosphocholine with estimated chemical composition (1 acyl residue) |
| PC aa C42:4.K1 | | Glycerophosphocholine with estimated chemical composition (2 acyl residues) |
| PC ae C38:4.K1 | | Glycerophosphocholine with estimated chemical composition (2 residues) |
| PC aa C40:3.K1 | | Glycerophosphocholine with estimated chemical composition (2 acyl residues) |
| AA.PA | Arachidonic acid | 5,8,11,14-Eicosatetraenoic acid, (all-Z)- |
| C5:1.K1 | Tiglylcarnitine/3-Methyl-crotonylcarnitine | 2 C5 fatty acids with one double bond as residues |
| Met-SO.K2 | Methionine-Sulfoxide | Butyric acid, 2-amino-4-(methylsulfinyl)- |
| Spermine/Spermidine | | |
| C16 + C18/C0 | | |
| C16.K1 | Hexadecanoylcarnitine [Palmitoylcarnitine] | Palmitylcarnitine (requirement: unbranched fatty acid) |
| lysoPC a C16:1.K1 | | Glycerophosphocholine with estimated chemical composition (1 acyl residue) |
| PC aa C40:4.K1 | | Glycerophosphocholine with estimated chemical composition (2 acyl residues) |
| Asn.K2 | Asparagine | L-Asparagine |
| C9.K1 | Nonanoylcarnitine [Pelargonylcarnitine] | Nonanoylcarnitine (requirement: unbranched fatty acid) |
| PC ae C42:5.K1 | | Glycerophosphocholine with estimated chemical composition (2 residues) |
| C6 (C4:1-DC).K1 | Hexanoylcarnitine [Caproylcarnitine] | mass of possible residues: Caproic acid and Fumaric acid ist similar (116.1) |
| PC aa C40:6.K1 | | Glycerophosphocholine with estimated chemical composition (2 acyl residues) |
| Val.K2 | Valine | L-Valine |
| SumSFA | | |
| PC ae C40:5.K1 | | Glycerophosphocholine with estimated chemical composition (2 residues) |
| PC ae C42:4.K1 | | Glycerophosphocholine with estimated chemical composition (2 residues) |
| PC ae C40:6.K1 | | Glycerophosphocholine with estimated chemical composition (2 residues) |
| Leu.K2 | Leucine | L-Leucine |
| C2.K1 | Acetylcarnitine | 1-Propanaminium, 2-(acetyloxy)-3-carboxy-N,N,N-trimethyl-, inner salt |
| PC aa C40:5.K1 | | Glycerophosphocholine with estimated chemical composition (2 acyl residues) |
| PC ae C42:3.K1 | | Glycerophosphocholine with estimated chemical composition (2 residues) |
| PC ae C40:4.K1 | | Glycerophosphocholine with estimated chemical composition (2 residues) |
| Asp.EM | Aspartic acid | L-Aspartic acid |

TABLE 1a-continued

Common and Systematic Name of Compounds

| BC Code | Common Name | Systematic Name |
|---|---|---|
| CDCA.BA | Chenodeoxycholic Acid | Cholan-24-oic acid, 3,7-dihydroxy-, (3alpha,5beta,7alpha)- |
| PC aa C38:6.K1 | | Glycerophosphocholine with estimated chemical composition (2 acyl residues) |
| SM (OH) C16:1.K1 | Hydroxysphingomyelin with acyl residue sum C16:1 | Hydroxysphingomyelin with estimated chemical composition |
| PC ae C38:5.K1 | | Glycerophosphocholine with estimated chemical composition (2 residues) |
| C18:1-OH.K1 | 3-Hydroxyoctadecenoylcarnitine [3-Hydroxyoleylcarnitine] | chain length and number of double bonds is determined by the measured mass, but positionof the OH-group and position and cis-trans-isomerie of double bond is not specified |

Orn/Arg

| | | |
|---|---|---|
| C16:1-OH.K1 | 3-Hydroxyhexadecenoylcarnitine [3-Hydroxypalmitoleylcarnitine] | chain length and number of double bonds is determined by the measured mass, but positionof the OH-group and position and cis-trans-isomerie of double bond is not specified |
| C18.K1 | Octadecanoylcarnitine [Stearylcarnitine] | Stearylcarnitine (requirement: unbranched fatty acid) |
| PC aa C36:6.K1 | | Glycerophosphocholine with estimated chemical composition (2 acyl residues) |
| SM C26:1.K1 | | Hydroxysphingomyelin with estimated chemical composition |
| PC aa C42:5.K1 | | Glycerophosphocholine with estimated chemical composition (2 acyl residues) |
| C14:1-OH.K1 | 3-Hydroxytetradecenoylcarnitine [3-Hydroxymyristoleylcarnitine] | chain length and number of double bonds is determined by the measured mass, but position and cis-trans-isomerie of double bonds is not specified (generally double bonds are cis) |
| PC aa C38:4.K1 | | Glycerophosphocholine with estimated chemical composition (2 acyl residues) |
| SumPC + Lyso | | |
| PC ae C36:4.K1 | | Glycerophosphocholine with estimated chemical composition (2 residues) |
| Hex.EM | Hexose | sum of aldohexoses and ketohexoses |
| LCA.BA | Lithocholic acid | Cholan-24-oic acid, 3-hydroxy-, (3alpha,5beta)- |
| PC aa C36:4.K1 | | Glycerophosphocholine with estimated chemical composition (2 residues) |
| SumPC | | |
| SumPUFA | | |
| PC aa C40:2.K1 | | Glycerophosphocholine with estimated chemical composition (2 acyl residues) |
| Met.K2 | Methionine | L-Methionine |
| PC ae C38:3.K1 | | Glycerophosphocholine with estimated chemical composition (2 residues) |
| PC ae C32:2.K1 | | Glycerophosphocholine with estimated chemical composition (2 residues) |
| Cit.K2 | Citrulline | L-Citrulline (L-Ornithine, N5-(aminocarbonyl)-) |
| PC ae C30:1.K1 | | Glycerophosphocholine with estimated chemical composition (2 residues) |
| PC ae C42:2.K1 | | Glycerophosphocholine with estimated chemical composition (2 residues) |

Kyn/Trp

| | | |
|---|---|---|
| Orn.K2 | Ornithine | L-Ornithine |
| PC ae C38:6.K1 | | Glycerophosphocholine with estimated chemical composition (2 residues) |
| lysoPC a C20:4.K1 | | Glycerophosphocholine with estimated chemical composition (1 acyl residue) |
| PC ae C40:1.K1 | | Glycerophosphocholine with estimated chemical composition (2 residues) |
| Asp.K2 | Aspartate | L-Aspartic acid |
| PC aa C30:2.K1 | | Glycerophosphocholine with estimated chemical composition (2 acyl residues) |
| PC aa C28:1.K1 | | Glycerophosphocholine with estimated chemical composition (2 acyl residues) |

TABLE 1a-continued

Common and Systematic Name of Compounds

| BC Code | Common Name | Systematic Name |
|---|---|---|
| Gly/BCAA | | |
| PC aa C38:5.K1 | | Glycerophosphocholine with estimated chemical composition (2 acyl residues) |
| PC ae C34:1.K1 | | Glycerophosphocholine with estimated chemical composition (2 residues) |
| PC aa C38:3.K1 | | Glycerophosphocholine with estimated chemical composition (2 acyl residues) |
| C16-OH.K1 | 3-Hydroxyhexadecanolycarnitine [3-Hydroxypalmitoylcarnitine] | chain length is determined by the measured mass, but position of the OH-group is not specified |
| SM (OH) C14:1.K1 | | Hydroxysphingomyelin with estimated chemical composition |
| PC ae C44:4.K1 | | Glycerophosphocholine with estimated chemical composition (2 residues) |
| PC ae C38:1.K1 | | Glycerophosphocholine with estimated chemical composition (2 residues) |
| SumSM | | |
| SumMUFA | | |
| PC ae C40:2.K1 | | Glycerophosphocholine with estimated chemical composition (2 residues) |
| lysoPC a C24:0.K1 | | Glycerophosphocholine with estimated chemical composition (1 acyl residue) |
| OH-Kyn.K2 | Hydroxykynurenine | 3-Hydroxykynurenine |
| SM (OH) C22:1.K1 | | Hydroxysphingomyelin with estimated chemical composition |
| PC ae C32:1.K1 | | Glycerophosphocholine with estimated chemical composition (2 residues) |
| SM C16:1.K1 | | chain length and number of double bonds is determined by the measured mass, but position and cis-trans-isomerie of double bonds is not specified (generally double bonds are cis) |
| PC ae C30:2.K1 | | Glycerophosphocholine with estimated chemical composition (2 residues) |
| Ala/Lys | | |
| Tyr.K2 | Tyrosine | L-Tyrosine |
| PC ae C34:0.K1 | | Glycerophosphocholine with estimated chemical composition (2 residues) |
| PC ae C36:0.K1 | | Glycerophosphocholine with estimated chemical composition (2 residues) |
| SM (OH) C22:2.K1 | | Hydroxysphingomyelin with estimated chemical composition |
| lysoPC a C28:0.K1 | | Glycerophosphocholine with estimated chemical composition (1 acyl residue) |
| C12:1.K1 | Dodecenoylcarnitine | chain length and number of double bonds is determined by the measured mass, but position and cis-trans-isomerie of double bonds is not specified (generally double bonds are cis) |
| PC aa C34:4.K1 | | Glycerophosphocholine with estimated chemical composition (2 acyl residues) |
| SM C26:0.K1 | sphingomyelin with acyl residue sum C26:0 | Sphingomyelin with estimated chemical composition |
| SM (OH) C24:1.K1 | Hydroxysphingomyelin with acyl residue sum C24:1 | Hydroxysphingomyelin with estimated chemical composition |
| SM C16:0.K1 | sphingomyelin with acyl residue sum C16:0 | Sphingomyelin with estimated chemical composition |
| Ile.K2 | Isoleucine | L-Isoleucine |
| C5-DC (C6-OH).K1 | | Acylcarnitine with estimated composition: mass of 2 possible residues is similar |
| PC aa C38:0.K1 | | Glycerophosphocholine with estimated chemical composition (2 acyl residues) |
| PC aa C34:2.K1 | | Glycerophosphocholine with estimated chemical composition (2 acyl residues) |
| Cit/Arg | | |
| Ser.K2 | Serine | L-Serine |
| PC ae C36:5.K1 | | Glycerophosphocholine with estimated chemical composition (2 residues) |
| PC ae C34:2.K1 | | Glycerophosphocholine with estimated chemical composition (2 residues) |

TABLE 1a-continued

Common and Systematic Name of Compounds

| BC Code | Common Name | Systematic Name |
|---|---|---|
| PC ae C36:3.K1 | | Glycerophosphocholine with estimated chemical composition (2 residues) |
| C3-OH.K1 | Hydroxypropionylcarnitine | chain length is determined by the measured mass, but position of the OH-group is not specified |
| PC ae C42:1.K1 | | Glycerophosphocholine with estimated chemical composition (2 residues) |
| H1.K1 | | sum of aldohexoses and ketohexoses |
| PC ae C36:2.K1 | | Glycerophosphocholine with estimated chemical composition (2 residues) |
| SM C22:3.K1 | sphingomyelin with acyl residue sum C22:3 | Sphingomyelin with estimated chemical composition |
| SM C24:1.K1 | sphingomyelin with acyl residue sum C24:1 | Sphingomyelin with estimated chemical composition |
| C4-OH (C3-DC).K1 | 3-Hydroxybutyrylcarnitine | Acylcarnitine with estimated composition: mass of 2 possible residues is similar |
| PC aa C40:1.K1 | | Glycerophosphocholine with estimated chemical composition (2 acyl residues) |
| PC aa C32:3.K1 | | Glycerophosphocholine with estimated chemical composition (2 acyl residues) |
| PC aa C42:1.K1 | | Glycerophosphocholine with estimated chemical composition (2 acyl residues) |
| PC aa C36:5.K1 | | Glycerophosphocholine with estimated chemical composition (2 acyl residues) |
| PC aa C42:6.K1 | | Glycerophosphocholine with estimated chemical composition (2 acyl residues) |
| DHA.PA | Docosahexaenoic acid | 4,7,10,13,16,19-Docosahexaenoic acid, (all-Z)- |
| SM C20:2.K1 | sphingomyelin with acyl residue sum C20:2 | Sphingomyelin with estimated chemical composition |
| C4:1.K1 | Butenoylcarnitine | chain length is determined by the measured mass, but position of the double bond is not specified |
| SM C24:0.K1 | sphingomyelin with acyl residue sum C24:0 | Sphingomyelin with estimated chemical composition |
| PC ae C38:0.K1 | | Glycerophosphocholine with estimated chemical composition (2 residues) |
| Kyn/OHKyn | | |
| Arg.K2 | Arginine | L-Arginine |
| total DMA.K2 | | |
| PC aa C34:3.K1 | | Glycerophosphocholine with estimated chemical composition (2 acyl residues) |
| PC ae C38:2.K1 | | Glycerophosphocholine with estimated chemical composition (2 residues) |
| PUFA/MUFA | | |
| PC aa C42:0.K1 | | Glycerophosphocholine with estimated chemical composition (2 acyl residues) |
| SM C18:1.K1 | | Sphingomyelin with estimated chemical composition |
| PC aa C32:2.K1 | | Glycerophosphocholine with estimated chemical composition (2 residues) |
| lysoPC a C18:2.K1 | | Glycerophosphocholine with estimated chemical composition (1 acyl residue) |
| PC ae C44:3.K1 | | Glycerophosphocholine with estimated chemical composition (2 residues) |
| PC ae C40:0.K1 | | Glycerophosphocholine with estimated chemical composition (2 residues) |
| Xle.K2 | Leucine + Isoleucine | |
| PC aa C24:0.K1 | | Glycerophosphocholine with estimated chemical composition (2 acyl residues) |
| PC aa C38:1.K1 | | Glycerophosphocholine with estimated chemical composition (2 acyl residues) |
| SM C18:0.K1 | | Sphingomyelin with estimated chemical composition |
| PC aa C42:2.K1 | | Glycerophosphocholine with estimated chemical composition (2 acyl residues) |
| lysoPC a C20:3.K1 | | Glycerophosphocholine with estimated chemical composition (1 acyl residue) |
| PC ae C36:1.K1 | | Glycerophosphocholine with estimated chemical composition (2 residues) |
| C3:1.K1 | Propenoylcarnitine | |
| lysoPC a C18:1.K1 | | Glycerophosphocholine with estimated chemical composition (1 acyl residue) |

TABLE 1a-continued

Common and Systematic Name of Compounds

| BC Code | Common Name | Systematic Name |
|---|---|---|
| C8:1.K1 | Octenoylcarnitine | chain length and number of double bonds is determined by the measured mass, but position and cis-trans-isomerie of double bonds is not specified (generally double bonds are cis) |
| C8.K1 | Octanoylcarnitine [Caprylylcarnitine] | |
| PC aa C30:0.K1 | | Glycerophosphocholine with estimated chemical composition (2 acyl residues) |
| PC ae C44:5.K1 | | Glycerophosphocholine with estimated chemical composition (2 residues) |
| lysoPC a C14:0.K1 | | Glycerophosphocholine with estimated chemical composition (1 acyl residue) |
| Creatinine.K2 | Creatinine | 4H-Imidazol-4-one, 2-amino-1,5-dihydro-1-methyl- |
| C0.K1 | Carnitine (free) | (3-Carboxy-2-hydroxypropyl)trimethylammonium hydroxide inner salt |
| Thr.K2 | Threonine | L-Threonine ((2S,3R)-2-amino-3-hydroxybutanoic acid |

Phe/Tyr

| | | |
|---|---|---|
| Gly.K2 | Glycine | Glycine |
| PC aa C26:0.K1 | | Glycerophosphocholine with estimated chemical composition (2 acyl residues) |
| C5-OH (C3-DC-M).K1 | 3-Hydroxyisovalerylcarnitine/3-Hydroxy-2-methylbutyryl | Acylcarnitine with estimated composition: mass of 2 possible residues is similar |
| PC aa C34:1.K1 | | Glycerophosphocholine with estimated chemical composition (2 acyl residues) |
| lysoPC a C28:1.K1 | | Glycerophosphocholine with estimated chemical composition (1 acyl residue) |

Met-SO/Met

| | | |
|---|---|---|
| C10:1.K1 | Decenoylcarnitine | chain length and number of double bonds is determined by the measured mass, but position and cis-trans-isomerie of double bonds is not specified (generally double bonds are cis) |
| PC aa C36:0.K1 | | Glycerophosphocholine with estimated chemical composition (2 acyl residues) |
| SDMA.K2 | Symmetrical Dimethylarginine | N,N'-Dimethyl-L-arginine |
| Trp.K2 | Tryptophan | L-Tryptophan |
| PC ae C34:3.K1 | | Glycerophosphocholine with estimated chemical composition (2 residues) |
| PC aa C36:2.K1 | | Glycerophosphocholine with estimated chemical composition (2 acyl residues) |
| PC aa C36:1.K1 | | Glycerophosphocholine with estimated chemical composition (2 acyl residues) |
| Kyn.K2 | Kynurenine | alpha-2-Diamino-gamma-oxobenzenebutyric acid |
| PC aa C32:1.K1 | | Glycerophosphocholine with estimated chemical composition (2 residues) |
| C7-DC.K1 | Pimelylcarnitine | |

SDMA/ADMA
PUFA/SFA

| | | |
|---|---|---|
| Arg.EM | Arginine | L-Arginine |
| PC aa C36:3.K1 | | Glycerophosphocholine with estimated chemical composition (2 acyl residues) |
| 13S-HODE.PA | 13(S)-hydroxy-9Z,11E-octadecadienoic acid | |
| PC ae C44:6.K1 | | Glycerophosphocholine with estimated chemical composition (2 residues) |
| lysoPC a C6:0.K1 | | Glycerophosphocholine with estimated chemical composition (1 acyl residue) |
| ADMA.K2 | asymmetrical Dimethylarginin | N,N-Dimethyl-L-arginine |
| PC aa C32:0.K1 | | Glycerophosphocholine with estimated chemical composition (2 residues) |

SumSMOH/SumSM
MUFA/SFA

| | | |
|---|---|---|
| PC ae C42:0.K1 | | Glycerophosphocholine with estimated chemical composition (2 residues) |
| C6:1.K1 | Hexenoylcarnitine | chain length and number of double bonds is determined by the measured mass, but position and cis-trans-isomerie, of double |

TABLE 1a-continued

Common and Systematic Name of Compounds

| BC Code | Common Name | Systematic Name |
|---|---|---|
| | | bonds is not specified (generally double bonds are cis) |
| lysoPC a C26:1.K1 | | Glycerophosphocholine with estimated chemical composition (1 acyl residue) |
| C12-DC.K1 | Dodecanedioylcarnitine | |
| C10.K1 | Decanoylcarnitine [Caprylcarnitine] (Fumarylcarnitine) | chain length is determined by the measured mass, condition unbranched fatty acid: Capric acid as residue |
| lysoPC a C26:0.K1 | | Glycerophosphocholine with estimated chemical composition (1 acyl residue) |

TABLE 1b

CAS-Numbers and Compound Species With The Same Structure

| BC Code | CAS Registry Number | Species with the same structure: |
|---|---|---|
| Suc.EM | 110-15-6 | |
| Lac.EM | 50-21-5 | (s)-2-Hydroxypropanoic acid, CAS-NR: 79-33-4; (r)-2-Hydroxypropanoic acid, CAS-Nr: 10326-41-7 |
| C4.K1 | 25576-40-3 | 3-butanoyloxy-4-trimethylammonio-butanoate (D) CAS-Nr: 25518-46-1 |
| Fum.EM | 110-17-8 | (Z)-2-Butenedioic acid (Maleic acid), CAS-Nr: 110-16-7 |
| GCA.BA | 475-31-0 | |
| C16:2.K1 | | |
| Putrescine.K2 | 110-60-1 | |
| | Glu/Gln | |
| C16:1.K1 | | |
| C10:2.K1 | | |
| TCDCA.BA | 516-35-8 | Tauroursodeoxycholic acid (Ethanesulfonic acid, 2-(((3-alpha,5-beta,7-beta)-3,7-dihydroxy-24-oxocholan-24-yl)amino)-), CAS-Nr: 14605-22-2 |
| GCDCA.BA | 640-79-9 | Glycine, N-((3alpha,5beta,7beta)-3,7-dihydroxy-24-oxocholan-24-yl)-, CAS-Nr: 2273-95-2 |
| Spermidine.K2 | 124-20-9 | |
| C18:2.K1 | | |
| CA.BA | 81-25-4 | (11 stereo centers = 2048 isomers, one is natural cholic acid), Allocholic acid CAS-Nr: 2464-18-8; Ursocholic acid Cas-Nr: 2955-27-3 |
| C5.K1 | | |
| Spermine.K2 | 71-44-3 | |
| Pyr + OAA.EM | | |
| C5:1-DC.K1 | | |
| C3.K1 | | |
| Lys.K2 | 56-87-1 | DL-Lysine CAS-Nr: 70-54-2; D-Lysine CAS-Nr: 923-27-3 |
| alpha-KGA.EM | 328-50-7 | |
| C18:1.K1 | | |
| C14:2.K1 | | |
| | Asp/Asn Putrescine/Orn | |
| Gln.K2 | 56-85-9 | DL-Glutamine CAS-Nr: 6899-04-3; D-Glutamine CAS-Nr: 5959-95-5 |
| UDCA.BA | 128-13-2 | Chenodiol (Cholan-24-oic acid, 3,7-dihydroxy-, (3alpha,5beta,7alpha)-) CAS-Nr: 474-25-9; Cholan-24-oic acid, 3,7-dihydroxy-,(3beta,5beta,7alpha)-CAS-Nr: 566-24-5; Isoursodeoxycholic acid (Cholan-24-oic acid, 3,7-dihydroxy-, (3beta,5beta,7beta)-) CAS-Nr: 78919-26-3 |
| PC ae C40:3.K1 | | |
| Serotonin.K2 | 50-67-9 | |
| | Orn/Cit | |
| Ala.K2 | 56-41-7 | DL-Alanine CAS-Nr: 302-72-7; D-Alanine CAS-Nr: 338-69-2; beta-Alanine CAS-Nr: 107-95-9 |
| C14.K1 | | |
| | Ala/BCAA | |
| His.K2 | 71-00-1 | DL-Histidine CAS-NR: 4998-57-6; D-Histidine CAS-Nr: 351-50-8 |
| lysoPC a C16:0.K1 | | Position and character of residue (a/e) is not clear! (m(lysoPC a C16.0) = m(lysoPC e C17.0)) |

TABLE 1b-continued

CAS-Numbers and Compound Species With The Same Structure

| BC Code | CAS Registry Number | Species with the same structure: |
|---|---|---|
| lysoPC a C17:0.K1 | | |
| C12.K1 | | |
| Pro.K2 | 147-85-3 | |
| | | Serotonin/Trp |
| C14:2-OH.K1 | | |
| Glu.K2 | 56-86-0 | DL-Glutamic acid CAS-Nr: 617-65-2; D-Glutamic acid CAS-Nr: 6893-26-1 |
| C16:2-OH.K1 | | |
| Histamine.K2 | 51-45-6 | |
| PC ae C30:0.K1 | | |
| C14:1.K1 | | |
| SumLyso | | |
| Phe.K2 | 63-91-2 | DL-Phenylalanine CAS-Nr: 150-30-1; D-Phenylalanine CAS-Nr: 673-06-3 |
| lysoPC a C18:0.K1 | | |
| PC aa C42:4.K1 | | |
| PC ae C38:4.K1 | | |
| PC ae C40:3.K1 | | |
| AA.PA | 506-32-1 | 8,11,14,17-Eicosatetraenoic acid CAS-Nr: 2091-26-1; 5,11,14,17-Eicosatetraenoic acid CAS-Nr: 2271-31-0; 5,8,11,14-Eicosatetraenoic acid CAS-Nr: 7771-44-0; theorretically as combination of E and Z double bonds is possible |
| C5:1.K1 | | |
| Met-SO.K2 | 62697-73-8 | Methionine S-oxide (L-Methionine sulfoxide) CAS-Nr: 3226-65-1; Butanoic acid, 2-amino-4-(methylsulfinyl)-, (S-(R*,S*))-CAS-NR: 50896-98-5 Spermine/Spermidine C16 + C18/C0 |
| C16.K1 | 1935-18-8 | Palmitoyl-D(+)-carnitin CAS-Nr: 2364-66-1; Palmitoyl-L-(−)-carnitin CAS-Nr: 2364-67-2 |
| lysoPC a C16:1.K1 | | |
| PC aa C40:4.K1 | | |
| Asn.K2 | 70-47-3 | DL-Asparagine CAS-Nr: 3130-87-8; D-Asparagine CAS-Nr: 2058-58-4 |
| C9.K1 | | |
| PC ae C42:5.K1 | | |
| C6 (C4:1-DC).K1 | | |
| PC aa C40:6.K1 | | |
| Val.K2 | 72-18-4 | DL-Valine CAS-Nr: 516-06-3; D-Valine CAS-Nr: 640-68-6 |
| SumSFA | | |
| PC ae C40:5.K1 | | |
| PC ae C42:4.K1 | | |
| PC ae C40:6.K1 | | |
| Leu.K2 | 61-90-5 | DL-Leucine CAS-Nr: 328-39-2; D-Leucine CAS-Nr: 328-38-1 |
| C2.K1 | 14992-62-2 | R-Acetylcarnitine CAS-Nr: 3040-38-8 |
| PC aa C40:5.K1 | | |
| PC ae C42:3.K1 | | |
| PC ae C40:4.K1 | | |
| Asp.EM | 56-84-8 | Aspartic acid CAS-Nr: 617-45-8; D-Aspartic acid CAS-Nr: 1783-96-6 |
| CDCA.BA | 474-25-9 | 8 possible isomers (3a,5a,7a; 3a,5a,7b; 3a,5b,7a; 3a,5b,7b; 3b,5a,7a; 3b,5a,7b; 3b,5b,7a; 3b,5b,7b); Found with CAS-numbers: Cholan-24-oic acid, 3,7-dihydroxy-, (3alpha,5beta,7beta)-(Ursodeoxycholic acid) CAS-Nr: 128-13-2; Cholan-24-oic acid, 3,7-dihydroxy-, (3beta,5beta,7alpha)-CAS-Nr: 566-24-5; Cholan-24-oic acid, 3,7-dihydroxy-, (3beta,5beta,7beta)-(Isoursodeoxycholic acid) CAS-Nr: 78919-26-3 |
| PC aa C38:6.K1 | | |
| SM (OH) C16:1.K1 | | |
| PC ae C38:5.K1 | | |
| C18:1-OH.K1 | | |
| | | Orn/Arg |
| C16:1-OH.K1 | | |
| C18.K1 | | |
| PC aa C36:6.K1 | | |
| SM C26:1.K1 | | |
| PC aa C42:5.K1 | | |

TABLE 1b-continued

CAS-Numbers and Compound Species With The Same Structure

| BC Code | CAS Registry Number | Species with the same structure: |
|---|---|---|
| C14:1-OH.K1 | | |
| PC aa C38:4.K1 | | |
| SumPC + Lyso | | |
| | | |
| PC ae C36:4.K1 | | |
| Hex.EM | | 8 Aldohexoses (D-Form) most common in nature: D-Glucose, D-Galactose and D-Mannose, 4 Ketohexoses (D-Form): D-Psicose, D-Fructose, D-Sorbose, D-Tagatose |
| LCA.BA | 434-13-9 | Cholan-24-oic acid, 3-hydroxy-, (3beta,5beta)-(Isolithocholic acid) CAS-Nr: 1534-35-6; Cholan-24-oic acid, 3-hydroxy-, (3beta,5alpha)-(9Cl) (Alloisolithocholic acid) CAS-Nr: 2276-93-9 |
| PC aa C36:4.K1 | | |
| SumPC | | |
| SumPUFA | | |
| | | |
| PC aa C40:2.K1 | | |
| Met.K2 | 63-68-3 | DL-Methionine CAS-Nr: 59-51-8; D-Methionine CAS-Nr: 348-67-4 |
| PC ae C38:3.K1 | | |
| PC ae C32:2.K1 | | |
| Cit.K2 | 372-75-8 | DL-2-Amino-5-ureidovaleric acid CAS-Nr: 627-77-0 |
| PC ae C30:1.K1 | | |
| PC ae C42:2.K1 | | |
| | Kyn/Trp | |
| | | |
| Orn.K2 | 70-26-8 | DL-Ornithine CAS-NR: 616-07-9; D-Ornithine CAS-Nr: 348-66-3 |
| PC ae C38:6.K1 | | |
| lysoPC a C20:4.K1 | | |
| PC ae C40:1.K1 | | |
| Asp.K2 | 56-84-8 | D,L-Aspartic acid CAS-Nr: 617-45-8; D-Aspartic acid CAS-Nr: 1783-96-6 |
| PC aa C30:2.K1 | | |
| PC aa C28:1.K1 | | |
| | Gly/BCAA | |
| | | |
| PC aa C38:5.K1 | | |
| PC ae C34:1.K1 | | |
| PC aa C38:3.K1 | | |
| C16-OH.K1 | | |
| SM (OH) C14:1.K1 | | |
| PC ae C44:4.K1 | | |
| PC ae C38:1.K1 | | |
| SumSM | | |
| SumMUFA | | |
| | | |
| PC ae C40:2.K1 | | |
| lysoPC a C24:0.K1 | | |
| OH-Kyn.K2 | 484-78-6 | L-3-Hydroxykynurenine CAS-Nr: 606-14-4; 5-Hydroxykynurenine CAS-Nr: 720-00-3 |
| SM (OH) C22:1.K1 | | |
| PC ae C32:1.K1 | | |
| SM C16:1.K1 | | |
| PC ae C30:2.K1 | | |
| | Ala/Lys | |
| | | |
| Tyr.K2 | 60-18-4 | DL-Tyrosine CAS-Nr: 556-03-6; D-Tyrosine CAS-Nr: 556-02-5 |
| PC ae C34:0.K1 | | |
| PC ae C36:0.K1 | | |
| SM (OH) C22:2.K1 | | |
| lysoPC a C28:0.K1 | | |
| C12:1.K1 | | |
| PC aa C34:4.K1 | | |
| SM C26:0.K1 | | |
| SM (OH) C24:1.K1 | | |
| SM C16:0.K1 | | |
| Ile.K2 | 73-32-5 | DL-Isoleucine CAS-Nr: 443-79-8; Allo-L-Isoleucine CAS-Nr: 1509-34-8; Allo-D-Isoleucine CAS-Nr: 1509-35-9; Allo-DL-Isoleucine CAS-Nr: 3107-04-8 |
| C5-DC (C6-OH).K1 | | |
| PC aa C38:0.K1 | | |
| PC aa C34:2.K1 | | |

TABLE 1b-continued

CAS-Numbers and Compound Species With The Same Structure

| BC Code | CAS Registry Number | Species with the same structure: |
|---|---|---|
| | Cit/Arg | |
| Ser.K2 | 56-45-1 | DL-Serine CAS-Nr: 302-84-1; D-Serine CAS-Nr: 312-84-5 |
| PC ae C36:5.K1 | | |
| PC ae C34:2.K1 | | |
| PC ae C36:3.K1 | | |
| C3-OH.K1 | | |
| PC ae C42:1.K1 | | |
| H1.K1 | | 8 Aldohexoses (D-Form) most common in nature: D-Glucose, D-Galactose and D-Mannose, 4 Ketohexoses (D-Form): D-Psicose, D-Fructose, D-Sorbose, D-Tagatose |
| PC ae C36:2.K1 | | |
| SM C22:3.K1 | | |
| SM C24:1.K1 | | |
| C4-OH (C3-DC).K1 | | |
| PC aa C40:1.K1 | | |
| PC aa C32:3.K1 | | |
| PC aa C42:1.K1 | | |
| PC aa C36:5.K1 | | |
| PC aa C42:6.K1 | | |
| DHA.PA | 6217-54-5 | cis-trans-isomerie of double bonds is not specified: CAS-Nr: 25167-62-8; |
| SM C20:2.K1 | | |
| C4:1.K1 | | |
| SM C24:0.K1 | | |
| PC ae C38:0.K1 | | |
| | Kyn/OHKyn | |
| Arg.K2 | 74-79-3 | DL-Arginine CAS-Nr: 7200-25-1; D-Arginine CAS-Nr: 157-06-2 |
| total DMA.K2 | | |
| PC aa C34:3.K1 | | |
| PC ae C38:2.K1 | | |
| | PUFA/MUFA | |
| PC aa C42:0.K1 | | |
| SM C18:1.K1 | | |
| PC aa C32:2.K1 | | |
| lysoPC a C18:2.K1 | | |
| PC ae C44:3.K1 | | |
| PC ae C40:0.K1 | | |
| Xle.K2 | | |
| PC aa C24:0.K1 | | |
| PC aa C38:1.K1 | | |
| SM C18:0.K1 | | |
| PC aa C42:2.K1 | | |
| lysoPC a C20:3.K1 | | |
| PC ae C36:1.K1 | | |
| C3:1.K1 | | |
| lysoPC a C18:1.K1 | | |
| C8:1.K1 | | |
| C8.K1 | | |
| PC aa C30:0.K1 | | |
| PC ae C44:5.K1 | | |
| lysoPC a C14:0.K1 | | |
| Creatinine.K2 | 60-27-5 | |
| C0.K1 | 461-06-3 | DL-Carnitine CAS-Nr: 406-76-8; D-Carnitine CAS-Nr: 541-14-0 |
| Thr.K2 | 72-19-5 | DL-Threonine CAS-Nr: 80-68-2; D-Threonine CAS-Nr: 632-20-2; Allo-DL-Threonine ((2S,3S)-2-amino-3-hydroxybutanoic acid) CAS-Nr: 144-98-9 |
| | Phe/Tyr | |
| Gly.K2 | 56-40-6 | |
| PC aa C26:0.K1 | | |
| C5-OH (C3-DC-M).K1 | | |
| PC aa C34:1.K1 | | |
| lysoPC a C28:1.K1 | | |
| | Met-SO/Met | |
| C10:1.K1 | | |
| PC aa C36:0.K1 | | |
| SDMA.K2 | 30344-00-4 | |

TABLE 1b-continued

CAS-Numbers and Compound Species With The Same Structure

| BC Code | CAS Registry Number | Species with the same structure: |
|---|---|---|
| Trp.K2 | 73-22-3 | DL-Tryptophan CAS-Nr: 54-12-6; D-Tryptophan CAS-Nr: 153-94-6 |
| PC ae C34:3.K1 | | |
| PC aa C36:2.K1 | | |
| PC aa C36:1.K1 | | |
| Kyn.K2 | 343-65-7 | |
| PC aa C32:1.K1 | | |
| C7-DC.K1 | | |
| | | SDMA/ADMA |
| | | PUFA/SFA |
| Arg.EM | 74-79-3 | DL-Arginine CAS-Nr: 7200-25-1; D-Arginine CAS-Nr: 157-06-2 |
| PC aa C36:3.K1 | | |
| 13S-HODE.PA | | 13-Hydroxyoctadecadienoic acid CAS-Nr: 5204-88-6; 9,11-Octadecadienoic acid, 13-hydroxy-, (R-(E,Z))-CAS-Nr: 10219-69-9 |
| PC ae C44:6.K1 | | |
| lysoPC a C6:0.K1 | | |
| ADMA.K2 | 30315-93-6 | N,N-Dimethyl-L-arginine CAS-Nr: 102783-24-4 |
| PC aa C32:0.K1 | | |
| | | SumSMOH/SumSM |
| | | MUFA/SFA |
| PC ae C42:0.K1 | | |
| C6:1.K1 | | |
| lysoPC a C26:1.K1 | | |
| C12-DC.K1 | | |
| C10.K1 | | |
| lysoPC a C26:0.K1 | | |

Table 1a and 1b summarize analyzed metabolites and respective abbreviations; Glycero-phospholipids are further differentiated with respect to the presence of ester (a) and ether (e) bonds in the glycerol moiety, where two letters (aa, ea, or ee) denote that the first and the second position of the glycerol scaffold are bound to a fatty acid residue, whereas a single letter (a or e) indicates a bond with only one fatty acid residue; e.g. PC_ea_33:1 denotes a plasmalogen phosphatidylcholine with 33 carbons in the two fatty acid side chains and a single double bond in one of them.

TABLE 1c

Compounds and Chemical Families

| Name in datasets | Lab name | Explicit name | Chemical Family |
|---|---|---|---|
| C0.K1 | C0 | Carnitine (free) | ac.carnitines |
| | | Decanoylcarnitine [Caprylcarnitine] | |
| C10.K1 | C10(C4:1-DC) | (Fumarylcarnitine) | ac.carnitines |
| C10:1.K1 | C10:1 | Decenoylcarnitine | ac.carnitines |
| C10:2.K1 | C10:2 | Decadienoylcarnitine | ac.carnitines |
| C12.K1 | C12 | Dodecanoylcarnitine [Laurylcarnitine] | ac.carnitines |
| C12-DC.K1 | C12-DC | Dodecanedioylcarnitine | ac.carnitines |
| C12:1.K1 | C12:1 | Dodecenoylcarnitine | ac.carnitines |
| C14.K1 | C14 | Tetradecanoylcarnitine [Myristylcarnitine] | ac.carnitines |
| C14:1.K1 | C14:1 | Tetradecenoylcarnitine [Myristoleylcarnitine] | ac.carnitines |
| C14:1-OH.K1 | C14:1-OH | 3-Hydroxytetradecenoylcarnitine [3-Hydroxymyristoleylcarnitine] | ac.carnitines |
| C14:2.K1 | C14:2 | Tetradecadienoylcarnitine | ac.carnitines |
| C14:2-OH.K1 | C14:2-OH | 3-Hydroxytetradecadienoylcarnitine | ac.carnitines |
| C16.K1 | C16 | Hexadecanoylcarnitine [Palmitoylcarnitine] | ac.carnitines |
| C16-OH.K1 | C16-OH | 3-Hydroxyhexadecanoylcarnitine [3-Hydroxypalmitoylcarnitine] | ac.carnitines |
| C16:1.K1 | C16:1 | Hexadecenoylcarnitine [Palmitoleylcarnitine] | ac.carnitines |
| C16:1-OH.K1 | C16:1-OH | 3-Hydroxyhexadecenoylcarnitine [3-Hydroxypalmitoleylcarnitine] | ac.carnitines |
| C16:2.K1 | C16:2 | Hexadecadienoylcarnitine | ac.carnitines |
| C16:2-OH.K1 | C16:2-OH | 3-Hydroxyhexadecadienoylcarnitine | ac.carnitines |

TABLE 1c-continued

Compounds and Chemical Families

| Name in datasets | Lab name | Explicit name | Chemical Family |
|---|---|---|---|
| C18.K1 | C18 | Octadecanoylcarnitine [Stearylcarnitine] | ac.carnitines |
| C18:1.K1 | C18:1 | Octadecenoylcarnitine [Oleylcarnitine] | ac.carnitines |
| C18:1-OH.K1 | C18:1-OH | 3-Hydroxyoctadecenoylcarnitine [3-Hydroxyoleylcarnitine] | ac.carnitines |
| C18:2.K1 | C18:2 | Octadecadienoylcarnitine [Linoleylcarnitine] | ac.carnitines |
| C2.K1 | C2 | Acetylcarnitine | ac.carnitines |
| C3.K1 | C3 | Propionylcarnitine | ac.carnitines |
| C3-OH.K1 | C3-OH | Hydroxypropionylcarnitine | ac.carnitines |
| C3:1.K1 | C3:1 | Propenoylcarnitine | ac.carnitines |
| C4.K1 | C4 | Butyrylcarnitine/Isobutyrylcarnitine | ac.carnitines |
| C4-OH (C3-DC).K1 | C4-OH (C3-DC) | 3-Hydroxybutyrylcarnitine | ac.carnitines |
| C4:1.K1 | C4:1 | Butenoylcarnitine | ac.carnitines |
| C5.K1 | C5 | Isovalerylcarnitine/2-Methylbutyrylcarnitine/ Valerylcarnitine | ac.carnitines |
| C5-DC (C6-OH).K1 | C5-DC (C6-OH) | Glutarylcarnitine | ac.carnitines |
| C5-OH (C3-DC-M).K1 | C5-OH (C3-DC-M) | 3-Hydroxyisovalerylcarnitine/3-Hydroxy-2-methylbutyryl | ac.carnitines |
| C5:1.K1 | C5:1 | Tiglylcarnitine/3-Methyl-crotonylcarnitine | ac.carnitines |
| C5:1-DC.K1 | C5:1-DC | Glutaconylcarnitine/ Mesaconylcarnitine (Undecanoylcarnitine) | ac.carnitines |
| C6 (C4:1-DC).K1 | C6 | Hexanoylcarnitine [Caproylcarnitine] | ac.carnitines |
| C6:1.K1 | C6:1 | Hexenoylcarnitine | ac.carnitines |
| C7-DC.K1 | C7-DC | Pimelylcarnitine | ac.carnitines |
| C8.K1 | C8 | Octanoylcarnitine [Caprylylcarnitine] | ac.carnitines |
| C8:1.K1 | C8:1 | Octenoylcarnitine | ac.carnitines |
| C9.K1 | C9 | Nonanoylcarnitine [Pelargonylcarnitine] | ac.carnitines |
| H1.K1 | H1 | Hexoses | sugars |
| SM (OH) C14:1.K1 | SM (OH) C14:1 | Hydroxysphingomyelin with acyl residue sum C14:1 | sphingolipids |
| SM (OH) C16:1.K1 | SM (OH) C16:1 | Hydroxysphingomyelin with acyl residue sum C16:1 | sphingolipids |
| SM (OH) C22:1.K1 | SM (OH) C22:1 | Hydroxysphingomyelin with acyl residue sum C22:1 | sphingolipids |
| SM (OH) C22:2.K1 | SM (OH) C22:2 | Hydroxysphingomyelin with acyl residue sum C22:2 | sphingolipids |
| SM (OH) C24:1.K1 | SM (OH) C24:1 | Hydroxysphingomyelin with acyl residue sum C24:1 | sphingolipids |
| SM C16:0.K1 | SM C16:0 | sphingomyelin with acyl residue sum C16:0 | sphingolipids |
| SM C16:1.K1 | SM C16:1 | sphingomyelin with acyl residue sum C16:1 | sphingolipids |
| SM C18:0.K1 | SM C18:0 | sphingomyelin with acyl residue sum C18:0 | sphingolipids |
| SM C18:1.K1 | SM C18:1 | sphingomyelin with acyl residue sum C18:1 | sphingolipids |
| SM C20:2.K1 | SM C20:2 | sphingomyelin with acyl residue sum C20:2 | sphingolipids |
| SM C22:3.K1 | SM C22:3 | sphingomyelin with acyl residue sum C22:3 | sphingolipids |
| SM C24:0.K1 | SM C24:0 | sphingomyelin with acyl residue sum C24:0 | sphingolipids |
| SM C24:1.K1 | SM C24:1 | sphingomyelin with acyl residue sum C24:1 | sphingolipids |
| SM C26:0.K1 | SM C26:0 | sphingomyelin with acyl residue sum C26:0 | sphingolipids |
| SM C26:1.K1 | SM C26:1 | sphingomyelin with acyl residue sum C26:1 | sphingolipids |
| PC aa C24:0.K1 | PC aa C24:0 | Phosphatidylcholine with diacyl residue sum C24:0 | glycerophospholipids |
| PC aa C26:0.K1 | PC aa C26:0 | Phosphatidylcholine with diacyl residue sum C26:0 | glycerophospholipids |
| PC aa C28:1.K1 | PC aa C28:1 | Phosphatidylcholine with diacyl residue sum C28:1 | glycerophospholipids |
| PC aa C30:0.K1 | PC aa C30:0 | Phosphatidylcholine with diacyl residue sum C30:0 | glycerophospholipids |
| PC aa | PC aa C30:2 | Phosphatidylcholine with diacyl | glycerophospholipids |

TABLE 1c-continued

Compounds and Chemical Families

| Name in datasets | Lab name | Explicit name | Chemical Family |
|---|---|---|---|
| C30:2.K1 | | residue sum C30:2 | |
| PC aa C32:0.K1 | PC aa C32:0 | Phosphatidylcholine with diacyl residue sum C32:0 | glycerophospholipids |
| PC aa C32:1.K1 | PC aa C32:1 | Phosphatidylcholine with diacyl residue sum C32:1 | glycerophospholipids |
| PC aa C32:2.K1 | PC aa C32:2 | Phosphatidylcholine with diacyl residue sum C32:2 | glycerophospholipids |
| PC aa C32:3.K1 | PC aa C32:3 | Phosphatidylcholine with diacyl residue sum C32:3 | glycerophospholipids |
| PC aa C34:1.K1 | PC aa C34:1 | Phosphatidylcholine with diacyl residue sum C34:1 | glycerophospholipids |
| PC aa C34:2.K1 | PC aa C34:2 | Phosphatidylcholine with diacyl residue sum C34:2 | glycerophospholipids |
| PC aa C34:3.K1 | PC aa C34:3 | Phosphatidylcholine with diacyl residue sum C34:3 | glycerophospholipids |
| PC aa C34:4.K1 | PC aa C34:4 | Phosphatidylcholine with diacyl residue sum C34:4 | glycerophospholipids |
| PC aa C36:0.K1 | PC aa C36:0 | Phosphatidylcholine with diacyl residue sum C36:0 | glycerophospholipids |
| PC aa C36:1.K1 | PC aa C36:1 | Phosphatidylcholine with diacyl residue sum C36:1 | glycerophospholipids |
| PC aa C36:2.K1 | PC aa C36:2 | Phosphatidylcholine with diacyl residue sum C36:2 | glycerophospholipids |
| PC aa C36:3.K1 | PC aa C36:3 | Phosphatidylcholine with diacyl residue sum C36:3 | glycerophospholipids |
| PC aa C36:4.K1 | PC aa C36:4 | Phosphatidylcholine with diacyl residue sum C36:4 | glycerophospholipids |
| PC aa C36:5.K1 | PC aa C36:5 | Phosphatidylcholine with diacyl residue sum C36:5 | glycerophospholipids |
| PC aa C36:6.K1 | PC aa C36:6 | Phosphatidylcholine with diacyl residue sum C36:6 | glycerophospholipids |
| PC aa C38:0.K1 | PC aa C38:0 | Phosphatidylcholine with diacyl residue sum C38:0 | glycerophospholipids |
| PC aa C38:1.K1 | PC aa C38:1 | Phosphatidylcholine with diacyl residue sum C38:1 | glycerophospholipids |
| PC aa C38:3.K1 | PC aa C38:3 | Phosphatidylcholine with diacyl residue sum C38:3 | glycerophospholipids |
| PC aa C38:4.K1 | PC aa C38:4 | Phosphatidylcholine with diacyl residue sum C38:4 | glycerophospholipids |
| PC aa C38:5.K1 | PC aa C38:5 | Phosphatidylcholine with diacyl residue sum C38:5 | glycerophospholipids |
| PC aa C38:6.K1 | PC aa C38:6 | Phosphatidylcholine with diacyl residue sum C38:6 | glycerophospholipids |
| PC aa C40:1.K1 | PC aa C40:1 | Phosphatidylcholine with diacyl residue sum C40:1 | glycerophospholipids |
| PC aa C40:2.K1 | PC aa C40:2 | Phosphatidylcholine with diacyl residue sum C40:2 | glycerophospholipids |
| PC aa C40:3.K1 | PC aa C40:3 | Phosphatidylcholine with diacyl residue sum C40:3 | glycerophospholipids |
| PC aa C40:4.K1 | PC aa C40:4 | Phosphatidylcholine with diacyl residue sum C40:4 | glycerophospholipids |
| PC aa C40:5.K1 | PC aa C40:5 | Phosphatidylcholine with diacyl residue sum C40:5 | glycerophospholipids |
| PC aa C40:6.K1 | PC aa C40:6 | Phosphatidylcholine with diacyl residue sum C40:6 | glycerophospholipids |
| PC aa C42:0.K1 | PC aa C42:0 | Phosphatidylcholine with diacyl residue sum C42:0 | glycerophospholipids |
| PC aa C42:1.K1 | PC aa C42:1 | Phosphatidylcholine with diacyl residue sum C42:1 | glycerophospholipids |
| PC aa C42:2.K1 | PC aa C42:2 | Phosphatidylcholine with diacyl residue sum C42:2 | glycerophospholipids |
| PC aa C42:4.K1 | PC aa C42:4 | Phosphatidylcholine with diacyl residue sum C42:4 | glycerophospholipids |
| PC aa C42:5.K1 | PC aa C42:5 | Phosphatidylcholine with diacyl residue sum C42:5 | glycerophospholipids |
| PC aa C42:6.K1 | PC aa C42:6 | Phosphatidylcholine with diacyl residue sum C42:6 | glycerophospholipids |
| PC ae C30:0.K1 | PC ae C30:0 | Phosphatidylcholine with acyl-alkyl residue sum C30:0 | glycerophospholipids |
| PC ae C30:1.K1 | PC ae C30:1 | Phosphatidylcholine with acyl-alkyl residue sum C30:1 | glycerophospholipids |
| PC ae C30:2.K1 | PC ae C30:2 | Phosphatidylcholine with acyl-alkyl residue sum C30:2 | glycerophospholipids |
| PC ae | PC ae C32:1 | Phosphatidylcholine with acyl-alkyl | glycerophospholipids |

TABLE 1c-continued

Compounds and Chemical Families

| Name in datasets | Lab name | Explicit name | Chemical Family |
|---|---|---|---|
| C32:1.K1 | | residue sum C32:1 | |
| PC ae C32:2.K1 | PC ae C32:2 | Phosphatidylcholine with acyl-alkyl residue sum C32:2 | glycerophospholipids |
| PC ae C34:0.K1 | PC ae C34:0 | Phosphatidylcholine with acyl-alkyl residue sum C34:0 | glycerophospholipids |
| PC ae C34:1.K1 | PC ae C34:1 | Phosphatidylcholine with acyl-alkyl residue sum C34:1 | glycerophospholipids |
| PC ae C34:2.K1 | PC ae C34:2 | Phosphatidylcholine with acyl-alkyl residue sum C34:2 | glycerophospholipids |
| PC ae C34:3.K1 | PC ae C34:3 | Phosphatidylcholine with acyl-alkyl residue sum C34:3 | glycerophospholipids |
| PC ae C36:0.K1 | PC ae C36:0 | Phosphatidylcholine with acyl-alkyl residue sum C36:0 | glycerophospholipids |
| PC ae C36:1.K1 | PC ae C36:1 | Phosphatidylcholine with acyl-alkyl residue sum C36:1 | glycerophospholipids |
| PC ae C36:2.K1 | PC ae C36:2 | Phosphatidylcholine with acyl-alkyl residue sum C36:2 | glycerophospholipids |
| PC ae C36:3.K1 | PC ae C36:3 | Phosphatidylcholine with acyl-alkyl residue sum C36:3 | glycerophospholipids |
| PC ae C36:4.K1 | PC ae C36:4 | Phosphatidylcholine with acyl-alkyl residue sum C36:4 | glycerophospholipids |
| PC ae C36:5.K1 | PC ae C36:5 | Phosphatidylcholine with acyl-alkyl residue sum C36:5 | glycerophospholipids |
| PC ae C38:0.K1 | PC ae C38:0 | Phosphatidylcholine with acyl-alkyl residue sum C38:0 | glycerophospholipids |
| PC ae C38:1.K1 | PC ae C38:1 | Phosphatidylcholine with acyl-alkyl residue sum C38:1 | glycerophospholipids |
| PC ae C38:2.K1 | PC ae C38:2 | Phosphatidylcholine with acyl-alkyl residue sum C38:2 | glycerophospholipids |
| PC ae C38:3.K1 | PC ae C38:3 | Phosphatidylcholine with acyl-alkyl residue sum C38:3 | glycerophospholipids |
| PC ae C38:4.K1 | PC ae C38:4 | Phosphatidylcholine with acyl-alkyl residue sum C38:4 | glycerophospholipids |
| PC ae C38:5.K1 | PC ae C38:5 | Phosphatidylcholine with acyl-alkyl residue sum C38:5 | glycerophospholipids |
| PC ae C38:6.K1 | PC ae C38:6 | Phosphatidylcholine with acyl-alkyl residue sum C38:6 | glycerophospholipids |
| PC ae C40:0.K1 | PC ae C40:0 | Phosphatidylcholine with acyl-alkyl residue sum C40:0 | glycerophospholipids |
| PC ae C40:1.K1 | PC ae C40:1 | Phosphatidylcholine with acyl-alkyl residue sum C40:1 | glycerophospholipids |
| PC ae C40:2.K1 | PC ae C40:2 | Phosphatidylcholine with acyl-alkyl residue sum C40:2 | glycerophospholipids |
| PC ae C40:3.K1 | PC ae C40:3 | Phosphatidylcholine with acyl-alkyl residue sum C40:3 | glycerophospholipids |
| PC ae C40:4.K1 | PC ae C40:4 | Phosphatidylcholine with acyl-alkyl residue sum C40:4 | glycerophospholipids |
| PC ae C40:5.K1 | PC ae C40:5 | Phosphatidylcholine with acyl-alkyl residue sum C40:5 | glycerophospholipids |
| PC ae C40:6.K1 | PC ae C40:6 | Phosphatidylcholine with acyl-alkyl residue sum C40:6 | glycerophospholipids |
| PC ae C42:0.K1 | PC ae C42:0 | Phosphatidylcholine with acyl-alkyl residue sum C42:0 | glycerophospholipids |
| PC ae C42:1.K1 | PC ae C42:1 | Phosphatidylcholine with acyl-alkyl residue sum C42:1 | glycerophospholipids |
| PC ae C42:2.K1 | PC ae C42:2 | Phosphatidylcholine with acyl-alkyl residue sum C42:2 | glycerophospholipids |
| PC ae C42:3.K1 | PC ae C42:3 | Phosphatidylcholine with acyl-alkyl residue sum C42:3 | glycerophospholipids |
| PC ae C42:4.K1 | PC ae C42:4 | Phosphatidylcholine with acyl-alkyl residue sum C42:4 | glycerophospholipids |
| PC ae C42:5.K1 | PC ae C42:5 | Phosphatidylcholine with acyl-alkyl residue sum C42:5 | glycerophospholipids |
| PC ae C44:3.K1 | PC ae C44:3 | Phosphatidylcholine with acyl-alkyl residue sum C44:3 | glycerophospholipids |
| PC ae C44:4.K1 | PC ae C44:4 | Phosphatidylcholine with acyl-alkyl residue sum C44:4 | glycerophospholipids |
| PC ae C44:5.K1 | PC ae C44:5 | Phosphatidylcholine with acyl-alkyl residue sum C44:5 | glycerophospholipids |
| PC ae C44:6.K1 | PC ae C44:6 | Phosphatidylcholine with acyl-alkyl residue sum C44:6 | glycerophospholipids |
| lysoPC a C14:0.K1 | lysoPC a C14:0 | Lysophosphatidylcholine with acyl residue C14:0 | glycerophospholipids |
| lysoPC a | lysoPC a | Lysophosphatidylcholine with acyl | glycerophospholipids |

TABLE 1c-continued

Compounds and Chemical Families

| Name in datasets | Lab name | Explicit name | Chemical Family |
|---|---|---|---|
| C16:0.K1 | C16:0 | residue C16:0 | |
| lysoPC a C16:1.K1 | lysoPC a C16:1 | Lysophosphatidylcholine with acyl residue C16:1 | glycerophospholipids |
| lysoPC a C17:0.K1 | lysoPC a C17:0 | Lysophosphatidylcholine with acyl residue C17:0 | glycerophospholipids |
| lysoPC a C18:0.K1 | lysoPC a C18:0 | Lysophosphatidylcholine with acyl residue C18:0 | glycerophospholipids |
| lysoPC a C18:1.K1 | lysoPC a C18:1 | Lysophosphatidylcholine with acyl residue C18:1 | glycerophospholipids |
| lysoPC a C18:2.K1 | lysoPC a C18:2 | Lysophosphatidylcholine with acyl residue C18:2 | glycerophospholipids |
| lysoPC a C20:3.K1 | lysoPC a C20:3 | Lysophosphatidylcholine with acyl residue C20:3 | glycerophospholipids |
| lysoPC a C20:4.K1 | lysoPC a C20:4 | Lysophosphatidylcholine with acyl residue C20:4 | glycerophospholipids |
| lysoPC a C24:0.K1 | lysoPC a C24:0 | Lysophosphatidylcholine with acyl residue C24:0 | glycerophospholipids |
| lysoPC a C26:0.K1 | lysoPC a C26:0 | Lysophosphatidylcholine with acyl residue C26:0 | glycerophospholipids |
| lysoPC a C26:1.K1 | lysoPC a C26:1 | Lysophosphatidylcholine with acyl residue C26:1 | glycerophospholipids |
| lysoPC a C28:0.K1 | lysoPC a C28:0 | Lysophosphatidylcholine with acyl residue C28:0 | glycerophospholipids |
| lysoPC a C28:1.K1 | lysoPC a C28:1 | Lysophosphatidylcholine with acyl residue C28:1 | glycerophospholipids |
| lysoPC a C6:0.K1 | lysoPC a C6:0 | Lysophosphatidylcholine with acyl residue C6:0 | glycerophospholipids |
| Gly.K2 | Gly | Glycine | aminoacids |
| Ala.K2 | Ala | Alanine | aminoacids |
| Ser.K2 | Ser | Serine | aminoacids |
| Pro.K2 | Pro | Proline | aminoacids |
| Val.K2 | Val | Valine | aminoacids |
| Thr.K2 | Thr | Threonine | aminoacids |
| Xle.K2 | Ile | Isoleucine | aminoacids |
| Leu.K2 | Leu | Leucine | aminoacids |
| Ile.K2 | Ile | Isoleucine | aminoacids |
| Asn.K2 | Asn | Asparagine | aminoacids |
| Asp.K2 | Asp | Aspartic acid | aminoacids |
| Gln.K2 | Gln | Glutamine | aminoacids |
| Glu.K2 | Glu | Glutamate | aminoacids |
| Met.K2 | Met | Methionine | aminoacids |
| His.K2 | His | Histidine | aminoacids |
| Phe.K2 | Phe | Phenylalanine | aminoacids |
| Arg.K2 | Arg | Arginine | aminoacids |
| Cit.K2 | Cit | Citrulline | aminoacids |
| Tyr.K2 | Tyr | Tyrosine | aminoacids |
| Trp.K2 | Trp | Tryptophane | aminoacids |
| Orn.K2 | Orn | Ornithine | aminoacids |
| Lys.K2 | Lys | Lysine | aminoacids |
| ADMA.K2 | ADMA | Asymmetric dimethylarginine | biogenic amine |
| SDMA.K2 | SDMA | Symmetric dimethylarginine | biogenic amine |
| total DMA.K2 | totalDMA | Total dimethylarginine | biogenic amine |
| Histamine.K2 | Histamine | Histamine | biogenic amine |
| Met-SO.K2 | Methionine-Sulfoxide | Methionine-Sulfoxide | aminoacids |
| Kyn.K2 | Kynurenine | Kynurenine | biogenic amine |
| OH-Kyn.K2 | Hydroxykynurenine | Hydroxykynurenine | biogenic amine |
| Putrescine.K2 | Putrescine | Putrescine | biogenic amine |
| Spermidine.K2 | Spermidine | Spermidine | biogenic amine |
| Spermine.K2 | Spermine | Spermine | biogenic amine |
| Serotonin.K2 | Serotonin | Serotonin | biogenic amine |
| Creatinine.K2 | Creatinine | Creatinine | biogenic amine |
| Lac.EM | Lac | Lactate | acid |
| Fum.EM | Fum | Fumaric acid | acid |
| Asp.EM | Asp | Aspartic acid | aminoacids |
| Arg.EM | Arg | Arginine | aminoacids |
| Pyr + OAA.EM | Pyr + OAA | Pyruvate + Oxaloacetate | acid |
| Suc.EM | Suc | Succinic acid | acid |
| alpha-KGA.EM | alpha-KGA | alpha-Ketoglutaric acid | acid |
| Hex.EM | Hex | Hexose (e.g. Glucose) | sugars |

TABLE 1c-continued

Compounds and Chemical Families

| Name in datasets | Lab name | Explicit name | Chemical Family |
|---|---|---|---|
| TCDCA.BA | TCDCA | Taurochenodeoxycholic Acid | bile acid |
| GCA.BA | GCA | Glycocholic Acid | bile acid |
| CA.BA | CA | Cholic Acid | bile acid |
| UDCA.BA | UDCA | Ursodeoxycholic Acid | bile acid |
| CDCA.BA | CDCA | Chenodeoxycholic Acid | bile acid |
| GCDCA.BA | GCDCA | Glycochenodeoxycholic Acid | bile acid |
| LCA.BA | LCA | Lithocholic Acid | bile acid |
| 13S-HODE.PA | 13S-HODE | 13(S)-hydroxy-9Z,11E-octadecadienoic acid | prostaglandin |
| DHA.PA | DHA | Docosahexaenoic acid | prostaglandin |
| AA.PA | AA | Arachidonic acid | prostaglandin |
| 22ROHC | 22-R-Hydroxycholesterol | Cholest-5-ene-3,22-diol, (3beta,22R)- | Cholesterol compound |
| 24SOHC | 24-S-Hydroxycholesterol | Cholest-5-ene-3,24-diol, (3beta,24S)- | Cholesterol compound |
| 25OHC | 25-Hydroxycholesterol | Cholest-5-ene-3beta,25-diol | Cholesterol compound |
| 27OHC | 27-Hydroxycholesterol | Cholest-5-ene-3,26,diol, (3beta,25R)- | Cholesterol compound |
| 20aOHC | 20α-Hydroxycholesterol | Cholest-5-ene-3beta,20-diol, (20S)- | Cholesterol compound |
| 22SOHC | 22S-Hydroxycholesterol | Cholest-5-ene-3,22-diol, (3beta,22S)- | Cholesterol compound |
| 24,25EC | 24,25-Epoxycholesterol | Cholestan-3-ol, 24,25-epoxy-, (3alpha,5beta)- | Cholesterol compound |
| 3B,5a,6BTHC | 3β,5α,6β-Trihydroxycholestan | Cholestane-3beta,5alpha,6beta-triol | Cholesterol compound |
| 7aOHC | 7α-Hydroxycholesterol | Cholest-5-ene-3,7-diol, (3beta,7alpha)- | Cholesterol compound |
| 7KC | 7-Ketocholesterol | Cholest-5-en-7-one, 3-hydroxy-, (3-beta)- | Cholesterol compound |
| 5B,6B,EC | 5β,6β-Epoxycholesterol | Cholestan-3-ol, 5,6-epoxy-, (3beta,5beta,6beta)- | Cholesterol compound |
| 5a,6a,EC | 5α,6α-Epoxycholesterol | Cholestan-3-ol, 5,6-epoxy-, (3beta,5alpha,6alpha)- | Cholesterol compound |
| 4BOHC | 4β-Hydroxycholesterol | Cholest-5-ene-3,4-diol, (3beta,4beta)- | Cholesterol compound |
| Desmosterol | Desmosterol | Cholesta-5,24-dien-3-ol, (3beta)- | Cholesterol compound |
| 7DHC | 7-Dehydrocholesterol | Cholesta-5,7-dien-3-ol, (3beta)- | Cholesterol compound |
| Cholestenone | Cholestenone | Cholest-5-en-3-one | Cholesterol compound |
| Lanosterol | Lanosterol | Lanosta-8,24-dien-3-ol, (3beta)- | Cholesterol compound |
| 24DHLan | 24-Dihydrolanosterol | (3beta)-Lanost-8-en-3-ol | Cholesterol compound |

EXAMPLES

Piglets were subjected to asphyxia. To "mimic" birth asphyxia we exposed the whole body to hypoxia by ventilating piglets with 8% oxygen and added CO2 to achieve hypercarbia. Hypotension was used to cause ischaemic damage and occurred as a result of the hypercarbic hypoxia.

Experimental Procedure:

The National Animal Research Authority, (NARA), approved the experimental protocol. The animals were cared for and handled in accordance with the European Guidelines for Use of Experimental Animals. The Norwegian Council for Animal Research approved the experimental protocol. The animals were cared for and handled in accordance with the European Guidelines for Use of Experimental Animals, by certified FELASA (Federation of European Laboratory Animals Science Association). Thirty-four newborn Noroc (LYxLD) pigs (12-36 h old) were included in the study. In addition we had a reference group consisting of 6 newborn pigs going through all procedures.

Surgical Preparation and Anesthesia.

Anesthesia was induced by giving Sevofluran 5% (Sevorane, Abbott); an ear vein was cannulated, the piglets were given Pentobarbital sodium 15 mg/kg and Fentanyl 50 µg/kg intravenously as a bolus injection. The piglets were orally intubated then placed on their back and washed for sterile procedures. Anesthesia was maintained by continuous infusion of Fentanyl (50 µg·kg-1·h-1) and Midazolam (0.25 mg·kg-1·h-1) in mixtures giving 1 ml/kg/h for each drug applied by IVAC P2000 infusion pump. When necessary, a bolus of Fentanyl (10 µg/kg), Midazolam (1 mg/kg) or Pentobarbital (2.5 mg/kg) was added (need for medication being defined as shivering, trigging on the respirator, increased tone assessed by passive movements of the limbs, increase in blood pressure and/or pulse). A continuous IV Infusion (Salidex: saline 0.3% and glucose 3.5%, 10 mL kg-1·h-1) was given until hypoxia and from 15 min after start of resuscitation and throughout the experiment.

The piglets were ventilated with a pressure-controlled ventilator (Babylog 8000+; Drägerwerk, Lübeck, Germany). Normoventilation (arterial carbon dioxide tension (PaCO2) 4.5-5.5 kPa) and a tidal volume of 6-8 mL/kg were achieved by adjusting the peak inspiratory pressure or ventilatory rate. Ventilatory rate was 15-40 respirations/min. Inspiratory time of 0.4 s and positive end-expiratory pressure of 4.5 cm H2O was kept constant throughout the experiment. Inspired fraction of O2 and end-tidal CO2 was monitored continuously (Datex Normocap Oxy; Datex, Helsinki, Finland).

The left femoral artery was cannulated with polyethylene catheters (Porex PE-50, inner diameter 0.58 mm; Porex Ltd Hythe, Kent, UK). Mean arterial bloodpressure (MABP) was measured continuously in the left femoral artery using BioPac systems MP150-CE. Rectal temperature was maintained between 38.5 and 39.5° C. with a heating blanket and a radiant heating lamp. One hour of stabilization was allowed after surgery. At the end of the experiment, the piglets were given an overdose of 150 mg/kg pentobarbital intravenously. (Eye enucleation at 15 (30 Gr 3) and 60 min)

Experimental Protocol:

Hypoxemia was achieved by ventilation with a gas mixture of 8% O2 in N2 until either mean arterial blood pressure decreased to 20 mm Hg or base excess (BE) reached −20 mM. CO2 was added during hypoxemia aiming at a $PaCO_2$ of 8.0-9.5 kPa, to imitate perinatal asphyxia. Before start of resuscitation, the hypoxic piglets were block-randomized for resuscitation with 21% or 100% oxygen for 15 min and then ventilation with room air for 45 min (group 1 and 2), or to receive 100% oxygen for 60 min (group 3). After initiating the reoxygenation, the piglets were kept normocapnic (PaCO2 4.5-5.5 kPa). Throughout the whole experiment there was a continuous surveillance of blood pressure, saturation, pulse, temperature and blood gas measurements. Hemoglobin was measured on a HemoCue Hb 201+ (HemoCue AB, Angelholm, Sweden) at baseline and at the end. Temperature-corrected arterial acid/base status and glucose were measured regularly throughout the experiment on a Blood Gas Analyzer 860 (Ciba Corning Diagnostics, Midfield, Mass., USA). Blood samples for Metabolomics were drawn before initiating the hypoxia, at the end of hypoxia and 60 min after initiating reoxygenation and handled according to the Biocrates protocol. Plasma or serum were prepared according to a standard protocol and then stored at minus 70° C. until subsequent analysis. All blood samples obtained from the femoral artery catheter were replaced by saline 1.5× the volume drawn. One hour after the end of hypoxia the animals were given an overdose of pentobarbital (150 mg/kg iv). The study staff and the laboratory personnel were blinded to the percentage oxygen administered by resuscitation.

Analytics:

Targeted metabolite profiling by ESI MS/MS was performed at Biocrates Life Sciences, Austria. The technique is described in detail by U.S. Patent 20070004044 (accessible online at http://www.freepatents online.com/20070004044.html). Briefly, a targeted profiling scheme is used to screen quantitatively for known small molecule metabolites using multiple reaction monitoring, neutral loss, and precursor ion scans. The quantification of the metabolites of the biological sample is achieved by reference to appropriate internal standards. The method is proven to be in conformance with Title 21 Code of Federal Regulations Part 11, and has been used in the past in different academic and industrial applications (2, 17). We used a multiparametric, highly robust, sensitive and high-throughput targeted metabolomic flow injection and LC-MS/MS method for the simultaneous quantification of endogenous intermediates namely amino acids, biogenic amines, acylcarnitines, sphingomyelins, hexoses, glycerophospholipids, small organic acids, and eicosanoids in brain samples enabling the determination of a broad range of target analytes. All procedures (sample handling, analytics) were performed by co-workers blinded to the groups.

Determination and quantification of oxysterols in biological samples by LC-MS/MS Oxysterols are determined by HPLC-Tandem mass spectrometer (HPLC-API-MS/MS) in positive detection mode using Multiple Reaction Mode (MRM).

20 μL samples, calibrators or internal standard mixture were placed into a capture plate and were protein precipitated by addition of 200 μL acetonitrile and centrifugation. 180 μL of the appropriate supernatants were transferred on a new filter plate with 7 mm filter spots and dried under a nitrogen stream. The analytes were hydrolyzed by addition of 100 μL 0.35 M KOH in 95% EtOH followed by a 2 h incubation in the dark. The reaction mixture was dried and washed three times with 200 μL water. The oxysterols were extracted with 100 μL 90% aqueous MeOH. 20 μL of the extracted sample are injected onto the HPLC-MS/MS system. Chromatographic separation and detection is performed by using a Zorbax Eclipse XDB C18, 150×2.0 mm, 3.5 μm HPLC-Column at a flow rate of 0.3 mL/min followed by electrospray ionization on the API4000 tandem mass spectrometer. For the quantitation the Analyst Quantitation software from Applied Biosystems was used.

Statistical Analysis:

All statistical calculations have been performed using the statistics software R(R: A Language and Environment for Statistical Computing, R Development Core Team, R Foundation for Statistical Computing, Vienna, Austria, 2008, ISBN 3-900051-07-0).

Analytes that were detected in at least 15% of the samples were selected for further analyses resulting in a list of 213 compounds/metabolites along with 28 known compound/metabolite sums and ratios (table 2).

The metabolic data is left censored due to thresholding of the mass spectrometer data resulting in non detected peak/signals. By a combination of metabolic pathway dynamism, complex sample molecular interaction and overall efficiency of the analytical protocol, replacement of missing data by means of a multivariate algorithm is preferred to a naive imputation by a pre-specified value like for instance zero. Hence, missing metabolite concentrations are replaced by the average value of the 6 closest samples to the one where the measurement is missing (impute: Imputation for microarray data, Hastie T., Tibshirani R., Narasimhan B. and Chu G., R package version 1.14.0).

At the exception of fold change (FC) determination, all statistical analyses are performed on preprocessed—that is, log transformed—data. The gls function in the package nlme (nlme: Linear and Nonlinear Mixed Effects Models, Pinheiro J., Bates D., DebRoy S., Sarkar D. and the R Core team, 2008, R package version 3.1-90) is used to compute the linear models specifying within treatment group heteroscedasticity structure and default parameters otherwise. Resulting p values are adjusted by the method described in Benjamini and Hochberg (Benjamini Y. and Hochberg Y., Controlling the false discovery rate: a practical and powerful approach to multiple testing, Journal of the Royal Statistical Society Series B, 1995, 57, 289-300) leading to so-called q values.

The results for comparing asphyxia with non-asphyxia are given in table 2 Results of the comparisons SA (start of asphyxia) vs. EA (end of asphyxia) and EA vs. ER (end of resuscitation) are displayed in FIGS. 1 to 3 where a q value threshold of 0.001 is set to select analytes. The depicted fold changes are computed from the median ratio original concentration between two time points and presented as changes compared to the control group (positive values) or to the treated group (negative values).

Sensitivity/specificity properties of a classifier comprising one analyte or a combination of analytes are summarised in terms of Area Under the Receiver Operating Characteristic Curve (AUC). The function colAUC (caTools: Tools: moving window statistics, GIF, Base64, ROC AUC, etc., Tuszynski J., 2008, R package version 1.9) is used to compute and plot ROC curves. Performance of single markers as well as of combinations of markers is assessed by Random Forest classification via the contributed R package randomForest (Classification and Regression by randomForest, Liaw A. and Wiener M., R News, 2002 2(3): 18-22). Predictive abilities of the models are computed using stratified boostrap (B=20) which was repeated 5 times to obtain a performance estimate and its associated variance (FIEmspro: Flow Injection Electrospray Mass Spectrometry Processing: data processing, classification modelling and variable selection in metabolite fingerprinting, Beckmann M., Enot D. and Lin W., 2007, R package version 1.1-0).

In table 2 the individual analytes and metabolites are ranked according to their discriminative power in terms of AUC for distinguishing asphyxia from non-asphyxia.

| Nr | Analyte | p value | q value | fold change | AUC |
|---|---|---|---|---|---|
| 1 | Suc | 0.00E+00 | 0.00E+00 | −5696.32 | 1.00 |
| 2 | C4 | 0.00E+00 | 0.00E+00 | −414.86 | 1.00 |
| 3 | Lac | 0.00E+00 | 0.00E+00 | −1192.31 | 1.00 |
| 4 | C16:1 | 2.66E−15 | 2.66E−14 | −217.65 | 1.00 |
| 5 | C16:2 | 5.55E−16 | 1.11E−14 | −280.00 | 0.99 |
| 6 | Putrescine | 5.45E−13 | 5.99E−12 | −360.57 | 0.99 |
| 7 | C10:2 | 2.55E−15 | 2.66E−14 | 90.20 | 0.99 |
| 8 | Spermine | 1.07E−11 | 3.93E−11 | −175.44 | 0.99 |
| 9 | Pyr + OAA | 7.12E−11 | 7.12E−11 | −177.05 | 0.99 |
| 10 | C5:1-DC | 1.37E−12 | 9.11E−12 | −112.50 | 0.98 |
| 11 | Glu/Gln | 2.06E−13 | 5.77E−12 | 298.09 | 0.98 |
| 12 | Spermidine | 6.11E−12 | 3.36E−11 | −337.86 | 0.98 |
| 13 | Gln | 7.87E−08 | 1.44E−06 | −112.10 | 0.97 |
| 14 | C18:2 | 3.18E−14 | 2.54E−13 | −225.18 | 0.97 |
| 15 | alpha-KGA | 5.01E−11 | 6.26E−11 | −187.63 | 0.96 |
| 16 | C5 | 3.03E−12 | 1.73E−11 | −248.87 | 0.96 |
| 17 | PC ae C40:3 | 3.63E−09 | 3.34E−07 | 57.58 | 0.96 |
| 18 | Asp/Asn | 1.70E−08 | 1.58E−07 | 191.33 | 0.95 |
| 19 | C14:2 | 7.71E−11 | 3.85E−10 | −203.03 | 0.95 |
| 20 | Lys | 2.36E−06 | 9.82E−05 | −277.51 | 0.95 |
| 21 | Fum | 0.00E+00 | 0.00E+00 | −852.86 | 0.94 |
| 22 | C3 | 1.31E−10 | 5.74E−10 | −286.23 | 0.94 |
| 23 | Orn/Cit | 1.52E−08 | 1.58E−07 | −100.98 | 0.94 |
| 24 | lysoPC a C16:0.K1 | 1.98E−08 | 9.11E−07 | 80.78 | 0.93 |
| 25 | C18:1.K1 | 1.43E−10 | 5.74E−10 | −277.89 | 0.93 |
| 26 | C14:2-OH.K1 | 9.66E−08 | 2.97E−07 | −39.73 | 0.92 |
| 27 | Ala.K2 | 1.56E−07 | 1.44E−06 | −155.53 | 0.92 |
| 28 | Pro.K2 | 1.73E−07 | 1.44E−06 | −85.34 | 0.92 |
| 29 | Ala/BCAA | 3.95E−08 | 2.77E−07 | −102.36 | 0.92 |
| 30 | C16:2-OH.K1 | 5.14E−07 | 1.37E−06 | −30.77 | 0.91 |
| 31 | lysoPC a C17:0.K1 | 8.11E−08 | 2.49E−06 | 98.90 | 0.91 |
| 32 | His.K2 | 7.51E−07 | 3.82E−06 | −114.09 | 0.91 |
| 33 | PC ae C30:0.K1 | 2.70E−06 | 6.21E−05 | 58.30 | 0.91 |
| 34 | SumLyso | 5.75E−07 | 2.68E−06 | 31.94 | 0.91 |
| 35 | Putrescine/Orn | 8.86E−08 | 4.96E−07 | −250.65 | 0.91 |
| 36 | Phe.K2 | 7.64E−07 | 3.82E−06 | −55.79 | 0.91 |
| 37 | C12.K1 | 2.09E−08 | 7.61E−08 | −68.63 | 0.90 |
| 38 | TCDCA.BA | 4.69E−07 | 1.64E−06 | −507.88 | 0.89 |
| 39 | lysoPC a C18:0.K1 | 6.00E−06 | 6.39E−05 | 72.70 | 0.88 |
| 40 | PC ae C42:5.K1 | 5.50E−06 | 6.39E−05 | 27.28 | 0.88 |
| 41 | SumSFA | 9.69E−06 | 3.39E−05 | 26.85 | 0.88 |
| 42 | GCDCA.BA | 1.17E−06 | 2.73E−06 | −706.02 | 0.88 |
| 43 | Asn.K2 | 2.18E−05 | 6.80E−05 | −54.57 | 0.87 |
| 44 | C6 (C4:1-DC).K1 | 2.23E−06 | 5.58E−06 | −27.10 | 0.87 |
| 45 | PC aa C40:3.K1 | 1.26E−05 | 1.16E−04 | 74.34 | 0.87 |
| 46 | PC ae C38:4.K1 | 5.92E−06 | 6.39E−05 | 73.56 | 0.87 |
| 47 | C9.K1 | 4.06E−06 | 9.56E−06 | −38.05 | 0.86 |
| 48 | Leu.K2 | 2.11E−04 | 5.26E−04 | −35.04 | 0.86 |
| 49 | Val.K2 | 3.45E−05 | 9.59E−05 | −46.32 | 0.86 |
| 50 | lysoPC a C16:1.K1 | 3.78E−06 | 6.39E−05 | 48.21 | 0.86 |
| 51 | C14.K1 | 7.65E−08 | 2.55E−07 | −161.22 | 0.86 |
| 52 | Spermine/Spermidine | 4.86E−06 | 1.95E−05 | 77.81 | 0.85 |
| 53 | PC aa C40:4.K1 | 2.57E−05 | 1.97E−04 | 69.07 | 0.85 |
| 54 | C18:1-OH.K1 | 4.32E−05 | 9.09E−05 | −31.10 | 0.85 |
| 55 | C5:1.K1 | 2.70E−07 | 7.72E−07 | −39.33 | 0.85 |
| 56 | C2.K1 | 8.46E−05 | 1.69E−04 | −51.90 | 0.85 |
| 57 | Glu.K2 | 1.75E−05 | 6.27E−05 | 112.21 | 0.84 |
| 58 | PC ae C38:5.K1 | 3.72E−04 | 1.43E−03 | 39.85 | 0.84 |
| 59 | AA.PA | 2.31E−04 | 6.92E−04 | 88.68 | 0.84 |
| 60 | PC aa C42:4.K1 | 6.25E−06 | 6.39E−05 | 86.78 | 0.84 |
| 61 | PC aa C38:6.K1 | 7.04E−05 | 4.99E−04 | 47.20 | 0.83 |
| 62 | SumPC + Lyso | 9.62E−05 | 2.69E−04 | 28.81 | 0.83 |
| 63 | PC ae C40:6.K1 | 2.46E−04 | 1.08E−03 | 58.76 | 0.83 |
| 64 | PC ae C40:4.K1 | 2.43E−05 | 1.97E−04 | 50.81 | 0.83 |
| 65 | SM C26:1.K1 | 3.75E−05 | 5.63E−04 | 30.27 | 0.83 |
| 66 | PC aa C40:6.K1 | 1.42E−04 | 7.68E−04 | 70.46 | 0.83 |
| 67 | SM (OH) C16:1.K1 | 6.24E−04 | 4.68E−03 | 54.87 | 0.83 |
| 68 | PC ae C40:5.K1 | 1.23E−04 | 7.68E−04 | 65.13 | 0.82 |
| 69 | PC ae C42:4.K1 | 1.31E−04 | 7.68E−04 | 66.61 | 0.82 |
| 70 | Orn/Arg | 1.52E−04 | 3.54E−04 | −50.90 | 0.82 |
| 71 | PC ae C36:4.K1 | 4.39E−04 | 1.61E−03 | 43.98 | 0.82 |
| 72 | PC aa C40:5.K1 | 3.11E−04 | 1.30E−03 | 68.04 | 0.82 |
| 73 | PC aa C40:2.K1 | 1.41E−04 | 7.68E−04 | 19.89 | 0.82 |
| 74 | GCA.BA | 5.07E−08 | 3.55E−07 | −1090.38 | 0.81 |
| 75 | SumPUFA | 2.46E−04 | 5.29E−04 | 30.54 | 0.81 |
| 76 | SumPC | 2.77E−04 | 5.54E−04 | 31.55 | 0.81 |
| 77 | C14:1-OH.K1 | 3.40E−04 | 5.95E−04 | −49.02 | 0.81 |
| 78 | PC aa C38:4.K1 | 2.22E−04 | 1.05E−03 | 43.70 | 0.81 |
| 79 | Serotonin/Trp | 8.72E−05 | 2.69E−04 | 172.55 | 0.81 |
| 80 | C14:1.K1 | 3.35E−05 | 7.44E−05 | −105.36 | 0.81 |
| 81 | PC aa C36:6.K1 | 1.73E−04 | 8.85E−04 | 51.15 | 0.81 |
| 82 | PC ae C30:1.K1 | 6.69E−04 | 2.30E−03 | 38.62 | 0.80 |
| 83 | C16:1-OH.K1 | 1.13E−04 | 2.15E−04 | −49.02 | 0.80 |
| 84 | PC ae C38:3.K1 | 3.35E−04 | 1.34E−03 | 36.15 | 0.80 |
| 85 | PC ae C38:6.K1 | 1.90E−03 | 4.73E−03 | 38.08 | 0.80 |
| 86 | Orn.K2 | 3.78E−04 | 8.58E−04 | −33.69 | 0.80 |
| 87 | PC ae C32:2.K1 | 2.09E−04 | 4.85E−04 | 39.84 | 0.79 |
| 88 | SumSM | 1.39E−03 | 2.16E−03 | 16.91 | 0.79 |
| 89 | PC ae C38:1.K1 | 8.82E−04 | 2.80E−03 | 23.52 | 0.79 |
| 90 | PC ae C34:1.K1 | 8.62E−04 | 2.80E−03 | 30.70 | 0.79 |
| 91 | PC aa C36:4.K1 | 2.29E−04 | 1.05E−03 | 38.45 | 0.78 |
| 92 | PC aa C30:2.K1 | 1.42E−03 | 4.16E−03 | 35.49 | 0.78 |
| 93 | C16-OH.K1 | 3.42E−04 | 5.95E−04 | −15.56 | 0.78 |
| 94 | SumMUFA | 7.92E−04 | 1.48E−03 | 19.84 | 0.78 |
| 95 | PC ae C30:2.K1 | 2.99E−03 | 6.26E−03 | 18.49 | 0.78 |
| 96 | PC aa C28:1.K1 | 2.61E−03 | 5.58E−03 | 36.44 | 0.78 |
| 97 | lysoPC a C24:0.K1 | 1.45E−03 | 4.16E−03 | 16.81 | 0.78 |
| 98 | PC ae C42:3.K1 | 1.61E−03 | 4.34E−03 | 71.88 | 0.78 |
| 99 | Kyn/Trp | 1.11E−03 | 1.82E−03 | 38.72 | 0.78 |
| 100 | Serotonin.K2 | 6.15E−04 | 1.69E−03 | 226.02 | 0.77 |
| 101 | C12:1.K1 | 2.04E−03 | 3.26E−03 | −13.07 | 0.77 |
| 102 | Met-SO.K2 | 9.96E−06 | 2.08E−05 | 104.16 | 0.77 |
| 103 | lysoPC a C28:0.K1 | 2.04E−03 | 4.85E−03 | 13.52 | 0.77 |
| 104 | PC ae C40:2.K1 | 1.44E−03 | 4.16E−03 | 27.36 | 0.77 |
| 105 | C16 + C18/C0 | 1.42E−04 | 3.54E−04 | −99.53 | 0.77 |
| 106 | PC aa C38:5.K1 | 1.75E−03 | 4.46E−03 | 36.62 | 0.76 |
| 107 | PC ae C36:0.K1 | 2.39E−03 | 5.23E−03 | 24.93 | 0.76 |
| 108 | UDCA.BA | 1.01E−03 | 1.77E−03 | −269.98 | 0.76 |
| 109 | SM (OH) C22:1.K1 | 1.81E−03 | 4.91E−03 | 27.15 | 0.76 |
| 110 | PC aa C42:5.K1 | 6.74E−04 | 2.30E−03 | 57.93 | 0.76 |
| 111 | Cit.K2 | 1.05E−02 | 1.38E−02 | 48.41 | 0.76 |
| 112 | SM (OH) C22:2.K1 | 2.59E−03 | 5.55E−03 | 27.12 | 0.76 |
| 113 | SM (OH) C24:1.K1 | 1.56E−03 | 4.91E−03 | 15.39 | 0.76 |
| 114 | C16.K1 | 5.45E−04 | 9.08E−04 | −97.85 | 0.76 |
| 115 | PC ae C34:0.K1 | 2.32E−03 | 5.20E−03 | 28.79 | 0.75 |
| 116 | PC aa C38:3.K1 | 1.67E−03 | 4.39E−03 | 37.57 | 0.75 |
| 117 | Asp.EM | 1.08E−03 | 2.09E−03 | 78.57 | 0.75 |
| 118 | Gly/BCAA | 9.57E−04 | 1.68E−03 | 36.18 | 0.75 |
| 119 | PC aa C42:1.K1 | 3.25E−03 | 6.50E−03 | 13.03 | 0.75 |
| 120 | PC ae C36:5.K1 | 7.76E−03 | 1.27E−02 | 26.17 | 0.75 |
| 121 | lysoPC a C20:4.K1 | 1.58E−03 | 4.34E−03 | 44.44 | 0.75 |
| 122 | PC aa C36:3.K1 | 3.82E−03 | 7.32E−03 | 25.64 | 0.74 |
| 123 | PC ae C36:2.K1 | 5.88E−03 | 1.02E−02 | 20.16 | 0.74 |
| 124 | PC ae C32:1.K1 | 3.19E−03 | 6.50E−03 | 32.59 | 0.74 |
| 125 | Met.K2 | 2.21E−03 | 3.69E−03 | 51.90 | 0.74 |
| 126 | PC aa C38:0.K1 | 3.51E−03 | 6.88E−03 | 27.68 | 0.74 |

-continued

| Nr | Analyte | p value | q value | fold change | AUC |
|---|---|---|---|---|---|
| 127 | SM (OH) C14:1.K1 | 1.84E-02 | 1.97E-02 | 38.66 | 0.74 |
| 128 | C5-DC (C6-OH).K1 | 4.17E-03 | 6.18E-03 | -28.57 | 0.74 |
| 129 | SM C22:3.K1 | 3.70E-03 | 6.16E-03 | 23.10 | 0.74 |
| 130 | Asp.K2 | 5.09E-03 | 7.96E-03 | 46.91 | 0.74 |
| 131 | SM C26:0.K1 | 1.31E-03 | 4.91E-03 | 15.09 | 0.74 |
| 132 | PC ae C40:1.K1 | 4.91E-03 | 9.22E-03 | 48.11 | 0.74 |
| 133 | PC aa C40:1.K1 | 2.11E-03 | 4.85E-03 | 9.62 | 0.74 |
| 134 | PUFA/MUFA | 1.00E-02 | 1.34E-02 | 7.80 | 0.74 |
| 135 | C18.K1 | 1.84E-02 | 2.54E-02 | -70.54 | 0.74 |
| 136 | C3-OH.K1 | 2.34E-03 | 3.60E-03 | -21.05 | 0.73 |
| 137 | Tyr.K2 | 6.81E-03 | 9.52E-03 | -34.18 | 0.73 |
| 138 | PC aa C36:5.K1 | 6.94E-03 | 1.16E-02 | 22.53 | 0.73 |
| 139 | Ser.K2 | 1.83E-03 | 3.27E-03 | -18.88 | 0.72 |
| 140 | PC ae C42:2.K1 | 5.45E-03 | 1.00E-02 | 50.72 | 0.72 |
| 141 | SM C24:1.K1 | 1.96E-03 | 4.91E-03 | 14.69 | 0.72 |
| 142 | SM C16:1.K1 | 4.62E-03 | 6.31E-03 | 34.79 | 0.72 |
| 143 | PC ae C38:2.K1 | 9.29E-03 | 1.42E-02 | 15.20 | 0.72 |
| 144 | Ala/Lys | 3.30E-03 | 4.86E-03 | 33.04 | 0.72 |
| 145 | PC ae C40:0.K1 | 8.10E-03 | 1.29E-02 | 13.45 | 0.72 |
| 146 | Histamine.K2 | 1.56E-02 | 2.45E-02 | 119.64 | 0.72 |
| 147 | C4-OH (C3-DC).K1 | 1.76E-02 | 2.52E-02 | -28.30 | 0.72 |
| 148 | PC ae C44:4.K1 | 2.49E-02 | 3.18E-02 | 40.91 | 0.72 |
| 149 | Xle.K2 | 6.86E-03 | 9.52E-03 | -11.85 | 0.71 |
| 150 | SM C24:0.K1 | 3.11E-03 | 5.84E-03 | 13.86 | 0.71 |
| 151 | PC ae C34:2.K1 | 6.59E-03 | 1.12E-02 | 29.21 | 0.71 |
| 152 | SM C18:1.K1 | 1.85E-02 | 1.97E-02 | 19.23 | 0.71 |
| 153 | C8.K1 | 2.62E-02 | 3.38E-02 | -7.69 | 0.71 |
| 154 | SM C16:0.K1 | 4.37E-03 | 6.31E-03 | 29.12 | 0.71 |
| 155 | C8:1.K1 | 2.16E-02 | 2.88E-02 | 8.09 | 0.71 |
| 156 | PC aa C42:0.K1 | 1.46E-02 | 2.03E-02 | 18.21 | 0.71 |
| 157 | PC aa C42:2.K1 | 8.09E-03 | 1.29E-02 | 8.94 | 0.71 |
| 158 | total DMA.K2 | 1.29E-02 | 2.45E-02 | -21.58 | 0.71 |
| 159 | PC aa C32:3.K1 | 1.18E-02 | 1.78E-02 | 27.73 | 0.71 |
| 160 | PC ae C42:1.K1 | 1.23E-02 | 1.82E-02 | 30.08 | 0.70 |
| 161 | PC ae C36:1.K1 | 1.96E-02 | 2.57E-02 | 16.68 | 0.70 |
| 162 | PC aa C42:6.K1 | 5.71E-03 | 1.01E-02 | 25.85 | 0.70 |
| 163 | 24,25,EPC | 7.99E-01 | 8.07E-01 | 12.79 | 0.70 |
| 164 | SM C20:2.K1 | 1.97E-02 | 1.97E-02 | 27.85 | 0.70 |
| 165 | Cit/Arg | 1.80E-02 | 2.29E-02 | 31.23 | 0.70 |
| 166 | lysoPC a C20:3.K1 | 8.27E-03 | 1.29E-02 | 12.94 | 0.70 |
| 167 | PC ae C38:0.K1 | 1.25E-02 | 1.83E-02 | 26.76 | 0.69 |
| 168 | Kyn/OHKyn | 6.67E-03 | 9.34E-03 | -20.64 | 0.69 |
| 169 | PC aa C30:0.K1 | 1.87E-02 | 2.50E-02 | 12.41 | 0.69 |
| 170 | PC aa C32:2.K1 | 1.53E-02 | 2.09E-02 | 20.96 | 0.69 |
| 171 | PC aa C34:2.K1 | 1.30E-02 | 1.87E-02 | 31.29 | 0.69 |
| 172 | PC aa C38:1.K1 | 5.70E-03 | 1.01E-02 | 9.65 | 0.69 |
| 173 | PC ae C44:3.K1 | 2.75E-02 | 3.42E-02 | 23.94 | 0.69 |
| 174 | PC aa C34:4.K1 | 1.61E-02 | 2.18E-02 | 34.70 | 0.69 |
| 175 | Hex.EM | 4.11E-01 | 4.94E-01 | -58.08 | 0.68 |
| 176 | PC aa C24:0.K1 | 1.98E-02 | 2.57E-02 | 23.18 | 0.67 |
| 177 | DHA.PA | 4.14E-01 | 4.14E-01 | 29.63 | 0.67 |
| 178 | Desmosterol | 6.94E-02 | 3.39E-01 | 27.78 | 0.67 |
| 179 | PC aa C26:0.K1 | 1.23E-01 | 1.37E-01 | 3.05 | 0.66 |
| 180 | Ile.K2 | 7.40E-02 | 8.89E-02 | 34.37 | 0.66 |
| 181 | C5-OH (C3-DC-M).K1 | 1.25E-01 | 1.52E-01 | 7.30 | 0.66 |
| 182 | OH-Kyn.K2 | 1.55E-02 | 2.45E-02 | 36.61 | 0.66 |
| 183 | 24SOHC | 7.83E-02 | 3.39E-01 | -14.88 | 0.66 |
| 184 | C3:1.K1 | 3.81E-02 | 4.76E-02 | 20.00 | 0.66 |
| 185 | lysoPC a C18:2.K1 | 2.87E-02 | 3.52E-02 | 26.65 | 0.66 |
| 186 | lysoPC a C18:1.K1 | 2.73E-02 | 3.42E-02 | 18.24 | 0.66 |
| 187 | PC ae C44:5.K1 | 2.34E-01 | 2.53E-01 | 17.90 | 0.65 |
| 188 | SM C18:0.K1 | 1.92E-02 | 1.97E-02 | 22.56 | 0.65 |
| 189 | Creatinine.K2 | 6.20E-01 | 6.20E-01 | -17.92 | 0.65 |
| 190 | lysoPC a C14:0.K1 | 1.39E-02 | 1.97E-02 | 4.70 | 0.65 |
| 191 | H1.K1 | 4.94E-02 | 4.94E-02 | -32.61 | 0.64 |
| 192 | 5a,6a,EPC | 2.58E-02 | 4.79E-02 | 17.09 | 0.64 |
| 193 | lysoPC a C28:1.K1 | 9.06E-02 | 1.06E-01 | 5.15 | 0.64 |
| 194 | 24DHLan | 7.05E-02 | 8.07E-01 | -48.05 | 0.63 |
| 195 | 27OHC | 3.37E-01 | 5.31E-01 | 8.09 | 0.63 |
| 196 | 4BOHC | 2.07E-02 | 4.78E-02 | 6.74 | 0.62 |
| 197 | C0.K1 | 2.50E-01 | 2.94E-01 | 14.29 | 0.62 |
| 198 | Met-SO/Met | 1.71E-02 | 2.09E-02 | 5.92 | 0.62 |
| 199 | PC aa C34:1.K1 | 5.28E-02 | 6.30E-02 | 7.59 | 0.62 |
| 200 | 25OHC | 1.81E-02 | 4.78E-02 | -7.93 | 0.61 |
| 201 | PUFA/SFA | 2.83E-01 | 3.30E-01 | 5.28 | 0.61 |
| 202 | SDMA.K2 | 1.18E-01 | 1.62E-01 | -4.80 | 0.61 |
| 203 | 5B,6B,EPC | 4.66E-01 | 6.06E-01 | 6.39 | 0.60 |
| 204 | C7-DC.K1 | 3.24E-01 | 3.60E-01 | -7.14 | 0.60 |
| 205 | Trp.K2 | 7.47E-02 | 8.89E-02 | -0.48 | 0.60 |
| 206 | PC aa C34:3.K1 | 1.04E-01 | 1.19E-01 | 27.33 | 0.60 |
| 207 | PC aa C32:1.K1 | 1.12E-01 | 1.26E-01 | 4.43 | 0.60 |
| 208 | PC ae C34:3.K1 | 1.05E-01 | 1.19E-01 | 4.96 | 0.59 |
| 209 | CDCA.BA | 3.81E-01 | 3.81E-01 | -81.76 | 0.59 |
| 210 | PC aa C36:2.K1 | 1.31E-01 | 1.44E-01 | 7.07 | 0.59 |
| 211 | Cholestenone | 5.20E-02 | 3.39E-01 | 17.96 | 0.58 |
| 212 | PC aa C36:3.K1 | 2.89E-01 | 3.05E-01 | 6.38 | 0.58 |
| 213 | LCA.BA | 2.05E-01 | 2.40E-01 | -57.99 | 0.58 |
| 214 | Gly.K2 | 4.32E-01 | 4.70E-01 | 14.56 | 0.58 |
| 215 | PC ae C44:6.K1 | 2.52E-01 | 2.69E-01 | 2.62 | 0.57 |
| 216 | 13S-HODE.PA | 2.15E-01 | 3.23E-01 | -3.40 | 0.57 |
| 217 | 7aOHC | 3.68E-01 | 5.31E-01 | 7.07 | 0.57 |
| 218 | CA.BA | 4.71E-03 | 6.60E-03 | -581.92 | 0.57 |
| 219 | PC aa C36:1.K1 | 7.48E-02 | 8.82E-02 | 1.18 | 0.57 |
| 220 | C10:1.K1 | 3.18E-01 | 3.60E-01 | 9.43 | 0.57 |
| 221 | 7DHC | 2.21E-01 | 4.78E-01 | 15.98 | 0.57 |
| 222 | C4:1.K1 | 3.98E-01 | 4.31E-01 | 30.36 | 0.57 |
| 223 | SumSMOH/SumSM | 6.05E-01 | 6.28E-01 | -3.64 | 0.56 |
| 224 | Kyn.K2 | 5.90E-01 | 6.20E-01 | 12.50 | 0.56 |
| 225 | Phe/Tyr | 8.25E-01 | 8.25E-01 | 16.64 | 0.56 |
| 226 | lysoPC a C26:1.K1 | 5.91E-01 | 6.05E-01 | 1.56 | 0.56 |
| 227 | PC aa C32:0.K1 | 3.93E-01 | 4.11E-01 | -0.61 | 0.56 |
| 228 | PC ae C42:0.K1 | 4.01E-01 | 4.14E-01 | -0.46 | 0.55 |
| 229 | PC aa C36:0.K1 | 4.85E-01 | 5.87E-02 | 0.77 | 0.55 |
| 230 | MUFA/SFA | 4.20E-01 | 4.71E-01 | 1.34 | 0.55 |
| 231 | Lanosterol | 8.07E-01 | 8.07E-01 | -3.53 | 0.55 |
| 232 | Arg.K2 | 9.53E-01 | 9.53E-01 | 29.91 | 0.54 |
| 233 | lysoPC a C26:0.K1 | 9.87E-01 | 9.87E-01 | 1.56 | 0.54 |
| 234 | SDMA/ADMA | 5.49E-01 | 5.92E-01 | 12.14 | 0.54 |
| 235 | ADMA.K2 | 3.78E-01 | 4.62E-01 | 1.32 | 0.53 |
| 236 | C12-DC.K1 | 4.22E-01 | 4.44E-01 | 1.12 | 0.53 |
| 237 | C6:1.K1 | 6.12E-01 | 6.12E-01 | 3.57 | 0.52 |
| 238 | lysoPC a C6:0.K1 | 6.14E-01 | 6.20E-01 | -7.69 | 0.52 |
| 239 | Arg.EM | 8.76E-01 | 9.13E-01 | -12.65 | 0.51 |
| 240 | Thr.K2 | 2.52E-01 | 2.87E-01 | 15.28 | 0.51 |
| 241 | C10.K1 | 5.87E-01 | 6.02E-01 | 1.77 | 0.51 |

Table 2 depicts the ranks of the individual analytes and metabolites in terms of AUC distinguishing asphyxia from non-asphyxia. Moreover p values, q values (i.e., adjusted p values) and fold changes are given. For additional information see also FIGS. 1-3.

Figure 4C:
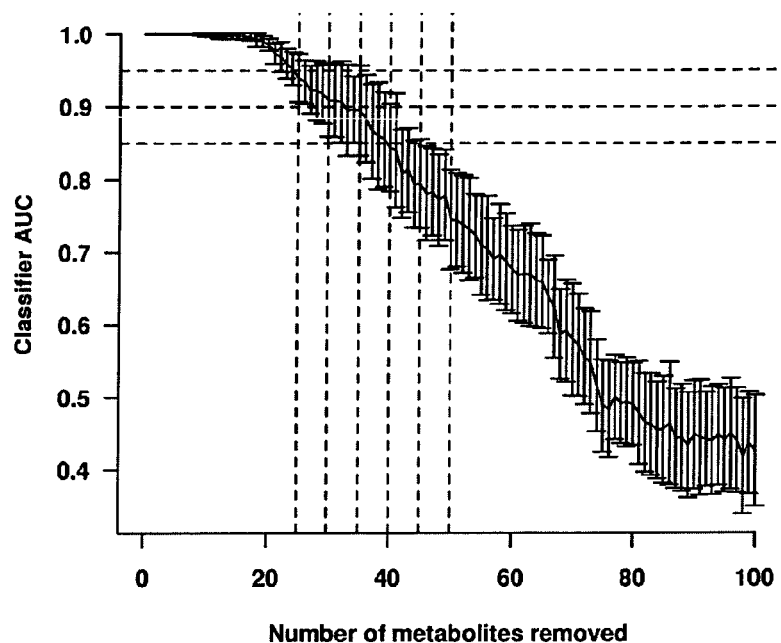

Due to the high predictive power for distinguishing asphyxia and non-asphyxia of several analytes and metabolites taken alone (cf. table 2) which is confirmed by principal component analyses (PCA) with and without the 30 top ranked metabolites (cf. FIGS. 4a and 4b), a backward strategy is employed to decide on an optimal feature subset. Successive models are constructed by iterative removal of metabolites according to a relevance score calculated by means of a t test; i.e., by a so-called filter/ranker. At each step, classification accuracy is computed by bootstrapping (cf. FIG. 4c).

Figure 5:
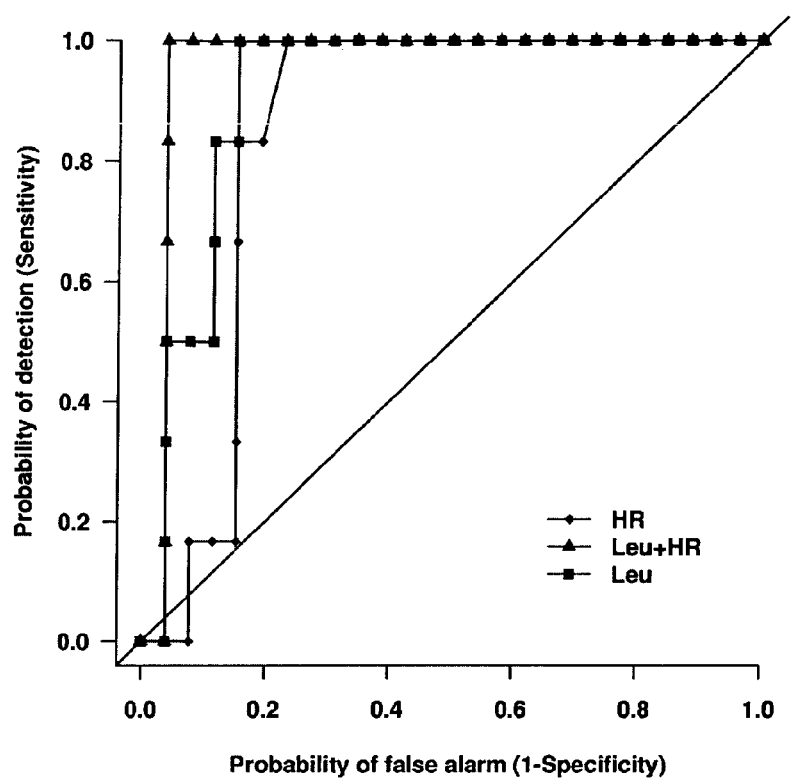
FIG. 5 shows receiver operator characteristics curves: an individual clinical parameter (heart rate, HR), a predictive metabolite from table 1 and the combination of these two to discriminate healthy and asphyxiated subjects.

In addition, the receiver operator characteristics (ROC) curves plotted in FIG. 5 provide evidence that the combination of a predictive metabolite (e.g., Leu) of table 1 with an individual clinical parameter (e.g., heart rate) provides a way to increase sensitivity and specificity for distinguishing asphyxia from non-asphyxia.

For assessing the duration of hypoxia regression models (as described above) are used. A full list of the results is given in table 4. In FIG. 6 the actual versus the fitted hypoxia length involving the commonly used marker lactate (grey asterisks), the Gly/BCAA ratio and a combination of three metabolomics parameters are displayed. As the results in FIG. 6 show, the predictive power of the Gly/BCAA ratio and the combination of three metabolomics parameters is clearly larger than that of lactate. In particular, the combination of the three metabolomics parameters leads to a nearly perfect fit of the hypoxia length.

For testing the effectiveness of reoxygenation, three groups of animals were selected after asphyxia was experimentally induced as described above:
Group 1: 21% $O_2$, 15 min
Group 2: 100% $O_2$, 15 min, followed by 45 min 21% $O_2$
Group 3: 100% $O_2$, 60 min.

The regression analyses were followed by post hoc analyses using the Tukey's Honest Significant Difference method. The results in table 5 for instance indicate that C10:2 concentration ratios in group 3 are significantly higher than in group 1 and that C3 concentration ratios are significantly higher in group 2 than in group 1 (cf. FIGS. 7a and 7b, table 5). Without achieving adequate statistical significance, the behaviour of C3 can be extended to several compounds analogous to C3 partly due to a relative degree of correlation between concentrations and/or metabolic relatedness. A list of all results of the post hoc analyses is given in table 5.

Finally, linear discriminant analyses (LDA) are conducted. Because of the low sample size (7 to 10 piglets per group), models including no more than two features are examined to limit over-fitting and consequently avoid over-optimistic interpretation. The models are compared according to the bootstrap 0.632+ accuracy (with B=20) averaged over 5 independent runs. Accuracies from the classifiers built using either only C10:2 or only C3 are 58% and 48%, respectively. These accuracies can be increased to 73% by combining C3 and C10:2. These results show that combinations of analytes offer a meaningful description of resuscitation group differences with higher discriminative power than single analytes.

TABLE 3

Cholesterol-derived Analytes

| BC Code | Common Name | Systematic Name | CAS Registry Number |
|---|---|---|---|
| 22ROHC | 22-R-Hydroxycholesterol | Cholest-5-ene-3,22-diol, (3beta,22R)- | 17954-98-2 |
| 24SOHC | 24-S-Hydroxycholesterol | Cholest-5-ene-3,24-diol, (3beta,24S)- | 474-73-7 |
| 25OHC | 25-Hydroxycholesterol | Cholest-5-ene-3beta,25-diol | 2140-46-7 |
| 27OHC | 27-Hydroxycholesterol | Cholest-5-ene-3,26,diol, (3beta,25R)- | 20380-11-4 |
| 20aOHC | 20α-Hydroxycholesterol | Cholest-5-ene-3beta,20-diol, (20S)- | 516-72-3 |
| 22SOHC | 22S-Hydroxycholesterol | Cholest-5-ene-3,22-diol, (3beta,22S)- | 22348-64-7 |
| 24,25EC | 24,25-Epoxycholesterol | Cholestan-3-ol, 24,25-epoxy-, (3alpha,5beta)- | 68138-65-8 |
| 3B,5a,6BTHC | 3β,5α,6β-Trihydroxycholestan | Cholestane-3beta,5alpha,6beta-triol | 1253-84-5 |
| 7aOHC | 7α-Hydroxycholesterol | Cholest-5-ene-3,7-diol, (3beta,7alpha)- | 566-26-7 |
| 7KC | 7-Ketocholesterol | Cholest-5-en-7-one, 3-hydroxy-, (3-beta)- | 566-28-9 |
| 5B,6B,EC | 5β,6β-Epoxycholesterol | Cholestan-3-ol, 5,6-epoxy-, (3beta,5beta,6beta)- | 4025-59-6 |
| 5a,6a,EC | 5α,6α-Epoxycholesterol | Cholestan-3-ol, 5,6-epoxy-, (3beta,5alpha,6alpha)- | 2953-38-0 |
| 4BOHC | 4β-Hydroxycholesterol | Cholest-5-ene-3,4-diol, (3beta,4beta)- | 17320-10-4 |
| Desmosterol | Desmosterol | Cholesta-5,24-dien-3-ol, (3beta)- | 313-04-2 |
| 7DHC | 7-Dehydrocholesterol | Cholesta-5,7-dien-3-ol, (3beta)- | 434-16-2 |
| Cholestenone | Cholestenone | Cholest-5-en-3-one | 601-54-7 |
| Lanosterol | Lanosterol | Lanosta-8,24-dien-3-ol, (3beta)- | 79-63-0 |
| 24DHLan | 24-Dihydrolanosterol | (3beta)-Lanost-8-en-3-ol | 79-62-9 |

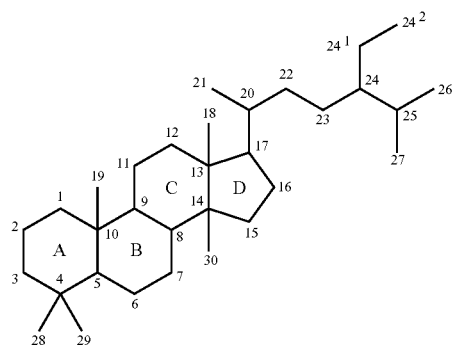

Table 3 Numbering of the cholesterol compounds in table 3 is evident from the above numbered structural formula. The compounds listed in table 3 are particular useful for assessing duration of hypoxia and/or for assessing oxygenation status of the subjects after and/or during resuscitation (cf. tables 4 and 5)

TABLE 4

Duration of hypoxia; p values and q values (i.e., adjusted p values) of regression analyses are given.

| | | Duration of hypoxia | | Gender effect | | Interaction | |
|---|---|---|---|---|---|---|---|
| Nr | Analyte | p value | q value | p value | q value | p value | q value |
| 1 | C0.K1 | 1.20E−01 | 3.42E−01 | 4.06E−01 | 7.11E−01 | 6.50E−01 | 8.76E−01 |
| 2 | C10.K1 | 4.45E−04 | 2.54E−03 | 2.64E−01 | 5.48E−01 | 9.96E−01 | 9.96E−01 |
| 3 | C10:1.K1 | 3.67E−01 | 6.56E−01 | 8.79E−01 | 9.50E−01 | 7.96E−01 | 9.22E−01 |
| 4 | C10:2.K1 | 1.93E−02 | 7.99E−02 | 4.35E−01 | 7.20E−01 | 9.79E−01 | 9.88E−01 |
| 5 | C12.K1 | 2.50E−10 | 5.00E−09 | 2.25E−01 | 5.06E−01 | 4.95E−01 | 7.61E−01 |
| 6 | C12-DC.K1 | 5.73E−01 | 8.19E−01 | 5.07E−01 | 7.61E−01 | 8.73E−01 | 9.50E−01 |
| 7 | C12:1.K1 | 8.39E−02 | 2.72E−01 | 9.22E−01 | 9.70E−01 | 8.72E−01 | 9.50E−01 |
| 8 | C14.K1 | 4.55E−05 | 2.87E−04 | 2.65E−01 | 5.48E−01 | 8.87E−01 | 9.50E−01 |
| 9 | C14:1.K1 | 2.93E−07 | 2.71E−06 | 4.31E−01 | 7.20E−01 | 2.08E−01 | 4.81E−01 |
| 10 | C14:1-OH.K1 | 1.27E−01 | 3.45E−01 | 7.73E−01 | 9.09E−01 | 3.30E−01 | 6.09E−01 |
| 11 | C14:2.K1 | 1.37E−11 | 3.29E−10 | 4.09E−01 | 7.11E−01 | 7.87E−02 | 2.62E−01 |
| 12 | C14:2-OH.K1 | 8.50E−05 | 5.10E−04 | 2.55E−01 | 5.48E−01 | 8.55E−01 | 9.50E−01 |
| 13 | C16.K1 | 1.50E−09 | 1.64E−08 | 2.01E−01 | 4.72E−01 | 7.16E−01 | 8.91E−01 |
| 14 | C16-OH.K1 | 6.72E−03 | 3.10E−02 | 8.93E−02 | 2.75E−01 | 9.34E−01 | 9.70E−01 |
| 15 | C16:1.K1 | 1.27E−11 | 3.29E−10 | 1.61E−01 | 4.04E−01 | 3.02E−01 | 6.04E−01 |
| 16 | C16:1-OH.K1 | 3.88E−05 | 2.59E−04 | 2.58E−01 | 5.48E−01 | 7.21E−01 | 8.91E−01 |
| 17 | C16:2.K1 | 7.57E−10 | 1.14E−08 | 4.71E−02 | 1.61E−01 | 5.70E−03 | 2.74E−02 |
| 18 | C16:2-OH.K1 | 3.13E−05 | 2.21E−04 | 6.45E−01 | 8.76E−01 | 6.35E−01 | 8.75E−01 |
| 19 | C18.K1 | 2.31E−07 | 2.31E−06 | 2.28E−01 | 5.06E−01 | 8.01E−01 | 9.22E−01 |
| 20 | C18:1.K1 | 7.52E−10 | 1.14E−08 | 7.26E−01 | 8.91E−01 | 3.30E−01 | 6.09E−01 |
| 21 | C18:1-OH.K1 | 9.40E−04 | 4.90E−03 | 1.03E−01 | 3.01E−01 | 6.33E−01 | 8.75E−01 |
| 22 | C18:2.K1 | 2.31E−13 | 9.25E−12 | 4.42E−01 | 7.20E−01 | 4.60E−02 | 1.61E−01 |
| 23 | C2.K1 | 5.82E−06 | 4.66E−05 | 8.88E−02 | 2.75E−01 | 5.14E−01 | 7.61E−01 |
| 24 | C3.K1 | 1.10E−09 | 1.47E−08 | 6.99E−01 | 8.91E−01 | 9.38E−01 | 9.70E−01 |
| 25 | C3-OH.K1 | 1.94E−01 | 4.72E−01 | 2.58E−02 | 1.00E−01 | 1.61E−01 | 4.04E−01 |
| 26 | C3:1.K1 | 3.28E−01 | 6.09E−01 | 5.00E−01 | 7.61E−01 | 7.03E−01 | 8.91E−01 |
| 27 | C4.K1 | 1.11E−16 | 1.33E−14 | 3.14E−01 | 6.09E−01 | 2.80E−01 | 5.70E−01 |
| 28 | C4-OH (C3-DC).K1 | 8.26E−01 | 9.35E−01 | 3.27E−01 | 6.09E−01 | 7.50E−01 | 8.91E−01 |
| 29 | C4:1.K1 | 2.35E−02 | 9.42E−02 | 7.41E−01 | 8.91E−01 | 7.48E−01 | 8.91E−01 |
| 30 | C5.K1 | 8.76E−14 | 5.26E−12 | 5.13E−01 | 7.61E−01 | 5.51E−01 | 7.96E−01 |
| 31 | C5-DC (C6-OH).K1 | 6.34E−04 | 3.46E−03 | 6.64E−01 | 8.85E−01 | 1.23E−01 | 3.44E−01 |
| 32 | C5-OH (C3-DC-M).K1 | 1.84E−02 | 7.90E−02 | 1.33E−01 | 3.54E−01 | 7.23E−01 | 8.91E−01 |
| 33 | C5:1.K1 | 7.94E−06 | 5.96E−05 | 7.38E−01 | 8.91E−01 | 2.00E−01 | 4.72E−01 |
| 34 | C5:1-DC.K1 | 1.36E−09 | 1.63E−08 | 8.07E−01 | 9.22E−01 | 5.49E−01 | 7.96E−01 |
| 35 | C6 (C4:1-DC).K1 | 1.07E−06 | 9.15E−06 | 4.47E−01 | 7.20E−01 | 9.80E−01 | 9.88E−01 |
| 36 | C6:1.K1 | 4.60E−02 | 1.61E−01 | 6.20E−01 | 8.75E−01 | 4.26E−01 | 7.20E−01 |
| 37 | C7-DC.K1 | 4.62E−01 | 7.30E−01 | 9.02E−01 | 9.58E−01 | 7.31E−01 | 8.91E−01 |
| 38 | C8.K1 | 1.06E−02 | 4.71E−02 | 3.50E−01 | 6.37E−01 | 8.74E−01 | 9.50E−01 |
| 39 | C8:1.K1 | 4.50E−01 | 7.20E−01 | 1.03E−01 | 3.01E−01 | 9.80E−01 | 9.88E−01 |
| 40 | C9.K1 | 4.35E−03 | 2.17E−02 | 1.47E−01 | 3.83E−01 | 4.01E−02 | 1.50E−01 |
| 41 | H1.K1 | 7.56E−01 | 7.56E−01 | 6.85E−01 | 7.56E−01 | 9.38E−02 | 1.88E−01 |
| 42 | SM (OH) C14:1.K1 | 6.56E−01 | 9.83E−01 | 8.53E−02 | 2.74E−01 | 8.62E−01 | 9.83E−01 |
| 43 | SM (OH) C16:1.K1 | 7.23E−01 | 9.83E−01 | 2.50E−02 | 1.28E−01 | 7.19E−01 | 9.83E−01 |
| 44 | SM (OH) C22:1.K1 | 9.49E−01 | 9.83E−01 | 2.63E−02 | 1.28E−01 | 8.25E−01 | 9.83E−01 |
| 45 | SM (OH) C22:2.K1 | 7.18E−01 | 9.83E−01 | 1.71E−02 | 1.28E−01 | 7.63E−01 | 9.83E−01 |
| 46 | SM (OH) C24:1.K1 | 9.44E−01 | 9.83E−01 | 3.98E−02 | 1.49E−01 | 5.66E−01 | 9.83E−01 |
| 47 | SM C16:0.K1 | 8.55E−01 | 9.83E−01 | 1.13E−02 | 1.27E−01 | 6.25E−01 | 9.83E−01 |
| 48 | SM C16:1.K1 | 9.87E−01 | 9.87E−01 | 2.77E−02 | 1.28E−01 | 9.04E−01 | 9.83E−01 |
| 49 | SM C18:0.K1 | 6.78E−01 | 9.83E−01 | 3.22E−03 | 7.26E−02 | 6.72E−01 | 9.83E−01 |
| 50 | SM C18:1.K1 | 6.68E−01 | 9.83E−01 | 3.23E−03 | 7.26E−02 | 7.82E−01 | 9.83E−01 |
| 51 | SM C20:2.K1 | 2.45E−01 | 7.36E−01 | 5.15E−02 | 1.78E−01 | 7.36E−01 | 9.83E−01 |
| 52 | SM C22:3.K1 | 3.88E−01 | 9.70E−01 | 3.41E−01 | 9.34E−01 | 7.30E−01 | 9.83E−01 |
| 53 | SM C24:0.K1 | 6.33E−01 | 9.83E−01 | 1.05E−02 | 1.27E−01 | 9.61E−01 | 9.83E−01 |
| 54 | SM C24:1.K1 | 9.22E−01 | 9.83E−01 | 3.73E−02 | 1.49E−01 | 8.22E−01 | 9.83E−01 |
| 55 | SM C26:0.K1 | 3.53E−01 | 9.34E−01 | 2.84E−02 | 1.28E−01 | 8.05E−01 | 9.83E−01 |
| 56 | SM C26:1.K1 | 9.05E−01 | 9.83E−01 | 1.97E−02 | 1.28E−01 | 7.54E−01 | 9.83E−01 |
| 57 | PC aa C24:0.K1 | 5.00E−01 | 9.34E−01 | 5.18E−01 | 9.34E−01 | 4.05E−01 | 9.09E−01 |
| 58 | PC aa C26:0.K1 | 5.02E−01 | 9.34E−01 | 9.24E−01 | 9.72E−01 | 3.51E−01 | 8.72E−01 |
| 59 | PC aa C28:1.K1 | 8.74E−01 | 9.72E−01 | 3.64E−02 | 6.32E−01 | 7.57E−01 | 9.72E−01 |
| 60 | PC aa C30:0.K1 | 1.75E−01 | 6.99E−01 | 6.74E−02 | 6.32E−01 | 8.89E−01 | 9.72E−01 |
| 61 | PC aa C30:2.K1 | 9.40E−01 | 9.72E−01 | 9.56E−03 | 6.32E−01 | 7.30E−01 | 9.72E−01 |
| 62 | PC aa C32:0.K1 | 2.77E−01 | 8.25E−01 | 4.08E−01 | 9.09E−01 | 6.77E−01 | 9.72E−01 |
| 63 | PC aa C32:1.K1 | 6.07E−02 | 6.32E−01 | 1.31E−01 | 6.89E−01 | 5.88E−01 | 9.49E−01 |
| 64 | PC aa C32:2.K1 | 9.12E−02 | 6.43E−01 | 6.88E−02 | 6.32E−01 | 5.52E−01 | 9.46E−01 |
| 65 | PC aa C32:3.K1 | 1.10E−01 | 6.43E−01 | 4.36E−02 | 6.32E−01 | 5.15E−01 | 9.34E−01 |
| 66 | PC aa C34:1.K1 | 1.02E−01 | 6.43E−01 | 7.20E−01 | 9.72E−01 | 8.46E−01 | 9.72E−01 |
| 67 | PC aa C34:2.K1 | 1.93E−01 | 7.39E−01 | 7.46E−01 | 9.72E−01 | 8.37E−01 | 9.72E−01 |
| 68 | PC aa C34:3.K1 | 7.32E−02 | 6.32E−01 | 5.99E−01 | 9.51E−01 | 8.79E−01 | 9.72E−01 |

TABLE 4-continued

Duration of hypoxia; p values and q values (i.e., adjusted p values) of regression analyses are given.

| Nr | Analyte | Duration of hypoxia | | Gender effect | | Interaction | |
|---|---|---|---|---|---|---|---|
| | | p value | q value | p value | q value | p value | q value |
| 69 | PC aa C34:4.K1 | 3.80E−02 | 6.32E−01 | 5.39E−01 | 9.46E−01 | 8.16E−01 | 9.72E−01 |
| 70 | PC aa C36:0.K1 | 2.83E−01 | 8.25E−01 | 5.80E−01 | 9.49E−01 | 8.57E−01 | 9.72E−01 |
| 71 | PC aa C36:1.K1 | 3.22E−01 | 8.25E−01 | 5.33E−01 | 9.46E−01 | 8.63E−01 | 9.72E−01 |
| 72 | PC aa C36:2.K1 | 2.94E−01 | 8.25E−01 | 7.88E−01 | 9.72E−01 | 9.20E−01 | 9.72E−01 |
| 73 | PC aa C36:3.K1 | 2.99E−01 | 8.25E−01 | 7.65E−01 | 9.72E−01 | 1.00E+00 | 1.00E+00 |
| 74 | PC aa C36:4.K1 | 1.46E−01 | 6.89E−01 | 4.50E−01 | 9.14E−01 | 9.20E−01 | 9.72E−01 |
| 75 | PC aa C36:5.K1 | 6.47E−02 | 6.32E−01 | 7.99E−01 | 9.72E−01 | 9.66E−01 | 9.87E−01 |
| 76 | PC aa C36:6.K1 | 7.10E−02 | 6.32E−01 | 2.20E−01 | 7.68E−01 | 9.04E−01 | 9.72E−01 |
| 77 | PC aa C38:0.K1 | 9.22E−01 | 9.72E−01 | 4.12E−02 | 6.32E−01 | 7.63E−01 | 9.72E−01 |
| 78 | PC aa C38:1.K1 | 5.56E−01 | 9.48E−01 | 1.03E−01 | 6.43E−01 | 9.94E−01 | 9.98E−01 |
| 79 | PC aa C38:3.K1 | 4.04E−01 | 9.09E−01 | 1.51E−01 | 6.89E−01 | 8.42E−01 | 9.72E−01 |
| 80 | PC aa C38:4.K1 | 1.41E−01 | 6.89E−01 | 2.99E−01 | 8.25E−01 | 8.55E−01 | 9.72E−01 |
| 81 | PC aa C38:5.K1 | 2.68E−01 | 8.25E−01 | 1.57E−01 | 6.89E−01 | 8.19E−01 | 9.72E−01 |
| 82 | PC aa C38:6.K1 | 6.80E−02 | 6.32E−01 | 1.68E−01 | 6.89E−01 | 8.87E−01 | 9.72E−01 |
| 83 | PC aa C40:1.K1 | 8.29E−01 | 9.72E−01 | 6.76E−02 | 6.32E−01 | 2.18E−01 | 7.68E−01 |
| 84 | PC aa C40:2.K1 | 5.45E−01 | 9.46E−01 | 3.17E−01 | 8.25E−01 | 8.81E−01 | 9.72E−01 |
| 85 | PC aa C40:3.K1 | 4.30E−01 | 9.09E−01 | 1.67E−01 | 6.89E−01 | 9.39E−01 | 9.72E−01 |
| 86 | PC aa C40:4.K1 | 9.83E−02 | 6.43E−01 | 9.00E−02 | 6.43E−01 | 7.72E−01 | 9.72E−01 |
| 87 | PC aa C40:5.K1 | 1.24E−01 | 6.84E−01 | 1.55E−01 | 6.89E−01 | 9.08E−01 | 9.72E−01 |
| 88 | PC aa C40:6.K1 | 1.14E−01 | 6.43E−01 | 7.60E−02 | 6.36E−01 | 7.06E−01 | 9.72E−01 |
| 89 | PC aa C42:0.K1 | 8.02E−01 | 9.72E−01 | 2.59E−02 | 6.32E−01 | 4.33E−01 | 9.09E−01 |
| 90 | PC aa C42:1.K1 | 9.22E−01 | 9.72E−01 | 2.17E−01 | 7.68E−01 | 4.92E−01 | 9.34E−01 |
| 91 | PC aa C42:2.K1 | 5.88E−01 | 9.49E−01 | 5.93E−01 | 9.50E−01 | 6.37E−01 | 9.67E−01 |
| 92 | PC aa C42:4.K1 | 7.69E−01 | 9.72E−01 | 3.32E−02 | 6.32E−01 | 9.13E−01 | 9.72E−01 |
| 93 | PC aa C42:5.K1 | 3.40E−01 | 8.53E−01 | 2.93E−02 | 6.32E−01 | 6.68E−01 | 9.72E−01 |
| 94 | PC aa C42:6.K1 | 3.04E−01 | 8.25E−01 | 1.15E−02 | 6.32E−01 | 5.75E−01 | 9.49E−01 |
| 95 | PC ae C30:0.K1 | 6.22E−01 | 9.60E−01 | 4.99E−02 | 6.32E−01 | 9.08E−01 | 9.72E−01 |
| 96 | PC ae C30:1.K1 | 5.44E−01 | 9.46E−01 | 1.09E−01 | 6.43E−01 | 9.71E−01 | 9.89E−01 |
| 97 | PC ae C30:2.K1 | 3.20E−01 | 8.25E−01 | 5.14E−01 | 9.34E−01 | 4.41E−01 | 9.09E−01 |
| 98 | PC ae C32:1.K1 | 2.78E−01 | 8.25E−01 | 8.16E−02 | 6.43E−01 | 7.74E−01 | 9.72E−01 |
| 99 | PC ae C32:2.K1 | 3.08E−01 | 8.25E−01 | 6.41E−02 | 6.32E−01 | 8.00E−01 | 9.72E−01 |
| 100 | PC ae C34:0.K1 | 2.18E−01 | 7.68E−01 | 4.90E−01 | 9.34E−01 | 8.41E−01 | 9.72E−01 |
| 101 | PC ae C34:1.K1 | 2.10E−01 | 7.68E−01 | 1.62E−01 | 6.89E−01 | 7.94E−01 | 9.72E−01 |
| 102 | PC ae C34:2.K1 | 4.93E−01 | 9.34E−01 | 1.64E−01 | 6.89E−01 | 8.12E−01 | 9.72E−01 |
| 103 | PC ae C34:3.K1 | 6.45E−01 | 9.71E−01 | 1.13E−01 | 6.43E−01 | 9.39E−01 | 9.72E−01 |
| 104 | PC ae C36:0.K1 | 6.07E−01 | 9.53E−01 | 2.77E−01 | 8.25E−01 | 8.38E−01 | 9.72E−01 |
| 105 | PC ae C36:1.K1 | 4.45E−01 | 9.10E−01 | 2.66E−01 | 8.25E−01 | 7.32E−01 | 9.72E−01 |
| 106 | PC ae C36:2.K1 | 5.72E−01 | 9.49E−01 | 3.60E−01 | 8.72E−01 | 7.19E−01 | 9.72E−01 |
| 107 | PC ae C36:3.K1 | 5.84E−01 | 9.49E−01 | 1.79E−01 | 7.06E−01 | 9.09E−01 | 9.72E−01 |
| 108 | PC ae C36:4.K1 | 4.41E−01 | 9.09E−01 | 6.99E−02 | 6.32E−01 | 7.69E−01 | 9.72E−01 |
| 109 | PC ae C36:5.K1 | 5.95E−01 | 9.50E−01 | 4.74E−02 | 6.32E−01 | 9.08E−01 | 9.72E−01 |
| 110 | PC ae C38:0.K1 | 4.90E−02 | 6.32E−01 | 1.97E−01 | 7.43E−01 | 6.29E−01 | 9.60E−01 |
| 111 | PC ae C38:1.K1 | 8.91E−01 | 9.72E−01 | 9.21E−02 | 6.43E−01 | 7.85E−01 | 9.72E−01 |
| 112 | PC ae C38:2.K1 | 4.27E−01 | 9.09E−01 | 1.70E−01 | 6.89E−01 | 9.83E−01 | 9.94E−01 |
| 113 | PC ae C38:3.K1 | 5.04E−01 | 9.34E−01 | 8.04E−02 | 6.43E−01 | 7.62E−01 | 9.72E−01 |
| 114 | PC ae C38:4.K1 | 2.40E−01 | 8.16E−01 | 2.99E−01 | 8.25E−01 | 9.90E−01 | 9.97E−01 |
| 115 | PC ae C38:5.K1 | 4.13E−01 | 9.09E−01 | 1.38E−01 | 6.89E−01 | 9.82E−01 | 9.94E−01 |
| 116 | PC ae C38:6.K1 | 6.77E−01 | 9.72E−01 | 1.29E−01 | 6.89E−01 | 8.81E−01 | 9.72E−01 |
| 117 | PC ae C40:0.K1 | 4.12E−02 | 6.32E−01 | 3.70E−01 | 8.74E−01 | 8.74E−01 | 9.72E−01 |
| 118 | PC ae C40:1.K1 | 3.08E−01 | 8.25E−01 | 7.33E−01 | 9.72E−01 | 9.16E−01 | 9.72E−01 |
| 119 | PC ae C40:2.K1 | 7.50E−01 | 9.72E−01 | 5.36E−02 | 6.32E−01 | 6.90E−01 | 9.72E−01 |
| 120 | PC ae C40:3.K1 | 5.43E−01 | 9.46E−01 | 7.38E−01 | 9.72E−01 | 6.76E−01 | 9.72E−01 |
| 121 | PC ae C40:4.K1 | 4.36E−01 | 9.09E−01 | 6.20E−02 | 6.32E−01 | 7.60E−01 | 9.72E−01 |
| 122 | PC ae C40:5.K1 | 3.64E−01 | 8.73E−01 | 1.86E−01 | 7.24E−01 | 8.68E−01 | 9.72E−01 |
| 123 | PC ae C40:6.K1 | 4.39E−01 | 9.09E−01 | 3.18E−02 | 6.32E−01 | 9.15E−01 | 9.72E−01 |
| 124 | PC ae C42:0.K1 | 5.02E−01 | 9.34E−01 | 4.39E−01 | 9.09E−01 | 6.30E−01 | 9.60E−01 |
| 125 | PC ae C42:1.K1 | 5.07E−01 | 9.34E−01 | 5.49E−01 | 9.46E−01 | 6.78E−01 | 9.72E−01 |
| 126 | PC ae C42:2.K1 | 3.23E−01 | 8.25E−01 | 2.96E−01 | 8.25E−01 | 8.31E−01 | 9.72E−01 |
| 127 | PC ae C42:3.K1 | 5.11E−01 | 9.34E−01 | 3.39E−01 | 8.53E−01 | 8.72E−01 | 9.72E−01 |
| 128 | PC ae C42:4.K1 | 7.50E−01 | 9.72E−01 | 8.97E−02 | 6.43E−01 | 5.88E−01 | 9.49E−01 |
| 129 | PC ae C42:5.K1 | 8.73E−01 | 9.72E−01 | 1.38E−01 | 6.89E−01 | 9.05E−01 | 9.72E−01 |
| 130 | PC ae C44:3.K1 | 8.55E−01 | 9.72E−01 | 2.43E−01 | 8.16E−01 | 3.15E−01 | 8.25E−01 |
| 131 | PC ae C44:4.K1 | 4.18E−01 | 9.09E−01 | 3.55E−01 | 8.72E−01 | 5.68E−01 | 9.49E−01 |
| 132 | PC ae C44:5.K1 | 7.46E−01 | 9.72E−01 | 2.55E−01 | 8.25E−01 | 9.29E−01 | 9.72E−01 |
| 133 | PC ae C44:6.K1 | 4.55E−01 | 9.18E−01 | 3.14E−01 | 8.25E−01 | 8.37E−01 | 9.72E−01 |
| 134 | lysoPC a C14:0.K1 | 5.48E−01 | 9.46E−01 | 3.73E−01 | 8.74E−01 | 4.15E−01 | 9.09E−01 |
| 135 | lysoPC a C16:0.K1 | 1.99E−01 | 7.43E−01 | 1.14E−01 | 6.43E−01 | 6.84E−01 | 9.72E−01 |
| 136 | lysoPC a C16:1.K1 | 2.75E−01 | 8.25E−01 | 2.28E−01 | 7.88E−01 | 6.48E−01 | 9.71E−01 |
| 137 | lysoPC a C17:0.K1 | 1.07E−01 | 6.43E−01 | 1.64E−01 | 6.89E−01 | 9.61E−01 | 9.86E−01 |
| 138 | lysoPC a C18:0.K1 | 7.28E−02 | 6.32E−01 | 2.61E−01 | 8.25E−01 | 6.22E−01 | 9.60E−01 |
| 139 | lysoPC a C18:1.K1 | 1.41E−01 | 6.89E−01 | 5.71E−01 | 9.49E−01 | 4.72E−01 | 9.34E−01 |
| 140 | lysoPC a C18:2.K1 | 1.92E−02 | 6.32E−01 | 6.55E−01 | 9.71E−01 | 4.88E−01 | 9.34E−01 |
| 141 | lysoPC a C20:3.K1 | 1.63E−01 | 6.89E−01 | 2.91E−01 | 8.25E−01 | 4.15E−01 | 9.09E−01 |

TABLE 4-continued

Duration of hypoxia; p values and q values (i.e., adjusted p values) of regression analyses are given.

|  |  | Duration of hypoxia | | Gender effect | | Interaction | |
|---|---|---|---|---|---|---|---|
| Nr | Analyte | p value | q value | p value | q value | p value | q value |
| 142 | lysoPC a C20:4.K1 | 2.97E−02 | 6.32E−01 | 4.10E−01 | 9.09E−01 | 6.07E−01 | 9.53E−01 |
| 143 | lysoPC a C24:0.K1 | 6.28E−01 | 9.60E−01 | 5.06E−01 | 9.34E−01 | 3.57E−01 | 8.72E−01 |
| 144 | lysoPC a C26:0.K1 | 8.58E−01 | 9.72E−01 | 4.20E−02 | 6.32E−01 | 3.07E−04 | 8.49E−02 |
| 145 | lysoPC a C26:1.K1 | 8.58E−01 | 9.72E−01 | 3.74E−01 | 8.74E−01 | 2.71E−01 | 8.25E−01 |
| 146 | lysoPC a C28:0.K1 | 9.40E−01 | 9.72E−01 | 6.54E−01 | 9.71E−01 | 7.03E−01 | 9.72E−01 |
| 147 | lysoPC a C28:1.K1 | 1.09E−01 | 6.43E−01 | 1.54E−01 | 6.89E−01 | 3.32E−02 | 6.32E−01 |
| 148 | lysoPC a C6:0.K1 | 9.54E−01 | 9.82E−01 | 2.95E−01 | 8.25E−01 | 5.09E−01 | 9.34E−01 |
| 149 | Gly.K2 | 1.01E−01 | 2.91E−01 | 5.08E−01 | 8.75E−01 | 4.91E−01 | 8.75E−01 |
| 150 | Ala.K2 | 1.73E−09 | 1.30E−07 | 6.32E−01 | 8.79E−01 | 1.56E−01 | 4.05E−01 |
| 151 | Ser.K2 | 7.38E−05 | 1.12E−03 | 8.45E−02 | 2.54E−01 | 5.43E−01 | 8.79E−01 |
| 152 | Pro.K2 | 5.49E−04 | 3.43E−03 | 8.23E−01 | 8.79E−01 | 5.50E−01 | 8.79E−01 |
| 153 | Val.K2 | 3.74E−04 | 3.43E−03 | 8.32E−01 | 8.79E−01 | 8.61E−01 | 8.97E−01 |
| 154 | Thr.K2 | 9.93E−06 | 2.48E−04 | 4.89E−02 | 1.53E−01 | 3.71E−01 | 7.52E−01 |
| 155 | Xle.K2 | 7.48E−05 | 1.12E−03 | 6.99E−01 | 8.79E−01 | 7.22E−01 | 8.79E−01 |
| 156 | Leu.K2 | 4.46E−04 | 3.43E−03 | 8.11E−01 | 8.79E−01 | 5.13E−01 | 8.75E−01 |
| 157 | Ile.K2 | 5.16E−04 | 3.43E−03 | 2.69E−01 | 6.50E−01 | 7.86E−01 | 8.79E−01 |
| 158 | Asn.K2 | 1.02E−04 | 1.27E−03 | 5.68E−01 | 8.79E−01 | 4.61E−01 | 8.75E−01 |
| 159 | Asp.K2 | 2.97E−02 | 1.11E−01 | 7.88E−01 | 8.79E−01 | 4.86E−02 | 1.53E−01 |
| 160 | Gln.K2 | 7.86E−07 | 2.95E−05 | 4.44E−01 | 8.75E−01 | 8.04E−01 | 8.79E−01 |
| 161 | Glu.K2 | 8.31E−04 | 4.79E−03 | 6.28E−01 | 8.79E−01 | 7.27E−01 | 8.79E−01 |
| 162 | Met.K2 | 1.08E−01 | 2.99E−01 | 7.97E−01 | 8.79E−01 | 7.75E−01 | 8.79E−01 |
| 163 | His.K2 | 1.15E−03 | 6.19E−03 | 7.81E−01 | 8.79E−01 | 7.14E−01 | 8.79E−01 |
| 164 | Phe.K2 | 9.99E−03 | 4.16E−02 | 6.48E−01 | 8.79E−01 | 5.99E−01 | 8.79E−01 |
| 165 | Arg.K2 | 4.72E−01 | 8.75E−01 | 9.99E−01 | 9.99E−01 | 6.71E−01 | 8.79E−01 |
| 166 | Cit.K2 | 4.39E−04 | 3.43E−03 | 4.31E−02 | 1.47E−01 | 6.61E−01 | 8.79E−01 |
| 167 | Tyr.K2 | 3.96E−02 | 1.98E−02 | 2.69E−01 | 6.50E−01 | 6.36E−01 | 8.79E−01 |
| 168 | Trp.K2 | 8.19E−03 | 3.61E−02 | 3.25E−01 | 7.18E−01 | 7.28E−01 | 8.79E−01 |
| 169 | Orn.K2 | 2.58E−02 | 1.02E−01 | 7.83E−01 | 8.79E−01 | 9.33E−01 | 9.51E−01 |
| 170 | Lys.K2 | 4.85E−04 | 3.43E−03 | 9.38E−01 | 9.51E−01 | 2.99E−01 | 7.01E−01 |
| 171 | ADMA.K2 | 5.07E−01 | 6.03E−01 | 1.37E−01 | 5.67E−01 | 3.95E−01 | 6.03E−01 |
| 172 | SDMA.K2 | 3.17E−01 | 5.77E−01 | 4.32E−01 | 6.03E−01 | 2.94E−01 | 5.77E−01 |
| 173 | total DMA.K2 | 5.78E−02 | 2.73E−01 | 2.83E−01 | 5.77E−01 | 3.04E−01 | 5.77E−01 |
| 174 | Histamine.K2 | 2.53E−01 | 5.77E−01 | 2.22E−02 | 1.46E−01 | 8.06E−01 | 8.10E−01 |
| 175 | Met-SO.K2 | 3.62E−01 | 7.52E−01 | 3.46E−01 | 7.41E−01 | 1.31E−01 | 3.52E−01 |
| 176 | Kyn.K2 | 4.95E−01 | 6.03E−01 | 7.10E−01 | 7.56E−01 | 2.55E−01 | 5.77E−01 |
| 177 | OH-Kyn.K2 | 1.19E−02 | 9.83E−02 | 1.73E−01 | 5.72E−01 | 2.47E−01 | 5.77E−01 |
| 178 | Putrescine.K2 | 3.21E−12 | 1.06E−10 | 1.58E−01 | 5.72E−01 | 2.04E−01 | 5.77E−01 |
| 179 | Spermidine.K2 | 1.42E−11 | 2.34E−10 | 4.52E−01 | 6.03E−01 | 4.43E−01 | 6.03E−01 |
| 180 | Spermine.K2 | 4.25E−07 | 4.68E−06 | 8.10E−01 | 8.10E−01 | 5.12E−01 | 6.03E−01 |
| 181 | Serotonin.K2 | 5.51E−01 | 6.27E−01 | 2.83E−01 | 1.55E−01 | 5.74E−01 | 6.32E−01 |
| 182 | Creatinine.K2 | 4.92E−01 | 6.03E−01 | 3.45E−01 | 5.77E−01 | 3.50E−01 | 5.77E−01 |
| 183 | Lac.EM | 5.52E−08 | 1.66E−07 | 8.67E−01 | 9.27E−01 | 7.86E−01 | 9.07E−01 |
| 184 | Fum.EM | 4.66E−15 | 3.50E−14 | 1.12E−03 | 2.80E−03 | 3.64E−03 | 7.80E−03 |
| 185 | Asp.EM | 4.83E−03 | 2.27E−02 | 4.25E−02 | 1.47E−01 | 6.82E−01 | 8.79E−01 |
| 186 | Arg.EM | 3.25E−01 | 7.18E−01 | 4.93E−01 | 8.75E−01 | 5.98E−01 | 8.79E−01 |
| 187 | Pyr + OAA.EM | 3.37E−09 | 1.26E−08 | 5.44E−01 | 6.80E−01 | 2.50E−02 | 4.69E−02 |
| 188 | Suc.EM | 0.00E+00 | 0.00E+00 | 5.27E−01 | 6.80E−01 | 4.74E−01 | 6.80E−01 |
| 189 | alpha-KGA.EM | 3.24E−12 | 1.62E−11 | 9.27E−01 | 9.27E−01 | 4.07E−01 | 6.79E−01 |
| 190 | Hex.EM | 5.80E−01 | 7.56E−01 | 1.64E−02 | 9.82E−02 | 8.89E−02 | 1.88E−01 |
| 191 | TCDCA.BA | 8.54E−02 | 3.60E−01 | 3.33E−01 | 7.29E−01 | 7.79E−01 | 8.18E−01 |
| 192 | GCA.BA | 6.18E−04 | 1.30E−02 | 3.46E−01 | 7.29E−01 | 6.70E−02 | 3.60E−01 |
| 193 | CA.BA | 3.94E−03 | 4.13E−02 | 4.57E−01 | 7.29E−01 | 2.71E−01 | 7.29E−01 |
| 194 | UDCA.BA | 4.86E−01 | 7.29E−01 | 6.03E−01 | 8.18E−01 | 4.60E−01 | 7.29E−01 |
| 195 | CDCA.BA | 4.18E−01 | 7.29E−01 | 7.58E−01 | 8.18E−01 | 7.33E−01 | 8.18E−01 |
| 196 | GCDCA.BA | 8.56E−02 | 3.60E−01 | 2.36E−01 | 7.29E−01 | 7.24E−01 | 8.18E−01 |
| 197 | LCA.BA | 7.55E−01 | 8.18E−01 | 9.15E−01 | 9.15E−01 | 4.26E−01 | 7.29E−01 |
| 198 | 13S-HODE.PA | 8.87E−03 | 2.66E−02 | 3.93E−01 | 5.89E−01 | 6.88E−01 | 7.56E−01 |
| 199 | DHA.PA | 4.37E−05 | 3.93E−04 | 3.27E−01 | 5.89E−01 | 6.86E−01 | 7.56E−01 |
| 200 | AA.PA | 3.50E−03 | 1.57E−02 | 2.84E−01 | 5.89E−01 | 7.56E−01 | 7.56E−01 |
| 201 | Orn/Cit | 5.23E−05 | 5.49E−04 | 2.75E−01 | 7.00E−01 | 7.15E−01 | 9.60E−01 |
| 202 | Orn/Arg | 1.12E−01 | 4.29E−01 | 7.96E−01 | 9.60E−01 | 4.99E−01 | 8.50E−01 |
| 203 | Cit/Arg | 9.27E−04 | 7.08E−03 | 1.31E−01 | 4.45E−01 | 8.44E−01 | 9.60E−01 |
| 204 | Glu/Gln | 9.06E−09 | 1.90E−07 | 7.53E−01 | 9.60E−01 | 5.93E−01 | 8.90E−01 |
| 205 | Asp/Asn | 6.21E−06 | 1.04E−04 | 8.31E−01 | 9.60E−01 | 9.16E−02 | 3.85E−01 |
| 206 | Ala/Lys | 2.45E−02 | 1.21E−01 | 8.99E−01 | 9.60E−01 | 9.03E−01 | 9.60E−01 |
| 207 | Phe/Tyr | 7.58E−01 | 9.60E−01 | 3.46E−02 | 1.61E−01 | 1.53E−01 | 4.60E−01 |
| 208 | Serotonin/Trp | 9.58E−01 | 9.81E−01 | 2.13E−02 | 1.12E−01 | 5.52E−01 | 8.75E−01 |
| 209 | Kyn/Trp | 1.01E−02 | 6.52E−02 | 3.57E−01 | 7.37E−01 | 5.06E−01 | 8.75E−01 |
| 210 | Kyn/OHKyn | 3.96E−05 | 4.75E−04 | 1.50E−01 | 4.60E−01 | 3.19E−01 | 7.06E−01 |
| 211 | Putrescine/Orn | 7.74E−09 | 1.90E−07 | 5.42E−01 | 8.75E−01 | 2.90E−01 | 7.06E−01 |
| 212 | Spermine/Spermidine | 3.14E−10 | 1.32E−08 | 8.99E−01 | 9.60E−01 | 6.67E−01 | 9.33E−01 |
| 213 | SDMA/ADMA | 3.77E−01 | 7.37E−01 | 9.18E−01 | 9.64E−01 | 4.17E−01 | 7.62E−01 |
| 214 | Met-SO/Met | 1.36E−03 | 9.55E−03 | 1.15E−04 | 1.07E−03 | 1.58E−02 | 9.49E−02 |

TABLE 4-continued

Duration of hypoxia; p values and q values (i.e., adjusted
p values) of regression analyses are given.

| | | Duration of hypoxia | | Gender effect | | Interaction | |
|---|---|---|---|---|---|---|---|
| Nr | Analyte | p value | q value | p value | q value | p value | q value |
| 215 | Ala/BCAA | 2.93E−05 | 4.10E−04 | 5.85E−01 | 8.90E−01 | 2.98E−01 | 7.06E−01 |
| 216 | Gly/BCAA | 2.29E−04 | 1.93E−03 | 8.01E−01 | 9.60E−01 | 9.92E−01 | 9.92E−01 |
| 217 | SumLyso | 1.92E−01 | 5.04E−01 | 6.93E−01 | 9.54E−01 | 6.10E−01 | 8.98E−01 |
| 218 | SumPC + Lyso | 3.15E−01 | 7.06E−01 | 1.72E−01 | 4.91E−01 | 8.92E−01 | 9.60E−01 |
| 219 | SumPC | 3.67E−01 | 7.37E−01 | 1.32E−01 | 4.45E−01 | 8.07E−01 | 9.60E−01 |
| 220 | SumSM | 9.87E−01 | 9.92E−01 | 1.79E−02 | 1.00E−01 | 8.99E−01 | 9.60E−01 |
| 221 | SumSMOH/SumSM | 6.55E−01 | 9.33E−01 | 5.63E−01 | 8.76E−01 | 6.43E−01 | 9.31E−01 |
| 222 | C16 + C18/C0 | 3.66E−13 | 3.07E−11 | 7.48E−01 | 9.60E−01 | 3.76E−01 | 7.37E−01 |
| 223 | SumMUFA | 4.11E−01 | 7.62E−01 | 8.22E−02 | 3.64E−01 | 8.15E−01 | 9.60E−01 |
| 224 | SumPUFA | 3.54E−01 | 7.37E−01 | 1.18E−01 | 4.31E−01 | 8.53E−01 | 9.60E−01 |
| 225 | SumSFA | 4.72E−01 | 8.44E−01 | 1.81E−01 | 4.91E−01 | 9.31E−01 | 9.65E−01 |
| 226 | PUFA/SFA | 3.11E−01 | 7.06E−01 | 1.48E−01 | 4.60E−01 | 5.48E−01 | 8.75E−01 |
| 227 | PUFA/MUFA | 1.81E−01 | 4.91E−01 | 8.41E−01 | 9.60E−01 | 8.47E−01 | 9.60E−01 |
| 228 | MUFA/SFA | 4.84E−01 | 8.46E−01 | 9.72E−02 | 3.89E−01 | 4.08E−01 | 7.62E−01 |
| 229 | 24SOHC | 7.72E−03 | 3.01E−01 | 2.70E−01 | 7.32E−01 | 7.79E−01 | 9.40E−01 |
| 230 | 25OHC | 1.96E−01 | 7.32E−01 | 2.83E−01 | 7.32E−01 | 8.43E−01 | 9.40E−01 |
| 231 | 27OHC | 9.35E−02 | 6.60E−01 | 7.55E−01 | 9.40E−01 | 3.05E−01 | 7.32E−01 |
| 232 | 24,25,EPC | 8.07E−01 | 9.40E−01 | 9.78E−01 | 9.78E−01 | 8.80E−01 | 9.53E−01 |
| 233 | 7aOHC | 5.26E−01 | 8.20E−01 | 7.71E−01 | 9.40E−01 | 5.20E−01 | 8.20E−01 |
| 234 | 5B,6B,EPC | 3.79E−02 | 6.37E−01 | 8.27E−01 | 9.40E−01 | 7.84E−01 | 9.40E−01 |
| 235 | 5a,6a,EPC | 4.90E−02 | 6.37E−01 | 2.42E−01 | 7.32E−01 | 3.64E−01 | 7.48E−01 |
| 236 | 4BOHC | 2.53E−01 | 7.32E−01 | 4.84E−01 | 8.20E−01 | 2.78E−01 | 7.32E−01 |
| 237 | Desmosterol | 4.51E−01 | 8.20E−01 | 3.37E−01 | 7.32E−01 | 3.27E−01 | 7.32E−01 |
| 238 | 7DHC | 9.67E−01 | 9.78E−01 | 8.06E−01 | 9.40E−01 | 9.85E−02 | 6.60E−01 |
| 239 | Cholestenone | 1.50E−01 | 7.32E−01 | 1.61E−01 | 7.32E−01 | 9.32E−01 | 9.78E−01 |
| 240 | Lanosterol | 3.38E−01 | 7.32E−01 | 4.61E−01 | 8.20E−01 | 1.02E−01 | 6.60E−01 |
| 241 | 24DHLan | 8.05E−01 | 9.40E−01 | 5.02E−01 | 8.20E−01 | 7.60E−01 | 9.40E−01 |

TABLE 5

Effectiveness of reoxygenation; p values obtained by post hoc analyses via
Tukey's honest significant difference and fold changes (FC) are depicted.

| | | Group2 vs Group 1 | | Group3 vs Group1 | | Group3 vs Group2 | |
|---|---|---|---|---|---|---|---|
| Nr | Analyte | p value | FC | p value | FC | p value | FC |
| 1 | C0.K1 | 5.97E−01 | 3.69 | 9.45E−01 | 2.03 | 5.85E−01 | −1.63 |
| 2 | C10.K1 | 3.58E−02 | −13.23 | 1.96E−01 | −19.82 | 3.23E−01 | −5.82 |
| 3 | C10:1.K1 | 9.82E−02 | −16.54 | 1.18E−01 | −9.49 | 8.95E−01 | 6.43 |
| 4 | C10:2.K1 | 7.47E−02 | −10.34 | 5.50E−05 | −35.89 | 1.43E−02 | −23.15 |
| 5 | C12.K1 | 1.81E−01 | −18.26 | 2.14E−01 | −11.95 | 7.38E−01 | 5.63 |
| 6 | C12-DC.K1 | 1.24E−02 | −11.02 | 3.70E−01 | −1.67 | 4.45E−02 | 9.20 |
| 7 | C12:1.K1 | 1.91E−01 | −32.41 | 4.66E−01 | −29.57 | 3.94E−01 | 2.19 |
| 8 | C14.K1 | 2.54E−01 | −10.73 | 5.20E−01 | −11.26 | 4.05E−01 | −0.48 |
| 9 | C14:1.K1 | 1.20E−01 | −18.98 | 3.27E−01 | −16.79 | 3.83E−01 | 1.87 |
| 10 | C14:1-OH.K1 | 3.14E−01 | −21.43 | 5.58E−01 | −19.58 | 7.40E−01 | 1.55 |
| 11 | C14:2.K1 | 8.47E−01 | −9.02 | 9.64E−01 | −11.17 | 7.50E−01 | −1.97 |
| 12 | C14:2-OH.K1 | 2.17E−01 | −18.97 | 5.81E−02 | −31.91 | 4.79E−01 | −10.88 |
| 13 | C16.K1 | 3.48E−02 | −20.63 | 3.31E−01 | −16.32 | 2.11E−01 | 3.71 |
| 14 | C16-OH.K1 | 4.31E−03 | −27.27 | 9.38E−01 | 5.63 | 2.55E−02 | 34.44 |
| 15 | C16:1.K1 | 8.39E−02 | −48.01 | 6.82E−01 | 3.49 | 1.11E−01 | 53.17 |
| 16 | C16:1-OH.K1 | 1.17E−03 | −33.94 | 4.52E−01 | −26.51 | 4.32E−01 | 5.87 |
| 17 | C16:2.K1 | 3.22E−01 | −22.45 | 1.96E−01 | −13.72 | 9.02E−01 | 7.67 |
| 18 | C16:2-OH.K1 | 3.22E−01 | −12.50 | 7.80E−01 | 10.25 | 1.32E−01 | 24.03 |
| 19 | C18.K1 | 7.08E−02 | −8.90 | 5.61E−01 | −3.52 | 3.74E−01 | 5.20 |
| 20 | C18:1.K1 | 1.09E−01 | −15.69 | 4.42E−01 | −1.86 | 3.05E−01 | 13.58 |
| 21 | C18:1-OH.K1 | 4.31E−01 | −3.13 | 4.07E−01 | 0.56 | 8.16E−02 | 3.70 |
| 22 | C18:2.K1 | 2.64E−02 | −68.58 | 5.23E−01 | 4.02 | 3.39E−02 | 75.36 |
| 23 | C2.K1 | 6.70E−02 | −20.30 | 8.78E−01 | −0.81 | 7.91E−02 | 19.33 |
| 24 | C3.K1 | 6.77E−05 | −57.28 | 8.73E−01 | −18.34 | 9.21E−02 | 32.91 |
| 25 | C3-OH.K1 | 1.89E−01 | 18.68 | 7.75E−01 | 1.64 | 8.43E−02 | −16.77 |
| 26 | C3:1.K1 | 1.28E−02 | −33.33 | 9.42E−03 | −44.29 | 7.85E−01 | −8.22 |
| 27 | C4.K1 | 1.63E−03 | −38.40 | 2.62E−01 | −10.63 | 7.16E−02 | 25.10 |
| 28 | C4-OH (C3-DC).K1 | 4.55E−02 | −26.53 | 3.98E−01 | −5.44 | 1.81E−01 | 20.00 |
| 29 | C4:1.K1 | 3.09E−02 | −37.28 | 2.28E−02 | −38.70 | 6.70E−01 | −1.03 |
| 30 | C5.K1 | 9.51E−03 | −25.60 | 8.32E−01 | 5.69 | 2.60E−02 | 32.74 |
| 31 | C5-DC (C6-OH).K1 | 3.29E−01 | −12.50 | 7.62E−01 | −5.05 | 3.15E−01 | 7.09 |
| 32 | C5-OH (C3-DC-M).K1 | 5.76E−01 | −2.88 | 5.30E−01 | 1.60 | 1.93E−01 | 4.52 |
| 33 | C5:1.K1 | 5.30E−02 | −5.00 | 5.80E−02 | −10.46 | 9.23E−01 | −5.20 |

TABLE 5-continued

Effectiveness of reoxygenation; p values obtained by post hoc analyses via Tukey's honest significant difference and fold changes (FC) are depicted.

| Nr | Analyte | Group2 vs Group 1 | | Group3 vs Group1 | | Group3 vs Group2 | |
|---|---|---|---|---|---|---|---|
| | | p value | FC | p value | FC | p value | FC |
| 34 | C5:1-DC.K1 | 2.07E−01 | −14.29 | 4.84E−01 | −1.19 | 5.45E−01 | 12.94 |
| 35 | C6(C4:1-DC).K1 | 2.58E−02 | −5.33 | 1.62E−01 | −8.29 | 7.87E−01 | −2.81 |
| 36 | C6:1.K1 | 5.45E−01 | −18.13 | 4.85E−01 | −13.19 | 8.69E−01 | 4.36 |
| 37 | C7-DC.K1 | 2.97E−01 | −25.06 | 5.93E−01 | −13.33 | 6.46E−01 | 10.34 |
| 38 | C8.K1 | 3.14E−01 | −4.50 | 4.07E−02 | −8.43 | 6.04E−01 | −3.76 |
| 39 | C8:1.K1 | 6.09E−01 | 6.20 | 6.47E−01 | −2.41 | 9.26E−01 | −8.77 |
| 40 | C9.K1 | 5.34E−01 | −3.24 | 1.46E−01 | −33.99 | 5.25E−02 | −29.79 |
| 41 | H1.K1 | 5.96E−02 | −30.86 | 1.21E−01 | −28.48 | 3.60E−01 | 1.85 |
| 42 | SM (OH) C14:1.K1 | 2.18E−01 | −13.25 | 7.03E−01 | −5.82 | 5.75E−01 | 7.02 |
| 43 | SM (OH) C16:1.K1 | 8.88E−01 | 3.79 | 5.24E−01 | 0.19 | 5.16E−01 | −3.60 |
| 44 | SM (OH) C22:1.K1 | 3.64E−01 | −9.63 | 2.79E−01 | −10.07 | 6.60E−01 | −0.40 |
| 45 | SM (OH) C22:2.K1 | 1.76E−01 | −12.55 | 7.68E−01 | −4.62 | 2.98E−01 | 7.58 |
| 46 | SM (OH) C24:1.K1 | 6.53E−03 | −9.97 | 3.14E−01 | −1.87 | 2.65E−01 | 7.95 |
| 47 | SM C16:0.K1 | 8.51E−01 | −1.91 | 6.16E−01 | 2.84 | 5.47E−01 | 4.81 |
| 48 | SM C16:1.K1 | 1.50E−01 | −12.17 | 5.36E−01 | 0.11 | 5.99E−01 | 12.30 |
| 49 | SM C18:0.K1 | 3.23E−01 | −12.17 | 5.96E−01 | −3.10 | 8.79E−01 | −3.10 |
| 50 | SM C18:1.K1 | 1.29E−01 | −8.62 | 5.47E−01 | −3.60 | 6.56E−01 | 4.85 |
| 51 | SM C20:2.K1 | 8.29E−01 | 3.95 | 7.57E−01 | 2.84 | 6.69E−01 | −1.08 |
| 52 | SM C22:3.K1 | 2.12E−01 | −5.77 | 1.84E−02 | −18.67 | 4.13E−01 | −12.19 |
| 53 | SM C24:0.K1 | 3.40E−02 | −15.31 | 2.54E−01 | −6.48 | 6.26E−01 | 8.29 |
| 54 | SM C24:1.K1 | 6.55E−02 | −9.89 | 9.01E−02 | −6.74 | 6.96E−01 | 2.95 |
| 55 | SM C26:0.K1 | 4.60E−01 | −8.98 | 4.30E−01 | −6.01 | 9.94E−01 | 2.80 |
| 56 | SM C26:1.K1 | 2.34E−01 | −14.78 | 2.05E−01 | −5.84 | 8.88E−01 | 8.45 |
| 57 | PC aa C24:0.K1 | 3.84E−01 | −15.71 | 2.09E−02 | −28.59 | 1.72E−01 | −11.13 |
| 58 | PC aa C26:0.K1 | 4.06E−01 | −6.93 | 3.39E−01 | −5.17 | 9.52E−01 | 1.67 |
| 59 | PC aa C28:1.K1 | 3.20E−01 | −5.36 | 4.89E−01 | −0.11 | 7.47E−01 | 5.24 |
| 60 | PC aa C30:0.K1 | 6.67E−01 | 4.73 | 9.89E−01 | 0.62 | 6.31E−01 | −4.09 |
| 61 | PC aa C30:2.K1 | 7.55E−02 | −13.43 | 6.59E−01 | −6.99 | 3.59E−01 | 6.03 |
| 62 | PC aa C32:0.K1 | 7.76E−01 | 10.58 | 9.73E−01 | 1.26 | 8.07E−01 | −9.20 |
| 63 | PC aa C32:1.K1 | 7.13E−01 | 2.50 | 5.42E−01 | −2.05 | 4.48E−01 | −4.60 |
| 64 | PC aa C32:2.K1 | 9.51E−01 | −0.42 | 3.79E−01 | −11.20 | 3.99E−01 | −10.73 |
| 65 | PC aa C32:3.K1 | 6.84E−01 | 4.65 | 4.71E−01 | 1.70 | 8.49E−01 | −2.90 |
| 66 | PC aa C34:1.K1 | 8.05E−01 | 8.71 | 8.50E−01 | 1.26 | 7.13E−01 | −7.36 |
| 67 | PC aa C34:2.K1 | 8.35E−01 | 3.84 | 4.01E−01 | −4.76 | 7.14E−01 | −8.78 |
| 68 | PC aa C34:3.K1 | 9.70E−01 | 10.93 | 5.05E−01 | −6.99 | 5.55E−01 | −18.69 |
| 69 | PC aa C34:4.K1 | 5.73E−01 | 8.62 | 5.77E−01 | 0.29 | 3.23E−01 | −8.30 |
| 70 | PC aa C36:0.K1 | 6.59E−01 | 2.93 | 2.08E−01 | −6.14 | 4.59E−01 | −9.25 |
| 71 | PC aa C36:1.K1 | 7.98E−01 | 5.27 | 3.39E−01 | −2.95 | 5.72E−01 | −8.37 |
| 72 | PC aa C36:2.K1 | 7.19E−01 | 0.95 | 5.12E−01 | −6.01 | 8.70E−01 | −7.02 |
| 73 | PC aa C36:3.K1 | 6.90E−01 | −0.33 | 1.29E−01 | −14.05 | 4.89E−01 | −13.67 |
| 74 | PC aa C36:4.K1 | 7.58E−01 | 1.58 | 6.37E−02 | −9.08 | 4.14E−01 | −10.81 |
| 75 | PC aa C36:5.K1 | 9.29E−01 | 8.56 | 1.09E−01 | −8.28 | 2.10E−01 | −17.55 |
| 76 | PC aa C36:6.K1 | 7.29E−01 | 1.20 | 3.95E−01 | −5.64 | 6.73E−01 | −6.91 |
| 77 | PC aa C38:0.K1 | 6.14E−01 | −1.84 | 1.56E−01 | −6.71 | 3.98E−01 | −4.78 |
| 78 | PC aa C38:1.K1 | 9.51E−01 | −4.41 | 9.08E−01 | −2.59 | 9.32E−01 | 1.77 |
| 79 | PC aa C38:3.K1 | 3.39E−01 | −0.24 | 2.32E−01 | −6.52 | 8.60E−01 | −6.27 |
| 80 | PC aa C38:4.K1 | 8.37E−01 | 2.06 | 2.72E−01 | −2.55 | 4.58E−01 | −4.67 |
| 81 | PC aa C38:5.K1 | 6.82E−01 | −2.13 | 2.39E−01 | −9.70 | 4.91E−01 | −7.41 |
| 82 | PC aa C38:6.K1 | 8.58E−01 | −0.51 | 3.32E−01 | −5.70 | 6.30E−01 | −5.16 |
| 83 | PC aa C40:1.K1 | 4.36E−01 | 7.80 | 5.34E−01 | −2.02 | 2.39E−01 | −9.98 |
| 84 | PC aa C40:2.K1 | 3.07E−01 | 0.24 | 5.16E−01 | −5.48 | 8.16E−01 | −5.72 |
| 85 | PC aa C40:3.K1 | 1.83E−01 | −3.37 | 1.53E−01 | −8.86 | 7.13E−01 | −5.31 |
| 86 | PC aa C40:4.K1 | 9.88E−01 | 0.16 | 6.91E−01 | −4.25 | 7.68E−01 | −4.42 |
| 87 | PC aa C40:5.K1 | 6.79E−01 | 4.03 | 7.96E−01 | 0.35 | 6.05E−01 | −3.67 |
| 88 | PC aa C40:6.K1 | 8.44E−01 | 6.89 | 4.16E−01 | −3.43 | 4.62E−01 | −10.56 |
| 89 | PC aa C42:0.K1 | 3.49E−01 | −9.67 | 3.85E−01 | −11.90 | 8.93E−01 | −2.03 |
| 90 | PC aa C42:1.K1 | 2.53E−01 | −3.22 | 1.40E−01 | −8.46 | 5.85E−01 | −5.08 |
| 91 | PC aa C42:2.K1 | 1.75E−01 | −0.92 | 1.32E−02 | −16.95 | 3.15E−01 | −15.88 |
| 92 | PC aa C42:4.K1 | 7.62E−01 | −2.84 | 6.98E−01 | −4.76 | 9.00E−01 | −1.87 |
| 93 | PC aa C42:5.K1 | 8.23E−01 | −4.68 | 1.46E−01 | −3.06 | 3.65E−01 | 1.57 |
| 94 | PC aa C42:6.K1 | 4.21E−01 | 5.75 | 9.48E−01 | 3.27 | 4.35E−01 | −2.41 |
| 95 | PC ae C30:0.K1 | 1.23E−02 | −17.00 | 4.61E−03 | −12.79 | 7.98E−01 | 3.74 |
| 96 | PC ae C30:1.K1 | 6.85E−01 | −2.72 | 5.23E−01 | −7.48 | 7.25E−01 | −4.63 |
| 97 | PC ae C30:2.K1 | 4.65E−02 | −10.18 | 1.27E−01 | −5.99 | 6.50E−01 | 3.94 |
| 98 | PC ae C32:1.K1 | 9.51E−01 | 2.66 | 5.70E−01 | 1.04 | 6.99E−01 | −1.60 |
| 99 | PC ae C32:2.K1 | 6.40E−01 | −1.76 | 4.07E−01 | −1.33 | 2.91E−01 | 0.42 |
| 100 | PC ae C34:0.K1 | 9.93E−01 | 7.76 | 1.03E−01 | −5.20 | 2.84E−01 | −13.36 |
| 101 | PC ae C34:1.K1 | 5.29E−01 | −9.08 | 4.01E−01 | −4.86 | 7.81E−01 | 4.02 |
| 102 | PC ae C34:2.K1 | 7.25E−01 | 0.26 | 6.04E−01 | 1.51 | 8.50E−01 | 1.24 |
| 103 | PC ae C34:3.K1 | 3.24E−01 | −5.08 | 2.80E−01 | −0.89 | 9.11E−01 | 4.15 |
| 104 | PC ae C36:0.K1 | 8.66E−01 | 0.37 | 6.26E−01 | −3.43 | 8.01E−01 | −3.81 |
| 105 | PC ae C36:1.K1 | 7.81E−01 | 3.56 | 6.38E−01 | −1.89 | 8.46E−01 | −5.52 |
| 106 | PC ae C36:2.K1 | 5.68E−01 | −6.67 | 2.28E−01 | −8.67 | 6.77E−01 | −1.87 |

TABLE 5-continued

Effectiveness of reoxygenation; p values obtained by post hoc analyses via Tukey's honest significant difference and fold changes (FC) are depicted.

| | | Group2 vs Group 1 | | Group3 vs Group1 | | Group3 vs Group2 | |
|---|---|---|---|---|---|---|---|
| Nr | Analyte | p value | FC | p value | FC | p value | FC |
| 107 | PC ae C36:3.K1 | 4.77E−01 | −6.30 | 1.23E−01 | −5.15 | 4.69E−01 | 1.09 |
| 108 | PC ae C36:4.K1 | 2.76E−01 | −2.68 | 1.55E−01 | −6.92 | 6.44E−01 | −4.13 |
| 109 | PC ae C36:5.K1 | 5.90E−01 | −3.89 | 6.26E−01 | −2.83 | 9.64E−01 | 1.02 |
| 110 | PC ae C38:0.K1 | 5.91E−01 | 0.79 | 2.15E−01 | −9.00 | 5.21E−01 | −9.86 |
| 111 | PC ae C38:1.K1 | 3.09E−01 | −1.76 | 2.20E−01 | −11.73 | 7.06E−01 | −9.79 |
| 112 | PC ae C38:2.K1 | 9.16E−01 | 1.65 | 4.51E−01 | −3.24 | 5.84E−01 | −4.95 |
| 113 | PC ae C38:3.K1 | 5.73E−01 | −2.21 | 6.05E−01 | −4.80 | 9.90E−01 | −2.54 |
| 114 | PC ae C38:4.K1 | 6.87E−01 | 1.95 | 4.54E−02 | −5.50 | 2.09E−01 | −7.56 |
| 115 | PC ae C38:5.K1 | 4.93E−01 | 2.56 | 7.84E−02 | −6.69 | 3.15E−01 | −9.42 |
| 116 | PC ae C38:6.K1 | 5.96E−01 | −0.81 | 1.05E−01 | −5.68 | 3.48E−01 | −4.83 |
| 117 | PC ae C40:0.K1 | 2.93E−01 | 1.69 | 4.40E−01 | −1.82 | 1.20E−01 | −3.55 |
| 118 | PC ae C40:1.K1 | 2.17E−01 | −8.35 | 3.00E−02 | −14.06 | 4.49E−01 | −5.27 |
| 119 | PC ae C40:2.K1 | 8.52E−01 | −1.50 | 3.82E−01 | −10.33 | 4.28E−01 | −8.70 |
| 120 | PC ae C40:3.K1 | 1.44E−01 | −6.44 | 2.98E−02 | −16.15 | 2.69E−01 | −9.13 |
| 121 | PC ae C40:4.K1 | 8.50E−01 | −0.05 | 9.89E−02 | −5.93 | 3.18E−01 | −5.87 |
| 122 | PC ae C40:5.K1 | 7.99E−01 | −1.71 | 3.46E−01 | −3.68 | 4.75E−01 | −1.94 |
| 123 | PC ae C40:6.K1 | 4.63E−01 | 3.96 | 8.68E−01 | 3.15 | 6.50E−01 | −0.79 |
| 124 | PC ae C42:0.K1 | 6.04E−01 | −1.91 | 7.65E−01 | −0.59 | 7.57E−01 | 1.31 |
| 125 | PC ae C42:1.K1 | 3.43E−01 | −4.77 | 4.93E−02 | −12.84 | 5.00E−01 | −7.70 |
| 126 | PC ae C42:2.K1 | 4.85E−01 | 9.84 | 2.72E−01 | −1.05 | 9.16E−01 | −10.99 |
| 127 | PC ae C42:3.K1 | 1.73E−01 | −2.97 | 5.52E−01 | −2.03 | 5.10E−01 | 0.92 |
| 128 | PC ae C42:4.K1 | 3.21E−01 | −5.97 | 9.07E−01 | 1.50 | 5.38E−01 | 7.56 |
| 129 | PC ae C42:5.K1 | 2.03E−02 | −8.84 | 2.94E−02 | −11.09 | 8.12E−01 | −2.06 |
| 130 | PC ae C44:3.K1 | 1.95E−01 | −16.11 | 2.31E−01 | −11.48 | 8.62E−01 | 4.16 |
| 131 | PC ae C44:4.K1 | 8.93E−01 | −4.44 | 6.69E−02 | −13.79 | 1.11E−01 | −8.95 |
| 132 | PC ae C44:5.K1 | 8.50E−01 | −0.72 | 2.71E−01 | −8.89 | 2.91E−01 | −8.12 |
| 133 | PC ae C44:6.K1 | 3.94E−01 | 0.56 | 1.48E−02 | −19.11 | 1.60E−01 | −19.78 |
| 134 | lysoPC a C14:0.K1 | 1.52E−01 | 0.82 | 1.39E−01 | −1.03 | 9.17E−01 | −1.85 |
| 135 | lysoPC a C16:0.K1 | 1.79E−01 | −8.36 | 1.38E−01 | −17.69 | 6.94E−01 | −8.61 |
| 136 | lysoPC a C16:1.K1 | 4.57E−01 | −2.29 | 1.56E−01 | −17.42 | 4.47E−01 | −14.79 |
| 137 | lysoPC a C17:0.K1 | 7.21E−01 | −4.83 | 3.73E−01 | −32.79 | 5.33E−01 | −26.68 |
| 138 | lysoPC a C18:0.K1 | 5.14E−02 | −13.17 | 2.85E−02 | −26.65 | 6.09E−01 | −11.91 |
| 139 | lysoPC a C18:1.K1 | 4.43E−01 | −10.48 | 1.47E−01 | −13.27 | 4.60E−01 | −2.53 |
| 140 | lysoPC a C18:2.K1 | 5.70E−01 | −1.41 | 2.85E−01 | −8.20 | 7.45E−01 | −6.70 |
| 141 | lysoPC a C20:3.K1 | 3.12E−01 | −21.77 | 3.79E−01 | −9.00 | 8.15E−01 | 11.72 |
| 142 | lysoPC a C20:4.K1 | 5.08E−01 | −25.92 | 2.16E−01 | −24.53 | 5.87E−01 | 1.12 |
| 143 | lysoPC a C24:0.K1 | 9.82E−02 | −6.30 | 2.99E−02 | −18.39 | 9.75E−01 | −11.37 |
| 144 | lysoPC a C26:0.K1 | 1.87E−01 | −8.04 | 5.80E−01 | −6.59 | 2.44E−01 | 1.36 |
| 145 | lysoPC a C26:1.K1 | 8.21E−01 | 1.12 | 3.68E−01 | −2.90 | 5.49E−01 | −4.05 |
| 146 | lysoPC a C28:0.K1 | 1.34E−01 | −9.33 | 7.46E−01 | −5.50 | 3.10E−01 | 3.63 |
| 147 | lysoPC a C28:1.K1 | 8.53E−02 | −12.56 | 7.90E−01 | 5.34 | 1.31E−01 | 18.57 |
| 148 | lysoPC a C6:0.K1 | 8.36E−02 | −59.18 | 4.60E−02 | −173.79 | 5.89E−01 | −72.00 |
| 149 | Gly.K2 | 6.91E−01 | −3.90 | 3.46E−01 | −19.98 | 6.46E−01 | −15.48 |
| 150 | Ala.K2 | 6.84E−01 | −5.15 | 8.34E−01 | 3.21 | 7.75E−01 | 8.52 |
| 151 | Ser.K2 | 6.55E−01 | −13.56 | 1.28E−01 | −25.39 | 2.88E−01 | −10.42 |
| 152 | Pro.K2 | 1.52E−01 | −3.22 | 3.82E−01 | −4.89 | 4.49E−01 | −1.62 |
| 153 | Val.K2 | 1.95E−01 | −3.82 | 4.52E−01 | −4.01 | 4.53E−01 | −0.19 |
| 154 | Thr.K2 | 3.40E−01 | −9.40 | 4.40E−01 | −10.53 | 8.99E−01 | −1.03 |
| 155 | Xle.K2 | 1.60E−01 | −5.31 | 4.77E−01 | −19.90 | 4.91E−01 | −13.86 |
| 156 | Leu.K2 | 2.12E−01 | −15.34 | 4.12E−01 | −26.01 | 6.35E−01 | −9.25 |
| 157 | Ile.K2 | 1.41E−01 | −10.99 | 2.92E−01 | −19.53 | 6.99E−01 | −7.69 |
| 158 | Asn.K2 | 2.18E−01 | 2.98 | 4.24E−01 | −7.78 | 5.77E−01 | −10.99 |
| 159 | Asp.K2 | 6.89E−02 | −70.92 | 9.15E−01 | −26.93 | 7.11E−02 | 34.66 |
| 160 | Gln.K2 | 8.28E−01 | −5.18 | 9.06E−01 | −4.29 | 8.99E−01 | 0.86 |
| 161 | Glu.K2 | 1.70E−01 | −16.38 | 2.99E−01 | −19.80 | 5.71E−01 | −2.94 |
| 162 | Met.K2 | 2.42E−02 | −46.09 | 3.18E−02 | −59.04 | 7.54E−01 | −8.86 |
| 163 | His.K2 | 9.82E−01 | 3.35 | 7.02E−01 | −9.02 | 7.23E−01 | −12.67 |
| 164 | Phe.K2 | 1.64E−01 | −8.75 | 4.82E−01 | −6.79 | 3.20E−01 | 1.83 |
| 165 | Arg.K2 | 3.61E−01 | −9.48 | 3.27E−01 | −18.87 | 9.80E−01 | −8.57 |
| 166 | Cit.K2 | 1.44E−01 | −12.89 | 1.73E−01 | −18.41 | 9.39E−01 | −4.89 |
| 167 | Tyr.K2 | 1.98E−01 | −8.33 | 2.31E−01 | −6.08 | 8.79E−01 | 2.12 |
| 168 | Trp.K2 | 6.26E−01 | −4.96 | 9.67E−01 | −1.61 | 6.64E−01 | 3.30 |
| 169 | Orn.K2 | 6.17E−01 | 2.27 | 1.61E−01 | −18.38 | 1.11E−01 | −21.07 |
| 170 | Lys.K2 | 3.21E−01 | −12.76 | 8.22E−01 | 9.28 | 2.57E−01 | 23.23 |
| 171 | ADMA.K2 | 4.97E−02 | −26.79 | 1.48E−01 | −17.95 | 4.23E−01 | 7.49 |
| 172 | SDMA.K2 | 2.45E−01 | −5.59 | 3.35E−01 | −15.63 | 6.03E−01 | −9.51 |
| 173 | total DMA.K2 | 2.31E−01 | −33.17 | 2.31E−01 | −17.06 | 7.57E−01 | 13.77 |
| 174 | Histamine.K2 | 3.53E−01 | −35.36 | 2.38E−01 | −27.19 | 9.89E−01 | 6.42 |
| 175 | Met-SO.K2 | 2.36E−01 | −41.82 | 6.31E−01 | −18.47 | 4.92E−01 | 19.71 |
| 176 | Kyn.K2 | 7.91E−01 | 3.17 | 8.30E−01 | 1.58 | 6.78E−01 | −1.57 |
| 177 | OH-Kyn.K2 | 1.53E−01 | −11.26 | 3.29E−01 | −16.21 | 7.25E−01 | −4.45 |

TABLE 5-continued

Effectiveness of reoxygenation; p values obtained by post hoc analyses via Tukey's honest significant difference and fold changes (FC) are depicted.

| Nr | Analyte | Group2 vs Group 1 | | Group3 vs Group1 | | Group3 vs Group2 | |
|---|---|---|---|---|---|---|---|
| | | p value | FC | p value | FC | p value | FC |
| 178 | Putrescine.K2 | 4.78E−01 | −14.07 | 7.29E−01 | −0.93 | 2.58E−01 | 13.02 |
| 179 | Spermidine.K2 | 5.72E−01 | −3.47 | 5.35E−02 | 40.24 | 9.52E−02 | 45.12 |
| 180 | Spermine.K2 | 3.75E−01 | −9.70 | 2.79E−01 | 63.28 | 1.85E−03 | 79.12 |
| 181 | Serotonin.K2 | 2.61E−01 | −83.99 | 1.77E−01 | −74.22 | 9.73E−01 | 5.61 |
| 182 | Creatinine.K2 | 1.55E−01 | −16.47 | 4.39E−01 | −13.49 | 4.74E−01 | 2.62 |
| 183 | Lac.EM | 8.43E−01 | −18.46 | 9.11E−01 | −14.73 | 6.68E−01 | 3.25 |
| 184 | Fum.EM | 7.20E−02 | −214.43 | 8.16E−02 | −101.23 | 5.13E−01 | 56.25 |
| 185 | Asp.EM | 1.75E−01 | −19.83 | 1.18E−01 | −82.39 | 7.62E−01 | −52.21 |
| 186 | Arg.EM | 3.47E−01 | −5.31 | 5.73E−01 | −22.10 | 8.39E−01 | −15.94 |
| 187 | Pyr + OAA.EM | 9.13E−02 | −19.37 | 7.31E−01 | 5.96 | 1.28E−01 | 26.49 |
| 188 | Suc.EM | 6.12E−02 | −191.05 | 1.83E−01 | −76.47 | 2.76E−01 | 64.92 |
| 189 | alpha-KGA.EM | 1.88E−01 | −83.12 | 1.17E−02 | −92.84 | 7.30E−01 | −5.31 |
| 190 | Hex.EM | 1.08E−01 | −13.33 | 1.96E−01 | −10.36 | 3.88E−01 | 2.69 |
| 191 | TCDCA.BA | 6.44E−01 | 10.96 | 3.79E−02 | 114.26 | 1.84E−01 | 93.09 |
| 192 | GCA.BA | 5.37E−01 | −12.87 | 2.44E−01 | 49.49 | 4.11E−02 | 68.73 |
| 193 | CA.BA | 2.40E−02 | −117.69 | 3.36E−01 | −57.06 | 6.52E−02 | 38.60 |
| 194 | UDCA.BA | 3.72E−01 | −35.25 | 9.26E−01 | −16.69 | 2.75E−01 | 15.90 |
| 195 | CDCA.BA | 3.30E−02 | −187.92 | 2.24E−01 | −63.25 | 2.57E−01 | 76.36 |
| 196 | GCDCA.BA | 6.70E−01 | 1.14 | 2.00E−01 | 41.56 | 4.46E−01 | 39.97 |
| 197 | LCA.BA | 6.02E−01 | −16.44 | 9.35E−01 | 3.86 | 3.66E−01 | 20.93 |
| 198 | 13S-HODE.PA | 9.42E−01 | −2.53 | 2.18E−01 | 72.20 | 2.09E−01 | 76.56 |
| 199 | DHA.PA | 9.31E−01 | −5.99 | 9.31E−01 | −4.42 | 8.59E−01 | 1.50 |
| 200 | AA.PA | 1.04E−01 | 28.00 | 6.09E−01 | 11.97 | 2.41E−01 | −14.31 |
| 201 | Orn/Cit | 1.10E−01 | 31.05 | 8.38E−01 | −0.80 | 1.46E−01 | −32.10 |
| 202 | Orn/Arg | 1.34E−01 | 25.38 | 7.82E−01 | 8.07 | 6.30E−02 | −16.02 |
| 203 | Cit/Arg | 6.85E−01 | −17.97 | 7.05E−01 | −12.25 | 9.48E−01 | 5.09 |
| 204 | Glu/Gln | 2.91E−01 | 6.21 | 4.42E−01 | −2.87 | 6.66E−01 | −9.26 |
| 205 | Asp/Asn | 1.02E−01 | −30.37 | 6.26E−01 | 21.61 | 6.92E−02 | 58.55 |
| 206 | Ala/Lys | 5.10E−01 | −7.97 | 5.38E−01 | −4.50 | 2.06E−01 | 3.32 |
| 207 | Phe/Tyr | 5.62E−01 | −7.44 | 3.12E−01 | 4.31 | 1.97E−01 | 12.06 |
| 208 | Serotonin/Trp | 3.14E−01 | −110.30 | 1.97E−01 | −71.38 | 9.79E−01 | 22.71 |
| 209 | Kyn/Trp | 8.00E−01 | −2.32 | 8.81E−01 | 1.70 | 9.06E−01 | 4.07 |
| 210 | Kyn/OHKyn | 1.30E−01 | 17.62 | 2.21E−01 | 30.22 | 8.28E−01 | 10.71 |
| 211 | Putrescine/Orn | 4.32E−01 | −39.18 | 3.45E−01 | 9.58 | 1.06E−01 | 52.52 |
| 212 | Spermine/Spermidine | 5.14E−02 | −39.58 | 1.48E−01 | −35.59 | 4.12E−01 | 2.94 |
| 213 | SDMA/ADMA | 3.48E−01 | 15.88 | 3.77E−01 | 5.59 | 7.98E−01 | −9.74 |
| 214 | Met-SO/Met | 4.28E−01 | −3.63 | 1.12E−02 | 20.89 | 2.42E−01 | 25.29 |
| 215 | Ala/BCAA | 2.60E−01 | 18.55 | 3.57E−01 | 10.57 | 6.82E−01 | −7.21 |
| 216 | Gly/BCAA | 2.28E−01 | 21.97 | 6.82E−01 | 15.36 | 3.67E−01 | −5.73 |
| 217 | SumLyso | 4.74E−02 | −20.90 | 2.82E−02 | −21.95 | 8.18E−01 | −0.87 |
| 218 | SumPC + Lyso | 2.70E−01 | −3.76 | 8.26E−02 | −10.76 | 5.53E−01 | −6.75 |
| 219 | SumPC | 4.77E−01 | 1.00 | 1.40E−01 | −7.31 | 5.40E−01 | −8.39 |
| 220 | SumSM | 1.50E−01 | −7.55 | 3.73E−01 | −4.99 | 8.18E−01 | 2.43 |
| 221 | SumSMOH/SumSM | 5.94E−01 | −0.27 | 8.18E−01 | 0.16 | 5.92E−01 | 0.44 |
| 222 | C16 + C18/C0 | 9.39E−02 | −29.71 | 4.59E−01 | −3.61 | 2.30E−01 | 25.20 |
| 223 | SumMUFA | 2.47E−01 | −2.35 | 1.90E−01 | −5.80 | 7.79E−01 | −3.36 |
| 224 | SumPUFA | 3.28E−01 | −2.39 | 1.28E−01 | −8.94 | 6.30E−01 | −6.39 |
| 225 | SumSFA | 7.68E−02 | −8.94 | 3.66E−02 | −14.46 | 5.93E−01 | −5.07 |
| 226 | PUFA/SFA | 2.71E−01 | 6.76 | 2.00E−01 | 5.69 | 9.72E−01 | −1.01 |
| 227 | PUFA/MUFA | 9.54E−01 | −0.89 | 3.17E−01 | −0.83 | 3.70E−01 | 0.05 |
| 228 | MUFA/SFA | 1.80E−01 | 0.32 | 5.74E−02 | 4.47 | 6.54E−01 | 4.13 |
| 229 | 24SOHC | 6.91E−02 | −24.12 | 2.19E−04 | −70.17 | 8.62E−03 | −37.11 |
| 230 | 25OHC | 5.60E−02 | −18.40 | 8.37E−04 | −59.28 | 9.86E−02 | −34.53 |
| 231 | 27OHC | 3.32E−02 | −22.36 | 1.61E−02 | −22.72 | 8.30E−01 | −0.29 |
| 232 | 24,25,EPC | 3.06E−01 | −37.01 | 2.45E−03 | −92.73 | 9.73E−03 | −40.67 |
| 233 | 7aOHC | 7.83E−02 | 24.50 | 1.28E−01 | 36.14 | 7.20E−01 | 9.36 |
| 234 | 5B,6B,EPC | 1.67E−01 | 14.26 | 2.04E−02 | 49.53 | 1.65E−01 | 30.87 |
| 235 | 5a,6a,EPC | 4.59E−01 | 16.71 | 6.71E−02 | 31.18 | 1.94E−01 | 12.40 |
| 236 | 4BOHC | 4.96E−02 | −17.82 | 2.26E−02 | −22.85 | 4.57E−01 | −4.26 |
| 237 | Desmosterol | 9.73E−01 | 30.36 | 8.19E−01 | 18.46 | 7.87E−01 | −10.05 |
| 238 | 7DHC | 2.55E−01 | 51.11 | 9.03E−01 | 1.48 | 2.49E−01 | −48.91 |
| 239 | Cholestenone | 4.96E−01 | 5.98 | 7.89E−01 | 29.61 | 6.26E−01 | 22.30 |
| 240 | Lanosterol | 9.61E−01 | 2.92 | 7.67E−03 | −109.37 | 4.04E−03 | −115.49 |
| 241 | 24DHLan | 6.89E−01 | −3.62 | 6.57E−01 | −142.35 | 2.32E−01 | −133.88 |

The invention claimed is:

1. A method for in vitro early diagnosing and treating asphyxia and disorders related thereto, comprising:
   a) selecting a plurality of asphyxia specific compounds selected from the first 30 ranked compounds of Table 2;
   b) quantitatively detecting a plurality of asphyxia specific compounds from the first 30 ranked compounds of Table 2 in the blood of a neonate;
   wherein said quantitatively detecting comprises:
      analyzing at least one blood sample of a neonate and measuring at least one measured value of concentration, level or amount of each of the selected compounds
      wherein said analyzing and measuring is by chromatography, mass spectrometry, enzyme-linked immunosorbent assay (ELISA), antibody linkage, immunochemical techniques, biochemical or enzymatic reactions or assays, or combinations thereof,
   c) calibrating said at least one measured value, and
   d) diagnosing asphyxia or an asphyxia disorder and administering a treatment to a diagnosed neonate selected from the group consisting of administering oxygen and administering hypothermia
   wherein said calibrating comprises:
   a) mathematically preprocessing the at least one measured value in order to reduce technical errors in said measuring;
   b) selecting at least one suitable classifying algorithm from the group consisting of logistic regression, linear or quadratic discriminant analysis, perceptron, shrunken centroids regularized discriminant analysis, random forests, neural networks, Bayesian networks, hidden Markov models, support vector machines, generalized partial least squares, partitioning around medoids, inductive logic programming, generalized additive models, gaussian processes, regularized least square regression, self organizing maps, recursive partitioning and regression trees, K-nearest neighbor classifiers, fuzzy classifiers, bagging, boosting, and naïve Bayes; and applying said selected classifier algorithm to preprocessed data of step a);
   c) training said at least one suitable classifying algorithm of step b) on at least one training data set containing preprocessed data from subjects divided into classes according to their asphyxia-related pathophysiological, physiological, prognostic, or responder conditions, in order to select a classifier function to map said preprocessed data to said conditions; and
   d) applying said trained at least one suitable classifying algorithm step c) to a preprocessed data set of a subject with unknown asphyxia-related pathophysiological, physiological, prognostic, or responder condition, and using the trained at least one suitable classifying algorithm to predict a class label of said data set in order to diagnose an asphyxia status of the subject.

2. Method according to claim 1, wherein said asphyxia comprises perinatal asphyxia, choking, drowning, electric shock, injury, or the inhalation of toxic gases, and said disorders being related thereto comprise hypoxic ischemic encephalopathy.

3. Method according to claim 1, wherein said step of mathematically preprocessing is carried out by a statistical method selected from the group consisting of:
   in case of raw data obtained by optical spectroscopy, background correction and/or normalization; and
   in case of raw data obtained by mass spectroscopy or mass spectroscopy coupled to liquid or gas chromatography or capillary electrophoresis or by 2D gel electrophoresis, quantitative determination with ELISA or RIA or determination of concentrations/amounts by quantitation of immunoblots or quantitation of amounts of biomolecules bound to aptamers: smoothing, baseline correction, peak picking, optionally, additional further data transformation such as taking the logarithm in order to carry out a stabilization of the variances.

4. Method according to claim 1, wherein after said step of mathematically preprocessing a further step of feature selection is inserted, in order to find a lower dimensional subset of features with the highest discriminatory power between classes;
   wherein said feature selection is carried out by a filter and/or a wrapper approach; and/or
   wherein said filter approach includes rankers and/or feature subset evaluation methods; and/or wherein said wrapper approach is applied, where a classifier is used to evaluate attribute subsets.

5. Method according to claim 1, wherein said asphyxia-related pathophysiological condition corresponds to the label "diseased" and said physiological condition corresponds to the label "healthy" or said asphyxia-related pathophysiological condition corresponds to different labels of "grades of a disease", "subtypes of a disease", different values of a "score for a defined disease"; said prognostic condition corresponds to a label "good", "medium", "poor", or "therapeutically responding" or "therapeutically non-responding" or "therapeutically poor responding".

6. Method according to claim 1, wherein metabolic data for said plurality of metabolites comprises high-throughput mass spectrometry data.

7. Method according to claim 1, wherein said asphyxia disorder comprises hypoxic ischemic encephalopathy,
   wherein missing data is imputed;
   wherein raw data of metabolite concentrations are preprocessed using log transformation;
   wherein linear mixed effect models are used to identify metabolites which are differentially present;
   wherein random forest is selected as the at least one suitable classifying algorithm, the training of the at least one suitable classifying algorithm including preprocessed metabolite concentrations is carried out with stratified bootstrap replications;
   applying said trained random forest classifying algorithm to said preprocessed metabolite concentration data set to a subject under suspicion of having hypoxic ischemic encephalopathy, and using the trained classifier to diagnose hypoxic ischemic encephalopathy.

8. Method according to claim 1, wherein the method further comprises inclusion of parameters selected from the group consisting of blood gases, arterial blood oxygen, blood pH, base status, and lactate, serum and/or plasma levels of low molecular weight biochemical compounds, enzymes, enzymatic activities, cell surface receptors, and cell counts.

9. The method according to claim 1, further comprising beginning a resuscitation protocol.

10. The method according to claim 1, wherein said administering treatment comprises administering hypothermia.

11. The method according to claim 1, wherein said administering treatment comprises administering oxygen.

12. A method for in vitro early diagnosing and treating of asphyxia and disorders related thereto, comprising:

measuring the presence or absence or a differential level of a plurality of asphyxia-specific metabolites selected from the first 30 ranked metabolites of Table 2 in the blood of a neonate;

determining measured values of concentration, level, or amount of each of the selected metabolites;

comparing the measured values to asphyxia-positive or asphyxia-negative reference levels of said metabolites;

diagnosing asphyxia or an asphyxia disorder and its duration based on said comparing; and administering a treatment to a diagnosed neonate selected from the group consisting of administering oxygen and administering hypothermia.

13. The method according to claim 12, wherein said reference levels are tailored to a technique used for said measuring, where the measured levels differ based on the technique.

14. The method according to claim 12, wherein said administering treatment comprises administering hypothermia.

15. The method according to claim 12, wherein said administering treatment comprises administering oxygen.

* * * * *